United States Patent
Yekhanin et al.

(10) Patent No.: US 11,495,324 B2
(45) Date of Patent: Nov. 8, 2022

(54) FLEXIBLE DECODING IN DNA DATA STORAGE BASED ON REDUNDANCY CODES

(71) Applicant: Microsoft Technology Licensing, LLC, Redmond, WA (US)

(72) Inventors: Sergey Yekhanin, Redmond, WA (US); Sivakanth Gopi, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 507 days.

(21) Appl. No.: 16/590,320

(22) Filed: Oct. 1, 2019

(65) Prior Publication Data

US 2021/0098081 A1   Apr. 1, 2021

(51) Int. Cl.
*G16B 30/20* (2019.01)
*G06F 16/23* (2019.01)
*G16B 30/10* (2019.01)

(52) U.S. Cl.
CPC ......... *G16B 30/20* (2019.02); *G06F 16/2365* (2019.01); *G16B 30/10* (2019.02)

(58) Field of Classification Search
CPC ........ G16B 30/20; G16B 30/10; G16B 50/20; G06F 16/2365
See application file for complete search history.

(56) References Cited

U.S. PATENT DOCUMENTS

2018/0211001 A1   7/2018   Gopalan et al.

FOREIGN PATENT DOCUMENTS

WO   WO 2017/189469   11/2017
WO   WO 2018/063950   4/2018

OTHER PUBLICATIONS

Yashodha, New Trends of Digital Data Storage in DNA, pp. 1-15 (Year: 2016).*
Templeton, How DNA data storage works, pp. 1-5 (Year: 2016).*
International Search Report and Written Opinion received in counterpart PCT/US2020/045829, dated Nov. 11, 2020, 15 pages.
U.S. Appl. No. 16/105,349, filed Aug. 20, 2018, Racz et al.
Blawat, et al., "Forward Error Correction for DNA Data Storage", In Journal of Procedia Computer Science, vol. 80, Jan. 1, 2016, pp. 1011-1022, 12 Pages.
Erlich, et al., "DNA Fountain Enables a Robust and Efficient Storage Architecture", In Journal of Science, vol. 355, Issue 6328, Mar. 3, 2017, 4 Pages.

(Continued)

*Primary Examiner* — Albert M Phillips, III
(74) *Attorney, Agent, or Firm* — Klarquist Sparkman, LLP

(57) ABSTRACT

Data that has been stored according to a DNA data storage method can be decoded using a flexible approach that supports both solitary strand mapping and cluster-based trace reconstruction. Solitary strand mapping can place strings based on integrity verification. Redundancy information can be partitioned to support error correction during the solitary strand mapping while still achieving integrity verification. Clusters with verified strands can be skipped during cluster-based trace reconstruction. Useful for increasing the accuracy of the trace reconstruction procedure.

20 Claims, 28 Drawing Sheets
Specification includes a Sequence Listing.

(56) References Cited

OTHER PUBLICATIONS

Grass, et al., "Robust Chemical Preservation of Digital Information on DNA in Silica with Error-Correcting Codes", In Journal of the German Chemical Society-Publication of Angewandte Chemie International Edition, vol. 54, Issue 8, Feb. 16, 2015, pp. 2552-2555. 4 Pages.

Levenshtein, V.I, "Binary Codes Capable of Correcting Deletions, Insertions, and Reversals", In Journal of Soviet Physics-Doklady, vol. 10, No. 8, Feb. 10, 1966, 4 Pages.

MacWilliams, et al., "The Theory of Error-Correcting Codes", In Publication of Elsevier, Jan. 1977, 771 Pages.

Organick, et al., "Random Access in Large Scale DNA Data Storage", In Proceeding of Nature Biotechnology, vol. 36, Issue 3, Mar. 2018, 9 Pages.

Tenengolts, Grigory, "Nonbinary Codes, Correcting Single Deletion or Insertion", In Proceedings of IEEE Transactions on Information Theory, vol. 30, Issue 5, Sep. 1984, pp. 766-769, 4 Pages.

\* cited by examiner

SUBSTITUTION

DELETION

INSERTION

INDETERMINANT ERROR

CENTERED

EQUALLY SPACED

CENTER-BIASED SPACING

SEQUENCE LISTING

```
<160> NUMBER OF SEQ ID NOS: 4

<210> SEQ ID NO 1
<211> LENGTH: 14
<212> TYPE: DNA
<213> ORGANISM: Artificial Sequence
<220> FEATURE:
<223> OTHER INFORMATION: Synthetic nucleotide sequence

<400> SEQUENCE: 1
agctggacgt aggc                                                      14

<210> SEQ ID NO 2
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 2
```

```
agattgatct acgc                                            14

<210> SEQ ID NO 3
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 3
atcttgagct acgt                                            14

<210> SEQ ID NO 4
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 4
agcctgagcc acgc                                            14
```

FLEXIBLE DECODING IN DNA DATA STORAGE BASED ON REDUNDANCY CODES

FIELD

The field generally relates to DNA data storage.

BACKGROUND

Demand for data storage is outpacing the capacity of conventional storage media. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding the string, sequenced the synthetic DNA, and then recovered the original computer file with 100% accuracy.

However, while amazing strides have been made in the field, there still remains room for improvement, particularly in how errors are addressed by the encoding and decoding processes. Although it has advantages, a DNA storage system must overcome challenges relating to errors. For example, DNA synthesis, degradation during storage, and sequencing are all potential sources of errors. Thus, the DNA sequence output by a sequencer may be different from the DNA sequence originally provided to an oligonucleotide synthesizer, even though they are intended to be identical.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a method comprises, in a first pass through a plurality of nucleotide symbol strings representing nucleotide strand sequence reads from a polynucleotide sequencer, wherein the nucleotide strand sequence reads represent logically ordered nucleotide symbol strings comprising encoded data with redundancy information, placing a nucleotide symbol string representing a solitary nucleotide strand sequence read in a first order position of an ordered map; and in a second pass through the nucleotide symbol strings representing nucleotide strand sequence reads from the polynucleotide sequencer, performing cluster-based trace reconstruction, wherein the cluster-based trace reconstruction generates a reconstructed nucleotide symbol string and places the reconstructed nucleotide symbol string in a second order position of the ordered map.

In another embodiment, a system comprises one or more processors; memory coupled to the one or more processors; a string position map storing a mapping between addresses and nucleotide symbol strings; wherein the memory comprises computer-executable instructions causing the one or more processors to perform operations comprising: during processing of a nucleotide symbol string representing a solitary strand read by a sequencer, responsive to determining that the nucleotide symbol string passes integrity verification, placing the nucleotide symbol string into the string position map; and, during processing of a cluster of nucleotide symbol strings representing a plurality of strands read by the sequencer, reconstructing a reconstructed nucleotide symbol string based on the cluster and placing the reconstructed nucleotide symbol string into the string position map.

In another embodiment, one or more computer-readable media comprise computer-executable instructions capable of causing a computing system to place, in a first order position of an ordered map, a nucleotide symbol string representing a solitary nucleotide strand sequence read, wherein the nucleotide symbol string is one out of a plurality of nucleotide symbol strings representing respective nucleotide strand sequence reads from a polynucleotide sequencer, wherein the nucleotide strand sequence reads represent logically ordered comprising encoded data with redundancy information, and wherein the nucleotide symbol string is placed in the first order position of the ordered map responsive to determining that it passes integrity verification; and computer-executable instructions capable of causing the computing system to perform cluster-based trace reconstruction on the plurality of nucleotide symbol strings, wherein the cluster-based trace reconstruction generates a reconstructed nucleotide symbol string out of a cluster of the plurality of nucleotide symbol strings and places the reconstructed nucleotide symbol string in a second order position of the ordered map.

The foregoing and other objects, features, and advantages will become more apparent from the following detailed description, which proceeds with reference to the accompanying figures.

DETAILED DESCRIPTION

Example 1—Overview

Figure 1:
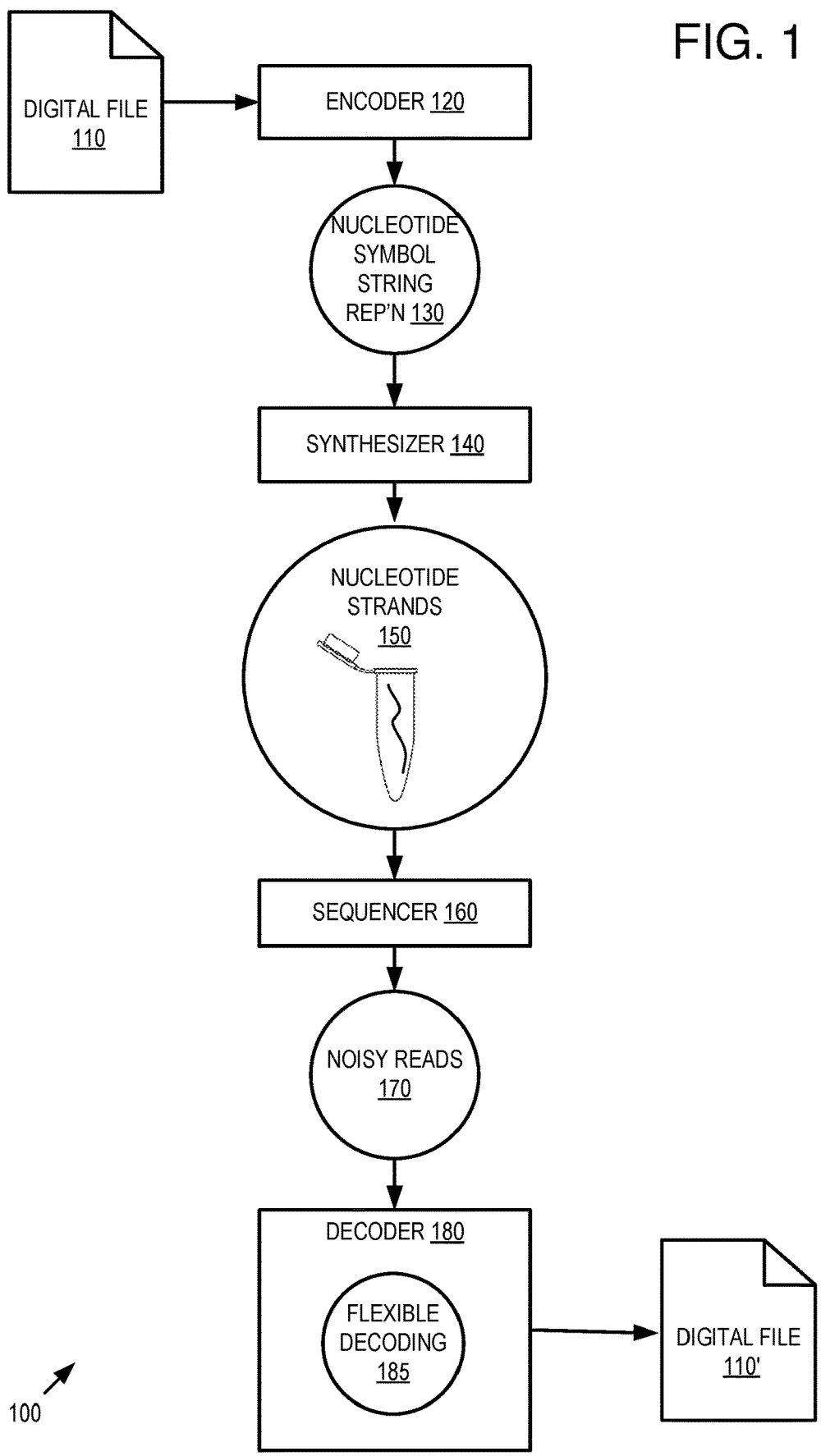
FIG. 1 is a block diagram of an example system implementing flexible decoding in DNA data storage based on redundancy codes.

A number of flexible decoding technologies for encoding data in a DNA storage context are described herein. Such technologies can be useful generally in DNA storage scenarios because of their error-resistant nature.

Notably, the error profile of DNA data storage can be quite different from that of conventional digital data. Therefore, new approaches to redundancy are needed to address error processing.

Existing DNA coding schemes tend to use so-called "concatenated" codes. For example, the data is represented by a collection of DNA strands, where each strand carries some redundant information that is local to the strand (an "inner coding") as well as some redundant information that is global, across strands ("outer coding").

In DNA storage, the strands are stored (e.g., physically) unordered. To make use of the outer redundancy and to be able to recover the data, one needs to maintain an ordering of the strands. Thus, a strand typically has a short prefix that carries its address (e.g., the position of the strand relative to the other strands). Thus, the strands are logically ordered by their address.

To access data that is stored in DNA, one performs DNA sequencing and then invokes the decoding process. Such a process typically takes as an input an unordered collection of noisy reads of DNA strands from a sequencer, where the number of reads varies with the position of the strand (e.g., there may be some positions that have zero reads), and each read may contain insertion, deletion, or substitution errors. The rate of errors depends on the technologies used in synthesis and sequencing. For data sequenced on platforms of Illumina, Inc., the rate of sequencing errors is around 1%. For nanopore sequenced data, the rate of sequencing errors is around 10%. The rate of synthesis errors is typically below the rate of sequencing errors.

In order to decode the concatenated code, one needs to obtain estimates for strands that correspond to a significant number of positions. Such estimates need not be perfect and may contain substitution errors that will later be corrected by relying on the redundancy of the coding scheme.

Various approaches can be used to go from a collection of noisy reads that come from the sequencer to estimates for strands in positions. One approach is to map a read to a position individually, based on the prefix that carries the address. Inner redundancy can be used for error detection or correction.

Another approach is similar, but where there are multiple reads that are mapped to a same position, the reads are combined to produce a final estimate for the position.

In another approach, individual reads are not mapped to positions. Instead, noisy reads are processed jointly to obtain a new collection of strands that are later mapped to positions based on their address. Clustering and trace reconstruction can be used.

The clustering approach is generally more powerful because it may still produce good estimates for a position even if all reads for the position are noisy. However, it requires significant computational power and is not easy to parallelize across machines.

There are cases, however, where the clustering approach can fail. For example, if all but a few reads for a specific position are very noisy, and the few (or one) reads are perfectly correct, clustering may fail, while other approaches will succeed. Such cases have been demonstrated to be a problem in actual practice.

A flexible approach can combine both a solitary-strand-based approach and a cluster-based approach as described herein.

As a result, overall accuracy can be improved, leading to a reduction in the amount of redundancy needed during coding, the amount of coverage needed during decoding, or both. The techniques can thus reduce the cost of encoding the data, the cost of decoding the data, or both. Such an improvement can lead to more widespread use of the technology.

Because the technologies relate to encoding and decoding data, they can be applied across a large number of use cases involving DNA data storage and retrieval.

Example 2—Example Terminology

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes for using nucleotide bases to represent digital information. See e.g., Grass et al., "Robust Chemical Preservation of Digital Information on DNA in Silica with Error-Correcting Codes," 54 Angew. Chem. Int. Ed. 2552 (2015) and Organick et al., "Random access in large-scale DNA data storage," 36:3 Nat. Biotech. 243 (2018). Advantages of using DNA rather than another storage media for storing digital information include information density and longevity. DNA data storage can improve information density, longevity, and accessibility. The contents of the disclosure may be used with any type of polynucleotide such as DNA, RNA, and DNA-RNA hybrids, thus references to "DNA" are illustrative and not intended to limit the application to only DNA or to only use of natural nucleotide bases.

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the reverse complement of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention DNA for the sake of brevity and readability, but RNA may be used in place of or in combination with DNA. RNA may also bind to DNA forming a hybrid molecule.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

"Hybridizing" as used herein means placing two complementary single-strand (ss) (or partially single-strand) DNA strands in conditions that allow hybridization to form a double-strand (ds) DNA strand or causing two complementary ssDNA strands to hybridize and form a dsDNA strand. Hybridization may be performed under high stringency conditions.

Artificial synthesis of DNA allows for creation of DNA strands with arbitrary series of the nucleotides. The order in which individual monomers of these four nucleotides are assembled together into a polymer can represent information in an analogous manner as 0 and 1 in digital computers. Thus, multiple DNA strands can be synthesized with particular orders of the four DNA nucleotides and encode large amounts of information. The information is encoded as a series of DNA nucleotides, but may represent any type of data such as text, audio files, video files, or anything else that may be encoded by conventional binary data recording in electronic computers.

The term "primer" as used herein refers to an oligonucleotide which is capable of acting as a point of initiation of nucleic acid synthesis when placed under conditions in which synthesis of a primer product, which is complementary to a nucleic acid strand, is induced (e.g., in the presence of four different nucleotide triphosphates with appropriate enzymes at a suitable temperature and salt concentration). Specific length and sequence will depend on the complexity of the required primer targets, as well as on the conditions of primer use such as temperature and ionic strength. In some implementations, a primer can be 5-50 nt, 10-25 nt, or 15-20 nt in length. The fact that amplification primers do not have to match exactly with the corresponding template sequence to warrant proper amplification is amply documented in the literature. It is generally accepted that a typical length of PCR primers is 18-22 nt. This length is long enough for adequate specificity and short enough for primers to bind easily to the template at the annealing temperature.

The term "amplifying" which typically refers to an exponential increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including polymerases and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art.

One technique for amplification is PCR which may use a PCR thermocycler. A variety of PCR techniques are known and can be used with the techniques described herein. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Kienow fragment of DNA polymerase I and the HIV-1 polymerase.

The entire contents of a DNA pool, or other vessel containing the DNA to be analyzed, may be placed in a PCR thermocycler. The process of PCR is well-known to those skilled in the art and has been extensively characterized. PCR involves the following three steps: denaturation, annealing, and extension. First, any dsDNA is denatured, converting to single strands. The primers are then annealed to the complementary regions of the single stranded molecules. In the third step, the primers are extended by the action of the DNA polymerase. All these steps are temperature sensitive and a common choice of temperatures is 94° C., 60° C., and 70° C., respectively. In order to amplify the sequencing adaptors together with the designated DNA, the primers are designed to hybridize with the ends of the sequencing adaptors in order to create multiple copies of the ligation products. Melting Temperature ($T_m$) by definition is the temperature at which one half of a DNA duplex will dissociate to become single stranded and indicates the duplex stability. Primers with melting temperatures in the range of 52-58° C. generally produce the best results. Primers with melting temperatures above 65° C. have a tendency for secondary annealing. The GC content of the sequence gives a fair indication of the primer $T_m$. Other DNA strands from the DNA pool will still be present during PCR, but primers present in the PCR mix will be unlikely to hybridize with those DNA strands. The selectively amplified DNA generated by the PCR thermocycler may be provided to a DNA sequencer. PCR amplification prior to sequencing improves the yield and may convert ssDNA to dsDNA which improves the stability and longevity of DNA in storage.

Example 3—Example System Implementing
Flexible Decoding in DNA Data Storage

FIG. 1 is a block diagram of an example system 100 implementing flexible decoding in DNA data storage based on redundancy codes. In the example, the system 100 encodes a digital file 110 that is ultimately decoded as a copy 110' of the digital file 110.

The digital file 110 is typically a binary representation of underlying data of any arbitrary format. The encoder 120 accepts the digital file 110 as input and outputs a representation 130 of the digital file.

The technologies described herein can work with a wide variety of encoding techniques. Features such as redundancy (inner, outer, or the like), constrained encoding (e.g., so that the resulting nucleotide symbol strings meet a coding constraint), and randomization can be supported as described herein.

The resulting representation 130 can take the form of ordered nucleotide symbol strings. Although not required, the strings can be of fixed length by convention or as specified in metadata. An address can be included on the strings as described herein.

A nucleotide synthesizer 140 accepts the representation 130 as input and generates nucleotide strands (e.g., oligonucleotides) 150 according to the nucleotide symbol strings of the representation 130. At this point, the strands are logically ordered because they include an address; however, physically, the strands can be mixed together in an unordered fashion.

Subsequently, the physical material of the nucleotide strands 150 can be read by a sequencer 160 which ultimately outputs noisy reads 170 that are attempted reconstructions of the original input nucleotide symbol strings of the constrained representation 130.

A decoder 180 accepts the noisy reads 170 and generates a reconstructed copy 110' of the original digital file 110. The decoder 180 can include functionality 185 for implementing flexible decoding technologies as described herein.

The encoder 120 can be implemented on a computing system, as can the decoder 180. In practice, encoding and decoding can be performed on the same computing system or on separate computing systems. For example, one party may encode the digital file 110 and then provide the nucleotide sequences 150 to another party, which performs decoding.

The goal of the encoding/decoding process is to have an exact copy of the data emerge from the encoding/decoding process. However, in practice, it can be challenging to address errors introduced by synthesis and sequencing. Such errors can result in substitutions, deletions, and insertions. Accordingly, redundancy information is included in the encodings. As described herein, flexible decoding technologies 185 can address the particular challenges introduced by reordering the strands (e.g., trying to determining which read belongs in which position). As described herein, the flexible decoding technologies 185 can combine placement of a nucleotide string representing a solitary nucleotide strand sequence read with cluster-based trace reconstruction.

In practice, the systems shown herein, such as system 100, can vary in complexity, with additional functionality, more complex components, and the like. Additional components can be included to implement security, redundancy, load balancing, report design, and the like.

The described computing systems can be networked via wired or wireless network connections, including the Internet. Alternatively, systems can be connected through an intranet connection (e.g., in a corporate environment, government environment, or the like).

The system 100 and any of the other systems described herein can be implemented in conjunction with any of the hardware components described herein, such as the computing systems described below (e.g., processing units, memory, and the like). In any of the examples herein, the digital files, nucleotide symbol strings, redundancy symbols, noisy reads, string position map, and the like can be stored in one or more computer-readable storage media or computer-readable storage devices. The technologies described herein can be generic to the specifics of operating systems or hardware and can be applied in any variety of environments to take advantage of the described features.

Example 4—Example Method Implementing
Flexible Decoding in DNA Data Storage

Figure 2:
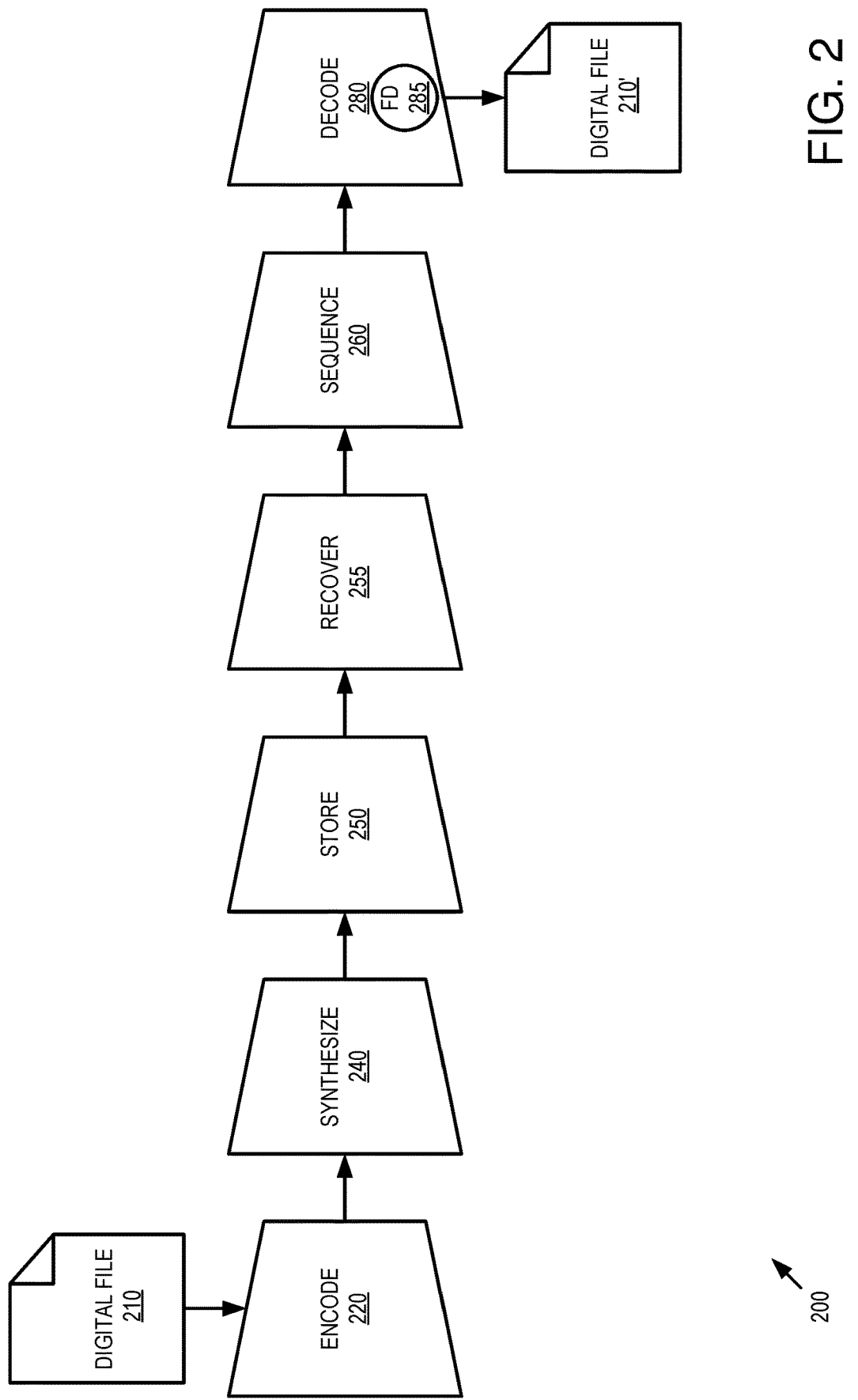
FIG. 2 is a flowchart of an example method of implementing flexible decoding in DNA data storage based on redundancy codes.

FIG. 2 is a flowchart of an example method 200 of implementing flexible decoding in DNA data storage based on redundancy codes and can be performed, for example, by the system of FIG. 1.

At 220, a digital file 210 is encoded (e.g., into a quaternary string) as described herein. The resulting output is nucleotide symbol strings, which are synthesized into nucleotide strands (e.g., oligonucleotides) at 240. In practice, multiple copies of each strand can be synthesized. Addresses can be added to the stings (e.g., and thus the strands) to preserve logical ordering and facilitate reassembly during the decoding process.

The physical nucleotide strands can be stored at 250 and subsequently recovered at 255. In practice, amplification can be used to increase the number of copies of the strands, whether before or after storage or both.

At 260, the input nucleotide sequences can be sequenced (i.e., read), resulting in output nucleotide symbol strings (e.g., noisy reads) that are decoded at 280 using decoding techniques 285 that implement flexible decoding, resulting in a copy 210' of the digital file 210.

In practice, a single party may perform all the acts shown; however, it is also possible that a single party only performs some actions (e.g., on the encoding side) while another party performs others (e.g., on the decoding side). Division of tasks may also take place along domain lines (e.g., one party performs the digital calculations while another performs the wetware functions of synthesis and sequencing).

The method 200 and any of the other methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

When implemented in computer-readable media, the technologies can comprise computer-executable instructions capable of causing a computing system to perform respective of the method steps.

The illustrated actions can be described from alternative perspectives while still implementing the technologies.

Example 5—Example DNA Data Storage Scenarios

Binary data of the kind currently used by computers to store text files, audio files, video files, software, and the like can be represented as a series of nucleic acids in a polynucleotide (i.e., DNA or ribonucleic acid (RNA)). There are multiple techniques for representing the 0 and 1 of binary data as a series of nucleotides. A polynucleotide sequence is designed to hold the binary data and then synthesized with an oligonucleotide synthesizer. The synthesized polynucleotide is placed into storage, it is ultimately read by a polynucleotide sequencer. The data generated by the polynucleotide sequencer is decoded to recover the stored binary data. The machines that write and read the sequences of polynucleotides are not 100% accurate and introduce errors. Some types of errors, such as insertions, deletions, or substitutions of a nucleotide, can be identified and corrected. Other types of errors, in particular "bursty" errors in which there are multiple errors in a localized "burst" adjacent or close to each other, can be difficult or impossible to correct.

Example 6—Example Digital File

In any of the examples herein, a digital file can take the form of digital information of any arbitrary format or length. In practice, any information representable in digital form can be stored by the digital file (e.g., image, sound, video, text, hypertext, database, attribute, markup language, object notation, application files, executable content, compressed data, and the like).

The digital file can be converted to a nucleotide symbol string by encoding it as quaternary data (e.g., in a quaternary alphabet). Such encoding can take different forms, such as using A, C, G, and T to represent different combinations of 1's and 0's (e.g., A represents 00, C represents 01, G represents 10, and T represents 11 or the like); a one-hot encoding can be used (e.g., one nucleotide symbol represents 1, and the others represent 0); or the like. The nucleotide symbol string can be implied based on the digital data (e.g., actual A's, C's, G's, and T's need not be stored as long as there is a way to differentiate between them).

In any of the decoding examples herein, a resulting quaternary string can be decoded to recover the original digital data.

However, such a raw encoding is typically not suitable for synthesis of nucleotide strands for a number of reasons. For example, redundancy is typically needed to address errors, and a constrained encoding may be desired to better accommodate synthesis and/or sequencing technologies.

To facilitate storage in spite of errors that inevitably occur during DNA synthesis, storage, and sequencing, data coding includes redundancy as described herein.

Example 7—Example Nucleotide Symbol Strings

In any of the examples herein, a nucleotide symbol string can take the form of a string of nucleotide symbols. In practice, a set of strings representing a digital file can be logically arranged in a grid-like format. For example, rows can represent a string, and the rows are stacked on top of each other, forming columns. However, the logical arrangement or notation can vary depending on circumstances.

After the strings are synthesized as physical nucleotide strands, they are placed into a storage medium and lose their ordering. To preserve logical ordering, an address can be included on the string/strand.

Subsequently, when strings are recreated from the strands during the sequencing process, they can be ordered according to the address. Thus, the strings can be ordered during the decoding process to recreate the original grid-like format.

Due to currently available technology, the nucleotide symbol strings described herein typically take a length of 100-500 nt. However, as technology evolves, the length can be expected to increase. As shown herein, the initial length is typically shorter than the ultimate length due to the addition of constrained encoding, redundancy, address information, primers for amplification, and the like.

Although examples describe nucleotide strings for DNA, implementations using RNA, synthetic nucleotides, or some combination thereof can also be implemented.

In practice, a nucleotide symbol string (e.g., a row in a grid of strings) ultimately represents a nucleotide strand (e.g., a molecule). So, the terms "string" and "strand" can identify the same sequence of nucleotides, where one is stored in digital memory, and the other is stored in DNA.

Example 8—Example Encodings

In any of the examples herein, a variety of encodings can be used to transform data from an unencoded state to an encoded state. The data can then subsequently be transformed via decoding back to its original state. Encodings can also be used to generate redundancy information that does not transform input data as described herein.

Transformational encodings include those that impose a constraint on nucleotide symbol strings, or so-called "constrained encodings." Depending on the specific technologies employed for DNA synthesis and sequencing, to avoid catastrophic errors, encoding can be done so that strands exhibit a specific structure. A common type of such structure is a bound on the length of homopolymer runs for example, a strand where homopolymer run length is bounded by 2, a DNA strand cannot have 3 or more repeated occurrences of the same nucleotide. Other forms of constrained representation may include having different bounds for the length of allowed homopolymer runs for different bases. Such a constraint can be imposed, for example, due to difficulty in accurately synthesizing or sequencing a strand for a string that violates the constraint.

So, in a case where a constrained encoding is to impose a constraint that no more than 1 nucleotide value can appear in a row (e.g., there are no consecutive nucleotide symbols that have the same value), the constrained encoder can transform any arbitrary input nucleotide symbol string into one that does not have more than one identical nucleotide value in a row. Typically, such a string is of longer length due to the encoding process and is sometimes called a "constrained nucleotide symbol string" to reflect that it has been encoded with a constrained encoding.

The constrained nucleotide symbol string completely represents the original string, and decoding can unwind the encoding to recover the original string in its entirety.

In practice, a constrained representation can be applied in different ways. For example, an encoding can map the entire raw data as a very long string to a constrained representation and then partition the resulting long string into strands. Or the encoding can first partition the data into small pieces corresponding to individual strands, and then apply the constrained coding to the individual pieces.

Example 9—Example Redundancy

In any of the examples herein, another type of encoding produces redundancy information. Such redundancy information can be used for error-correction or integrity verification of the data for which it is produced.

Two broad classes of redundancy information include inner redundancy (e.g., the redundancy information is for data within a nucleotide symbol string) and outer redundancy (e.g., the redundancy information is for data across a plurality of nucleotide symbol strings).

Inner redundancy information can be generated for a string and then later used to correct the string and/or verify its integrity. Such inner redundancy information can take the form of additional nucleotide symbols that do not carry new information but are derived from the nucleotide symbols of the underlying strand. Such redundancy facilitates integrity verification or error correction of the strand.

Outer redundancy information can be generated across strings and then later used to correct the data and/or verify its integrity. Outer redundancy can be particularly useful in the DNA data storage context because errors often tend to cluster and/or be localized within a string. Redundancy across strings is thus orthogonal to the usual error patterns produced by synthesis and/or sequencing and can therefore recover information that inner coding cannot. Like inner redundancy information, outer redundancy information can take the form of additional nucleotide symbols that do not carry new information but is derived from the nucleotide symbols of the underlying cross-strand symbols. Such redundancy facilitates error correction where certain strands experienced catastrophic errors or are entirely missing from the output of the sequencing process.

The specific technique used to implement redundancy can vary. For example, a Reed Solomon code, LT code, or an LDPC code can be used. Hamming codes can also be employed. Integrity verification (e.g., error detection) can use any number of encodings, including a cyclical redundancy check (CRC), checksum, file integrity digests, and the like.

Redundancy can also be classified according to whether it corrects/detects substitution errors or insertion/deletion errors. In any of the examples herein where not otherwise noted, redundancy can correct or detect substitution errors, but some examples also correct or detect insertion/deletion errors as described. Insertions and deletions are particularly important in a DNA data storage context because synthesis and/or sequencing can introduce such errors, which are atypical in conventional digital processing.

Redundancy that can both correct errors as well as verify integrity can be desirable in nanopore sequencing scenarios due to the higher error rate exhibited by such technologies.

Example 10—Example Decoding System

Figure 3:
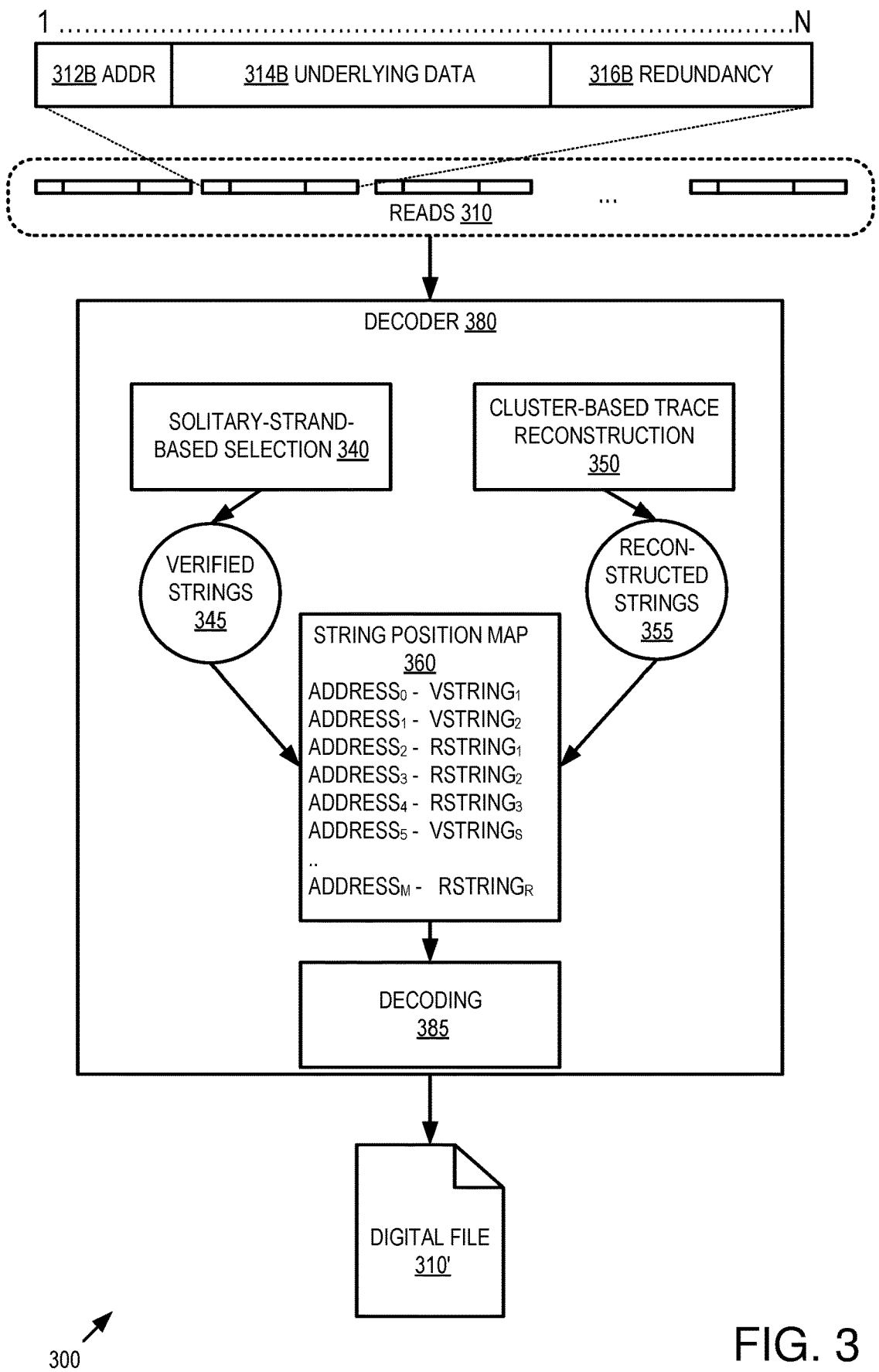
FIG. 3 is a block diagram of an example decoder system employing flexible decoding.

FIG. 3 is a block diagram of an example decoder system 300 employing flexible decoding that can be used in any of the examples herein. In the example, a decoder 380 receives a plurality of noisy reads 310 (e.g., from a sequencer sequencing encoded strands that represent an original data file).

An exploded view of a particular noisy read shows that a read can comprise an address region 312B, an underlying data region 314B, and a redundancy region 316B. In practice additional redundancy information can be included throughout the read, and redundancy can be partitioned as described herein.

In practice, a read equates to a strand, which equates to a string. Therefore, the terms are sometimes used interchangeably herein. For example, placing a "strand" in its proper position typically equates to finding a position for the nucleotide symbol string representing the strand (e.g., which is based on a read of the strand). However, it should be noted that there may not be exact correspondence. For example, errors can be introduced when reading the strand, and pre-processing on the nucleotide symbol string means that the string may not match the read exactly.

As described herein, the decoder 380 can be flexible in that it can implement both solitary-strand-based selection 340 and cluster-based trace reconstruction 350 when building the string position map 360.

Solitary-strand-based selection 340 results in one or more verified strings 345. As described herein, such selection can place a nucleotide symbol string (e.g., out of the nucleotide symbol strings representing the reads 310) representing a solitary nucleotide strand sequence read (e.g., out of the reads 310) in its proper order position in the ordered string position map 360.

Cluster-based trace reconstruction 350 results in one or more reconstructed strings 355 (e.g., based on respective string clusters) that are placed in the string position map 360 as described herein.

The decoder 380 can also include conflict resolution processing to resolve a conflict between solitary-strand-based selection 340 and cluster-based trace reconstruction 350 as described herein.

After the string position map 360 has been built, additional decoding 385 can be performed, resulting in the digital file 310' (e.g., a reconstructed version of the original input file).

Such additional decoding 385 can include additional redundancy processing (e.g., via outer redundancy). For example, it is possible that some entries are entirely missing from the map 360, but redundancy may still permit reconstruction of the file 310'. Still other processing (e.g., decompression and the like) can be performed as desired.

Example 11—Example Method of Flexible Decoding

Figure 4:
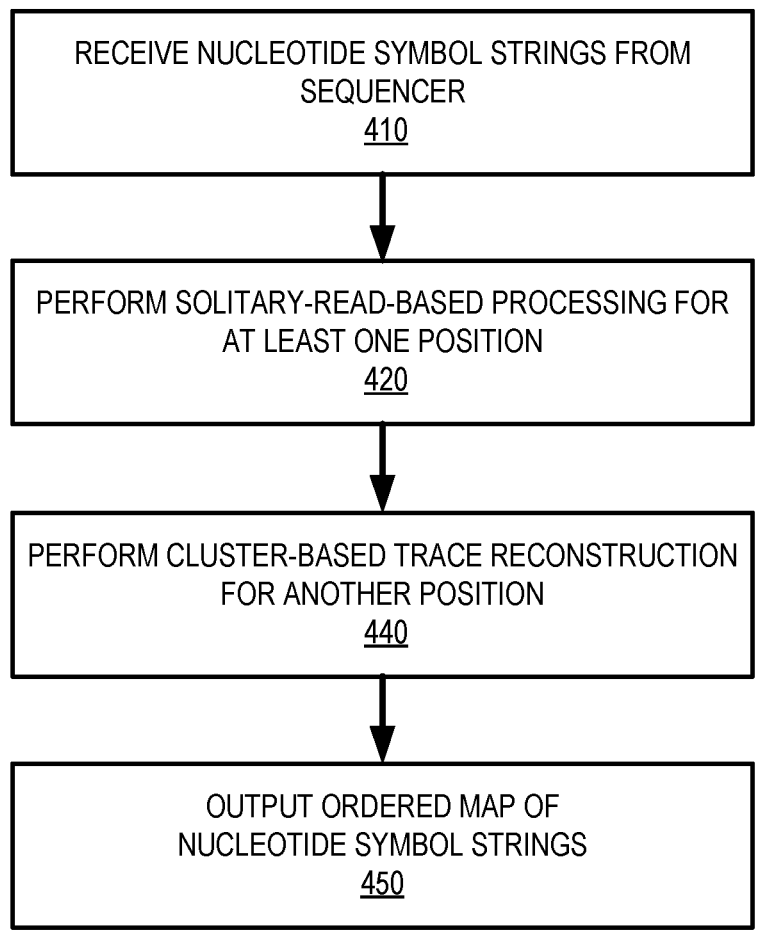
FIG. 4 is a flowchart of an example method of flexible decoding.

FIG. 4 is a flowchart of an example method 400 of flexible decoding that can be used in any of the examples herein for encoding and can be performed, for example, by the system of FIG. 3.

At 410, the nucleotide symbol strings are received. Such strings typically originate from a sequencer as described herein. However, preprocessing and filtering can be performed on the strings as noted herein. The symbol strings represent nucleotide strand sequence reads from a polynucleotide sequencer, and the nucleotide strand sequence reads represent (e.g., sometimes imperfectly due to errors) logically ordered nucleotide symbol strings comprising encoded data with redundancy information.

At 420, the method performs solitary-strand-based processing for at least one position of a string position map. It is also sometimes called "seriatim" processing because strings can be processed one-by-one. As described herein, such processing involves integrity verification for the placed string, and places the string responsive to determining that it passes integrity verification. So it can also be called "integrity-verification-based" processing. Such processing can place a nucleotide symbol string (e.g., out of the nucleotide symbol strings) representing a solitary nucleotide strand sequence read (e.g., out of the nucleotide symbol strings) in an order position of an ordered string map.

At 440, the method performs cluster-based trace reconstruction for at least one other position of the string position map. As described herein, such reconstruction generates a reconstructed nucleotide symbol string and places it in another order position of the string position map.

At 450, the ordered string map is output and can be used to then reconstruct the original digital file (e.g., via further decoding to convert the quaternary code can be converted back to the ones and zeros representing the digital file).

For sake of organization, the solitary-strand-based processing can be performed in a first pass through the strings, and the cluster-based trace reconstruction can be performed in a second pass. However, embodiments could use some other organization, and the first pass need not necessarily take place or be completed before the second pass. For example, passes can be performed in parallel, concurrently or the like.

In practice, amplification can be used so that there is more than one copy of any given strand; therefore, the decoding process can account for multiple copies.

Example 12—Example String Position Map

In any of the examples herein, a string position map can be used to map nucleotide symbol strings to positions in the overall ordering of the data to be decoded. In practice, the nucleotide strands being read are physically unordered, but are logically ordered so that the original ordering can be reconstructed during the decoding process.

Ordering can be achieved by including an address (e.g., a value that orders the strands) on the strand that represents a number using a quaternary alphabet. The address itself is subject to error, so incoming nucleotide symbol strings from a sequencer during the decoding process are not conclusive. Redundancy information can be configured to include the address so that integrity verification can verify that the address is indeed correct.

During the decoding process, the strands are represented by nucleotide symbol strings, so the so-called "strand position" becomes a string position at the decoding stage.

In practice, the map need not store the actual string. Instead, a reference (e.g., pointer) to the string can be used. Also, some strings in the map may not match any actual read strand. For example, error correction or trace reconstruction can generate a corrected (and verified) string or a reconstructed string.

Although some examples show an explicit address in the string position map, an address can be indicated by virtue of position in the map (e.g., the strings appear in order).

In some cases, due to redundancy information included in the strands, decoding can proceed even if there is an empty position in the map.

Example 13—Example Noisy Reads

In any of the examples herein, the term "noisy reads" can be used to indicate the output of a sequencer. It is generally expected that there is noise (e.g., errors) in the reads as a whole; however, as described herein, it is possible that some of the reads have few or no errors.

Additional pre-processing is sometimes performed before the resulting nucleotide symbol strings are actually processed. For example, de-randomization, unwinding a constrained encoding, or the like can be employed before processing. As a result, some of the data and/or redundancy data may not explicitly appear in a sequence read, but the resulting nucleotide symbol string can be derived from the read.

In practice, reads can include additional information beyond simply the string of nucleotide symbols. For example, quality information or a confidence score can be included.

Example 14—Example Solitary-Strand-Based Processing

In any of the examples herein, solitary-strand-based processing can take the form of seriatim processing, where the nucleotide strand sequence reads from a polynucleotide sequencer are processed on a strand-by-strand (e.g., string-by-string) basis. In such a case, the strings are processed individually (e.g., the strand can be placed in the map without reference to other strands). As described herein, solitary-strand-based processing can place a string in the map based on having passed integrity verification without reference to other strands.

Such processing is in contrast to cluster-based processing, where a plurality of strands is evaluated in a cluster for placement of a reconstructed nucleotide symbol string.

In some solitary-strand-based cases, two strings may end up being assigned to a same position. If the strings match, there is no conflict. If they do not match, both can be removed from the map and processed as part of cluster-based trace reconstruction instead. Thus, a string may ultimately be moved out of the map due to subsequent processing.

Although the terms "seriatim" and "one-by-one" are used, it does not mean that all reads are processed. In some cases, strands can be omitted or skipped (e.g., if of an unacceptable length, etc.).

Some solitary-strand-based processing can be performed in parallel (e.g., one thread or process can process a portion of the reads, while another thread or process processes another portion of the reads).

Figure 5:
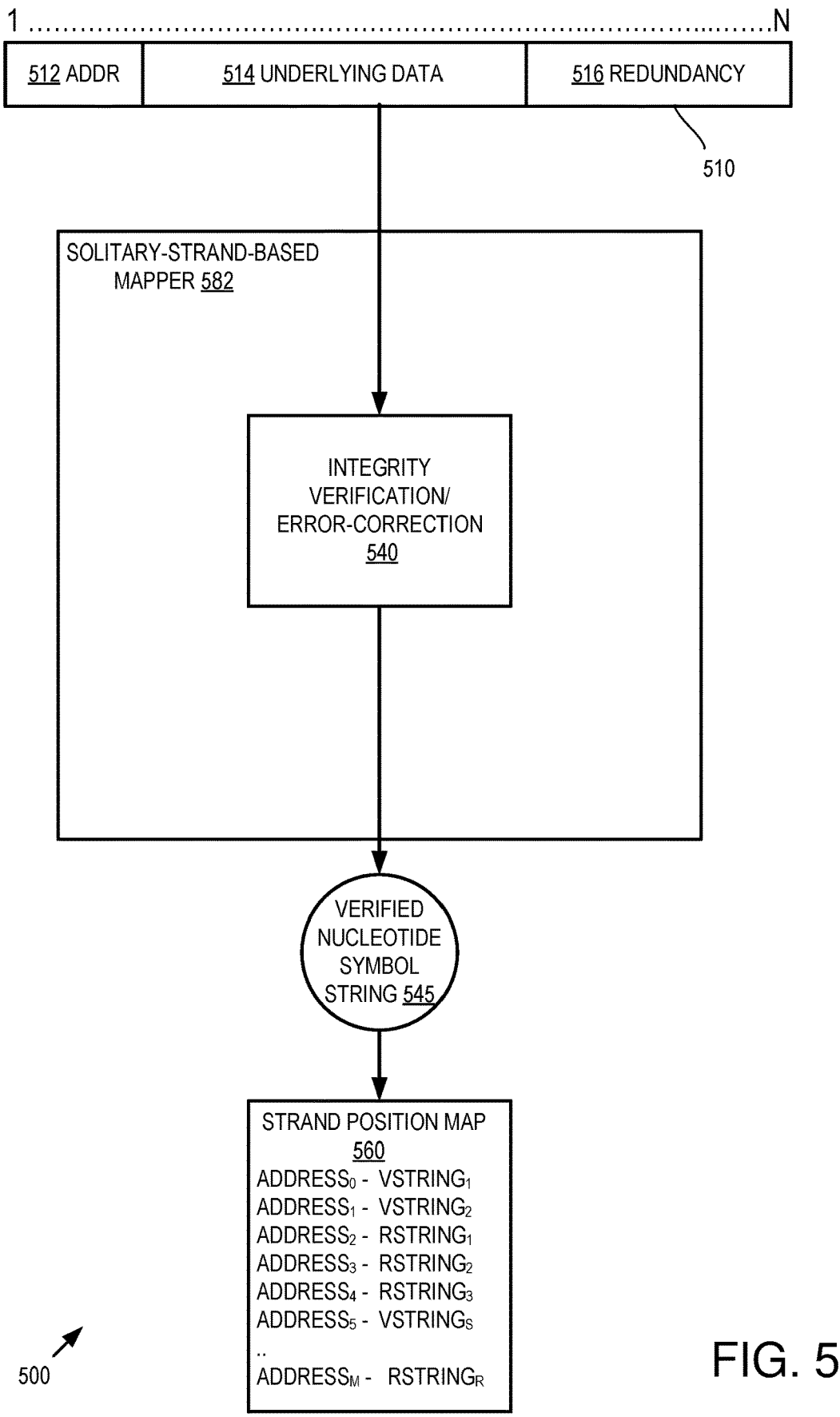
FIG. 5 is a block diagram of an example system implementing solitary-strand-based position selection.

Example 15—Example System Implementing Integrity-Verification-Based Position Selection FIG. 5 is a block diagram of an example system 500 implementing solitary-strand-based position selection. Such a system can be included in any of the decoding examples described herein (e.g., the system of FIG. 3).

In the example, an solitary incoming nucleotide symbol string 510 representing a solitary nucleotide strand sequence read from a polynucleotide sequencer is received by the solitary-strand-based mapper 582. In practice, a decoder can cycle through the incoming sequence reads seriatim (e.g., one-by-one), processing them in turn.

As shown, the string 510 can include data derived from the associated nucleotide strand sequence read such as the address 512, underlying data 514, and redundancy symbols 516. The redundancy symbols 516 can include inner redundancy symbols as described herein.

The mapper 582 can apply integrity verification and/or error-correction 540 to the incoming string 510. In practice, the redundancy information 516 can be applied to the rest of the string to determine whether it passes integrity verification. As described herein, the redundancy information 516 can also include error-correction information to correct one or more errors in the rest of the string.

The mapper 582 can then output a verified nucleotide symbol string 545, which typically also includes address information so that it can be placed in its proper place in the map 560.

Example 16—Example Method of Solitary-Strand-Based Position Selection

Figure 6:
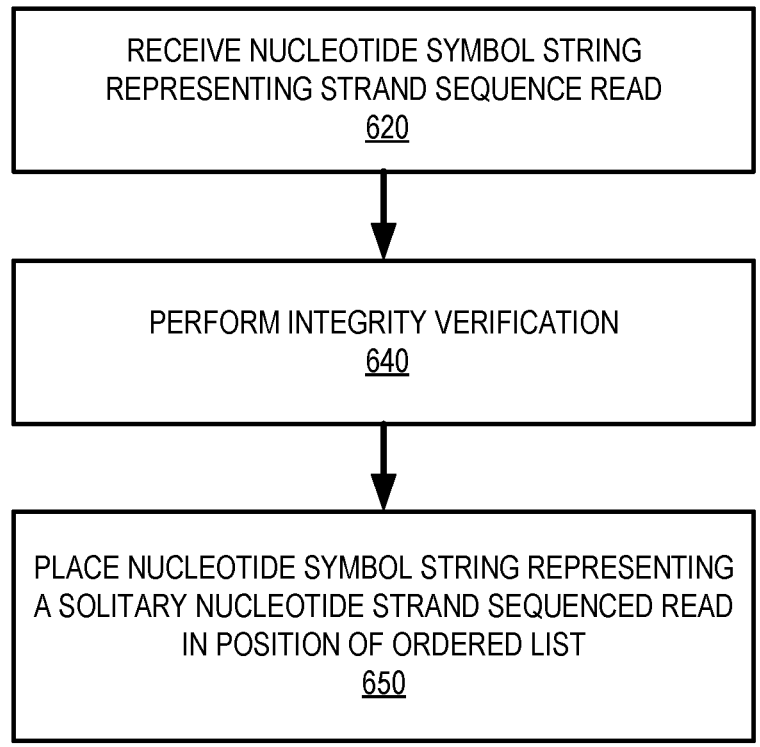
FIG. 6 is a flowchart of an example method of solitary-strand-based position selection.

FIG. 6 is a flowchart of an example method 600 of solitary-strand-based position selection that can be used in any of the examples herein for decoding and can be performed, for example, by the mapper of FIG. 5.

At 620, a nucleotide symbol string representing a strand sequence read is received.

At 640, integrity verification is performed on the string. In many cases, integrity verification will fail, and the string will not be placed. Instead, it can continue to be processed during cluster-based trace reconstruction as described herein.

However, in other cases, the nucleotide symbol string that represents a solitary nucleotide strand sequence read will be placed 650 in an order position of an ordered string map (e.g., responsive to determining that it passes integrity verification).

In practice, the method 600 can be repeated to process the incoming reads seriatim (e.g., one-by-one), processing them in turn one at a time.

As implemented, the solitary-strand-based selection can include variations. For example, a voting system can be used, and the strand receiving the greatest number of votes is placed. Votes can be weighted based on whether any errors are corrected (e.g., uncorrected strings get a greater vote). Alternatively, any conflicts can be deferred to processing at the cluster-based trace reconstruction phase.

Example 17—Example Redundancy Partitioning System

Figure 7:
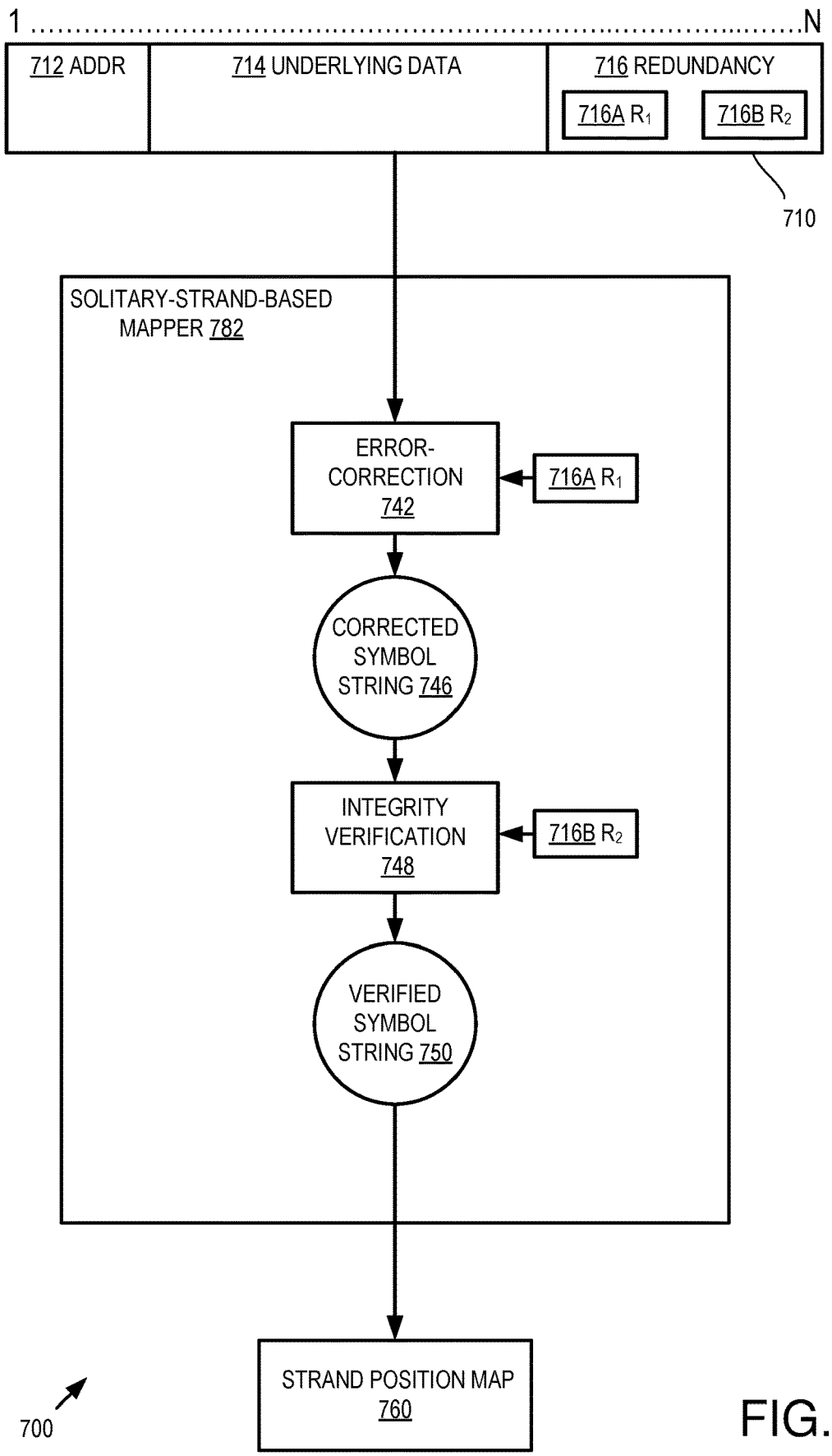
FIG. 7 is a block diagram of an example system implementing solitary-strand-based position selection with partitioned inner redundancy.

FIG. 7 is a block diagram of an example system 700 implementing solitary-strand-based position selection with partitioned inner redundancy that can be used for decoding in any of the examples herein. The system 700 can operate as an enhancement to that of FIG. 5 and can also accept a nucleotide symbol string 710 representing a solitary nucleotide strand sequence read from a polynucleotide sequencer as input. In practice, a decoder can cycle through the incoming sequence reads seriatim (e.g., one-by-one), processing them in turn.

As shown, the string 710 can include data derived from the associated nucleotide strand sequence read such as the address 712, underlying data 714, and redundancy symbols 716.

The redundancy symbols 716 can include inner redundancy symbols as described herein. In the example, the inner redundancy symbols are partitioned between at least two portions 716A and 716B. As described herein, one portion can be encoded at encode time to correct one or more substitution errors of the string, and another portion can be encoded to correct one or more deletion or insertion errors of the string.

The mapper 782 can apply integrity verification and/or error-correction 742 to the incoming string 710 as appropriate. In practice, a first portion 716A of the inner redundancy symbols can be used for error correction 742 to produce a corrected symbol string 746, to which integrity verification 748 then takes as input along with a second portion 716B of the inner redundancy symbols to output a verified symbol string 750. In practice, the corrected symbol string 746 can itself be the verified symbol string 750 (e.g., a new string need not be created).

The mapper 782 can then output the corrected, verified nucleotide symbol string 750, which typically also includes address information so that it can be placed in its proper place in the map 760.

Example 18—Example Redundancy Partitioning Method

Figure 8:
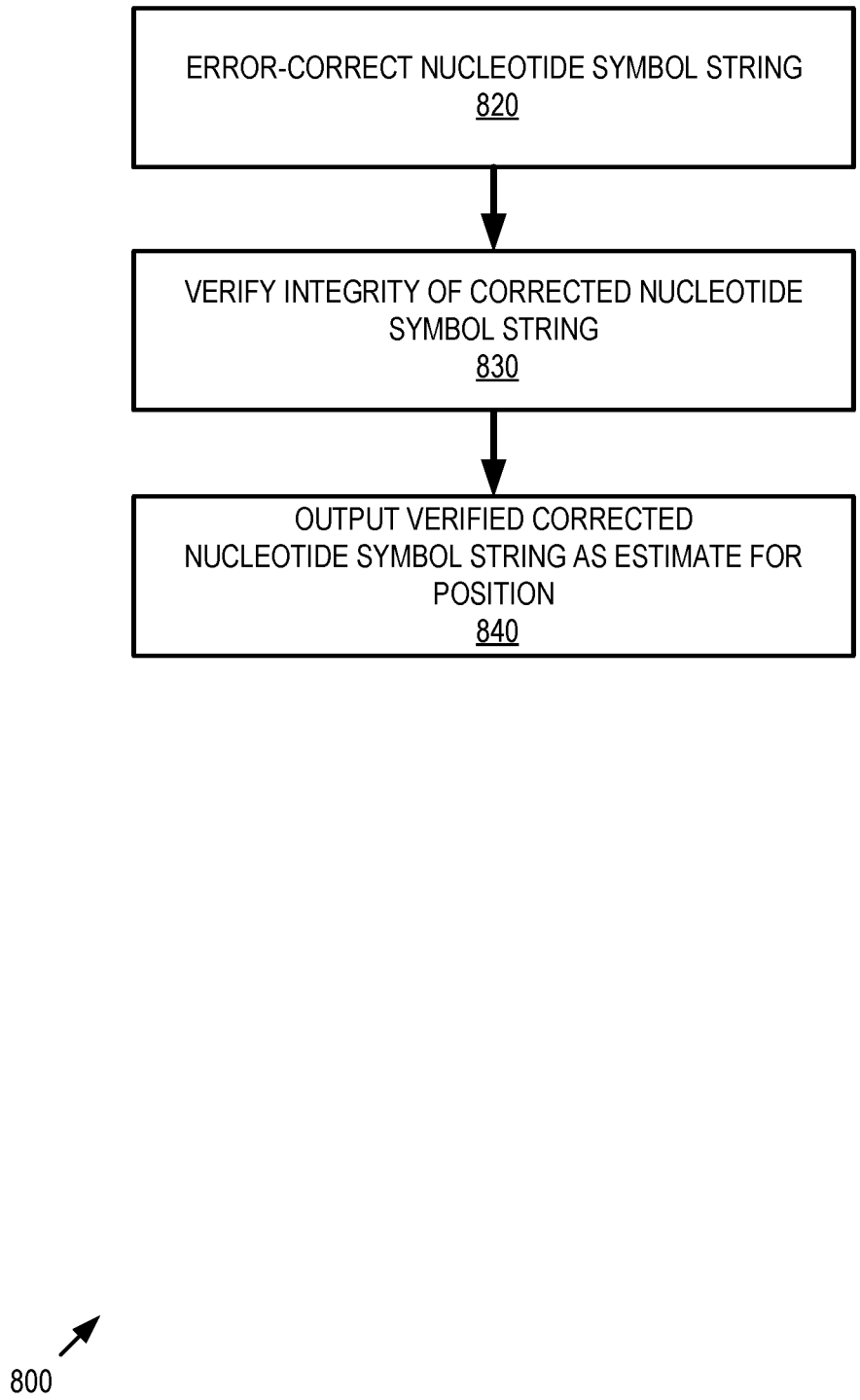
FIG. 8 is a flowchart of an example method of solitary-strand-based position selection with partitioned inner redundancy.

FIG. 8 is a flowchart of an example method 800 of solitary-strand-based position selection with partitioned redundancy that can be used for decoding in any of the examples herein and can be performed, for example, by the mapper 782 of FIG. 7. The method 800 can be performed on a received nucleotide symbol string representing a strand sequence read.

At 820, the received nucleotide symbol string is error-corrected using a first portion of inner redundancy symbols.

At 830, the integrity of the corrected nucleotide symbol string can be verified using a second portion of inner redundancy symbols.

At 840, the verified, corrected nucleotide symbol string can be output as an estimate for the position indicated in its address.

In a situation where the redundancy symbols are partitioned into a portion for correcting one or more substitution errors and a portion for correcting one or more insertion or deletion errors, one portion can be used to correct the string, and the remaining portion can be used to verify integrity of the string.

Example 19—Example Decoding Compatibility

The decoding examples herein can be used to decode data that is encoded on nucleotide strands with legacy encodings having inner redundancy information. In some cases, additional redundancy information can be included to support error correction in combination with verification.

Example 20—Example Filtering for Solitary-Strand-Based Position Selection

In any of the examples herein, a layer of filtering can be applied to solitary-strand-based position selection based on string length. In cases where the string length is outside the limit of what can be corrected via inner redundancy information included in the string, the string can be discarded for further processing.

The original string length can be determined in a variety of ways. For example, a fixed length can be used. In practice, the fixed length can be known by convention or stored as metadata for the file.

Thus, only strings falling within a correctable range (e.g., the fixed length plus or minus the number errors corrected by insertion/deletion redundancy information) are considered for placement. Thus, the string is processed further during solitary-strand-based position selection responsive to determining that the string length falls inside a correctable range (e.g., whether it is exactly the original length or somewhat longer or shorter, depending on the number of insertion/deletion errors that can be corrected). Conversely, responsive to determining that the string length is outside of a correctable range, the string can be discarded from solitary-strand-based position selection.

Example 21—Example Cluster-Based Trace Reconstruction System

Figure 9:
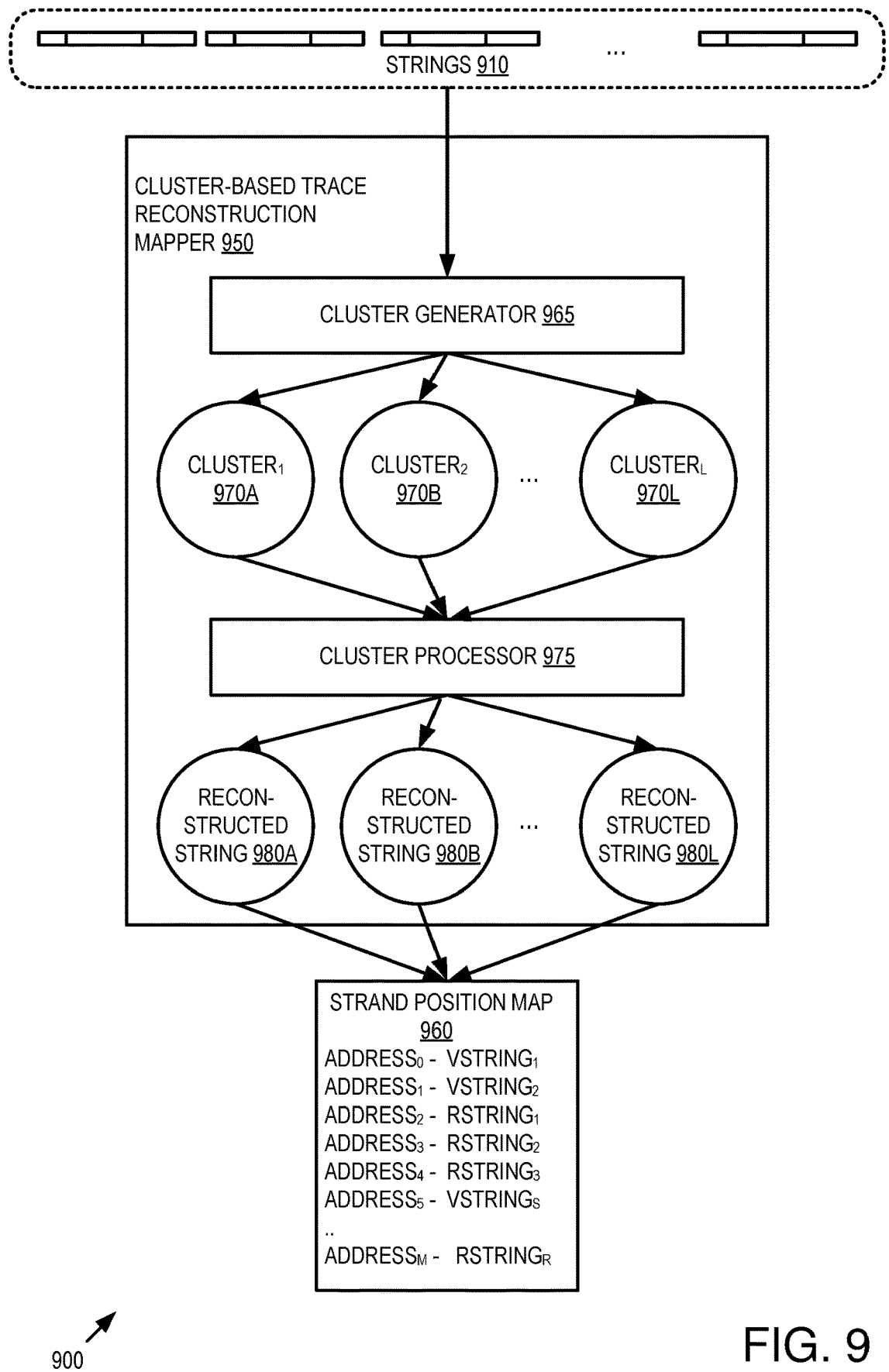
FIG. 9 is a block diagram of an example system implementing cluster-based trace reconstruction.

FIG. 9 is a block diagram of an example system 900 implementing cluster-based trace reconstruction that can be used for decoding in any of the examples herein. Such a system can be included in any of the decoding examples described herein (e.g., the system of FIG. 3).

In the example, the strings 910 representing nucleotide strand sequence reads from a polynucleotide sequencer are accepted as input by the cluster-based trace reconstruction mapper 950. As described herein, the reads represent logically ordered nucleotide symbol strings comprising encoded data with redundancy information.

The strings 910 can be similar to those elsewhere herein and include data derived from the associated nucleotide strand sequence read, such as an address, underlying data, and redundancy symbols.

The mapper 950 can first employ a cluster generator 965 that organizes the strings 910 into clusters 970A-L as described herein (e.g., cluster formation). The cluster processor 975 can then output reconstructed nucleotide symbol strings 980A-L based on the respective clusters. In some cases, an output string may not be possible or desired. For example, there may be insufficient data or insufficient quality of data to reconstruct a string for a particular cluster.

Example 22—Example Cluster-Based Trace Reconstruction Method

Figure 10:
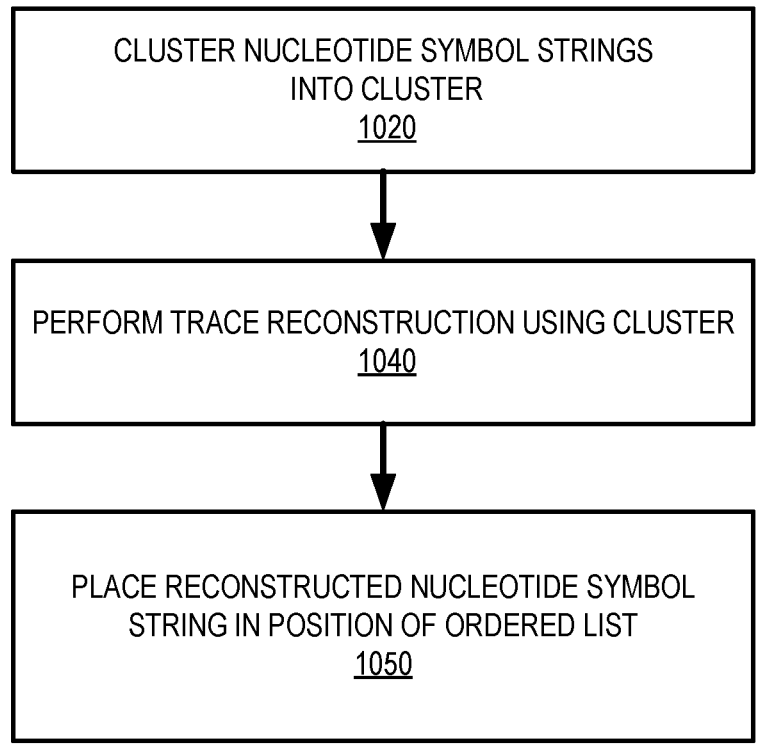
FIG. 10 is a flowchart of an example method of cluster-based trace reconstruction.

FIG. 10 is flowchart of an example method 1000 of cluster-based trace reconstruction that can be used for decoding in any of the examples herein and can be performed, for example, by the mapper 950 shown in FIG. 9.

The method can take nucleotide symbol strings representing strand sequence reads of encoded data embodied in nucleotide strands as input.

At 1020, the nucleotide symbol strings are organized into respective clusters during cluster formation. Various techniques can be used as described herein.

At 1040, cluster-based trace reconstruction using the cluster is performed as described herein. Such trace reconstruction yields an output reconstructed nucleotide symbol string that represents an estimate of the original strand based on strings in the cluster.

At 1050, the reconstructed nucleotide symbol string is placed in a position of the ordered list. An address in the reconstructed string indicates the position in which it is to be placed.

1040 and 1050 can be implemented for respective clusters. For example, the clusters can be processed individually. In practice, parallel processing of the clusters (e.g., after formation) can be performed.

In some cases, an output string may not be possible or desired. For example, there may be insufficient data or insufficient quality of data to reconstruct a string for a cluster. In other cases, it may be that the cluster can be eliminated from consideration (e.g., based on presence of a previously placed string in the cluster).

Example 23—Example Harmony and Conflict Between Solitary-Strand-Based Placement and Cluster-Based Trace Reconstruction As described herein, a single system can implement both solitary-strand-based placement and cluster-based trace reconstruction.

In some cases, it may be possible to save work by deferring to one of the techniques. For example, the system can omit processing of clusters with strings placed by solitary-strand-based placement from consideration. Or, cluster processing can still be carried out to confirm the string. Or, the system can omit processing of such clusters, depending on data quality and/or whether any correction was done on the placed string.

If both are done and the strings conflict, placement can defer to the solitary-strand-based placement, depending again on data quality and/or whether any correction was performed on the placed string.

In a solitary-strand-based technique, it can happen that two different strings appear to belong in the same position (e.g., both pass integrity verification). In such a case, if the strings do not match, decoding can defer placement to the cluster-based trace reconstruction process.

Although it may seem sensible to remove any strings placed by the solitary-strand-based placement from the incoming strings processed by cluster-based trace reconstruction, such strings can instead be left in the pool, thereby influencing the cluster formation and decoding process in a positive way.

Example 24—Example Result Scenarios

Cluster-based processing can be quite powerful. However, a particular scenario in which flexible decoding can be useful is in situations where a cluster-based approach is unable to reconstruct the correct string, but at least one of the incoming reads has the correct string. In such a case, the solitary-strand-based placement will place the correct string in the map, thus being superior to the cluster-based approach.

Example sequencing data is shown in Table 1, where each line corresponds to analyzing 1,000 clusters of appropriate size.

TABLE 1

Nanopore Sequenced Data

| Cluster size | Correct TR | (correct TR) or (has correct read) | (correct TR) or (has correct read within ED = 1) |
|---|---|---|---|
| 5 | 374 | 461 | 570 |
| 10 | 757 | 794 | 815 |
| 15 | 842 | 852 | 857 |
| 20 | 851 | 858 | 861 |

As shown in the table, there are a number of situations where the cluster-based approach does get the correct result ("Correct TR"=374), but there are additional situations where there is at least one correct read ("(correct TR) or (has correct read)"). There are even more situations where there is a correct read within an edit distance of 1. Therefore, a flexible-based approach can increase the overall success as compared to a cluster-only based approach in reconstructing and decoding incoming reads. Adding in error correction during solitary-strand-based processing as described herein can further expand the success of the approach.

Another way to evaluate sequencing data is to focus on the Hamming distance (e.g., the number of symbols that are in error) between the output of cluster-based trace reconstruction and a correct strand, which is a relevant metric for decoder performance. Table 2 shows a sample of 1,000 clusters of appropriate sizes, for which were computed "TR" (the sum, where each cluster contributed the Hamming distance between the output of trace reconstruction and the correct strand); "(TR) or (correct read)" (the sum, where each cluster contributes the Hamming distance between the output of trace reconstruction and the correct strand or zero if there is a correct read; and "(TR) or (read within ED=1)" the sum, where each cluster contributes the Hamming distance between the output of trace reconstruction and the correct strand or zero if there is a read within edit distance at most one. Smaller numbers are effectively better because the Hamming distance is less (e.g., the strings are more correct).

TABLE 2

| | Nanopore Sequenced Data | | |
|---|---|---|---|
| Cluster size | TR | (TR) or (correct read) | (TR) or (read within ED = 1) |
| 5 | 16,075 | 14,413 | 12,482 |
| 10 | 4,719 | 4,072 | 3,928 |
| 15 | 3,079 | 2,924 | 2,919 |
| 20 | 2,830 | 2,714 | 2,711 |

Thus, again, it is demonstrated that including solitary-strand-based placement of strings increases the performance of the decoder. And, error correction during solitary-strand-based placement can further include performance.

Example 25—Example Trace Reconstruction

The trace reconstruction problem may be set out using mathematical notation as follows. Let $\Sigma$ denote a finite alphabet, for instance, $\Sigma=\{A, C, G, T\}$. Let $X \in \Sigma^n$ be a sequence of interest, which can be arbitrary or random. The goal is to reconstruct the sequence of the DNA strand X exactly from a collection of noisy reads.

Some sequencing technologies such as sequencing-by-synthesis (discussed more below) have an error profile in which the noise is distributed independently at least to a degree. Thus, the noise can be modeled as independent and identically distributed (i.i.d.) throughout the strands. This type of noise can be created with synthetic test data. To do so, let $Y_1, Y_2, \ldots, Y_m$ be i.i.d. sequences obtained from X in the following way. Let $p_d$, $p_i$, and $p_s$ denote deletion, insertion, and substitution probabilities, respectively, such that $p=p_d+p_i+p_s \in [0,1]$. To obtain a noisy read Y, start with an empty string, and for a position of comparison $j=1, 2, \ldots, n$, do the following:

(no error) with probability 1−p, copy X[j] to the end of Y and increase j by 1;

(deletion) with probability $p_d$, increase j by 1;

(insertion) with probability $p_i$, copy X[j] to the end of Y, add a random symbol at the end of Y, and increase j by 1;

(substitution) with probability $p_s$, add a random symbol at the end of Y and increase j by 1.

Other sequencing technologies such as nanopore sequencing (discussed more below) have a different error profile in which the errors are not independently distributed but tend to be clustered so that if one error is present it is more likely that other errors are nearby. Nanopore sequencing has more errors than sequencing-by-synthesis. About 12% as compared to about 1-2%. This can create "bursts" of errors in the string by creating a localized high-error region. In addition to single position errors, nanopore sequencing results may have larger errors such as transposition of neighboring blocks of bases.

Identifying a single consensus sequence from a plurality of noisy reads—trace reconstruction—outputs an estimate read X which is the estimate for the true sequence X of the DNA strand. The estimate is created from a number m of noisy reads Y. Thus, $\hat{X}=\hat{X}(Y_1, Y_2, \ldots, Y_m)$. The goal is to exactly reconstruct X, i.e., to minimize $P(\hat{X} \neq X)$ Minimizing the probability that $\hat{X}$ is different from X may be done by using as many parts of the noisy reads Y while accounting for or ignoring errors in the noisy reads.

Figure 11:
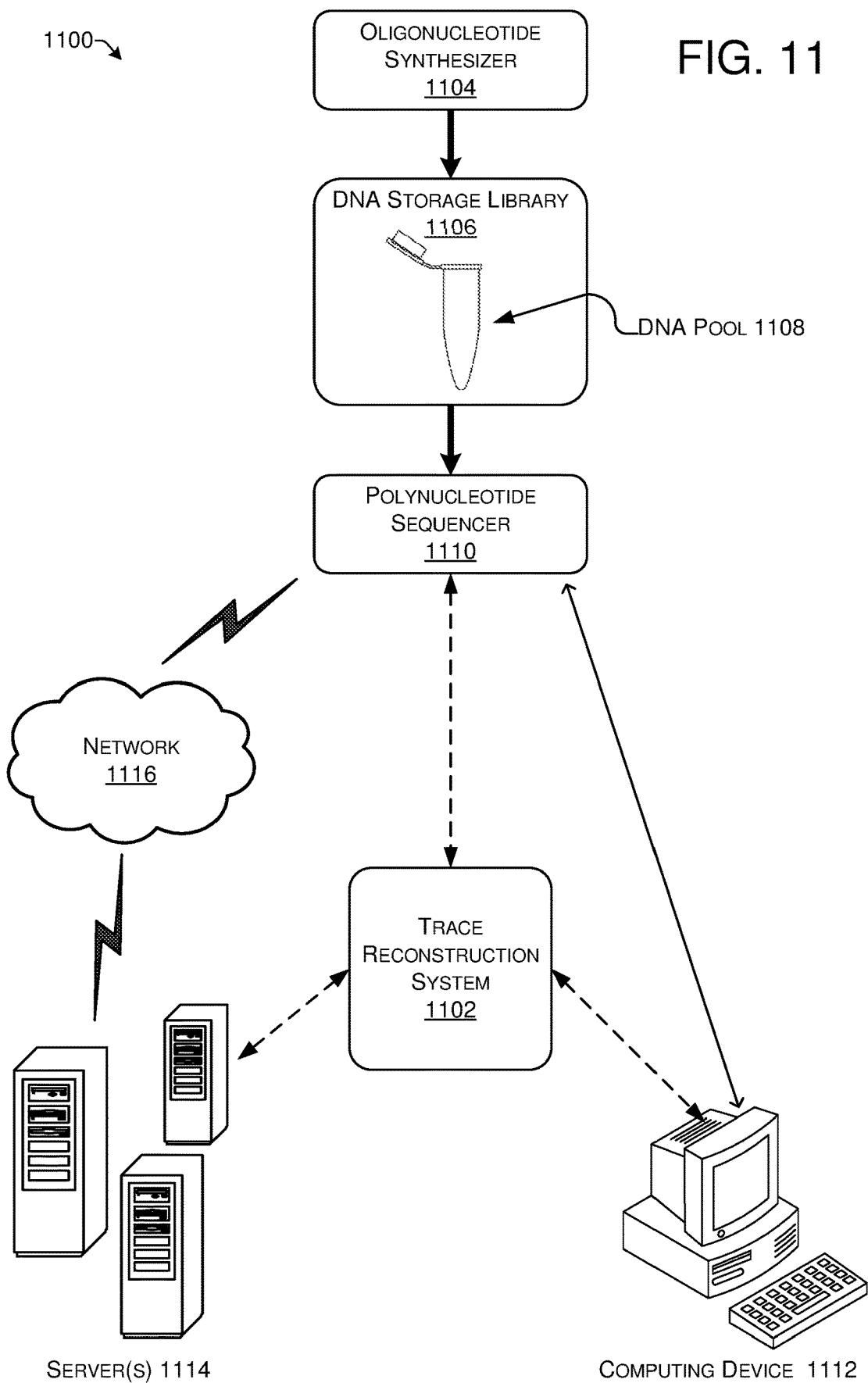
FIG. 11 shows an illustrative architecture for operation of a trace reconstruction system.

FIG. 11 shows an illustrative architecture 1100 for implementing a trace reconstruction system 1102. Briefly, digital information that is intended for storage as DNA molecules is converted into information representing a string of nucleotides. The information representing the string of nucleotides (i.e., a string of letters representing an order of nucleotide bases) is used as DNA-synthesis templates that instruct an oligonucleotide synthesizer 1104 to chemically synthesize a DNA molecule nucleotide by nucleotide. Artificial synthesis of DNA allows for creation of synthetic DNA molecules with arbitrary series of the bases in which individual monomers of the bases are assembled together into a polymer of nucleotides. The oligonucleotide synthesizer 1104 may be any oligonucleotide synthesizer using any recognized technique for DNA synthesis. The term "oligonucleotide" as used herein is defined as a molecule including two or more nucleotides.

The coupling efficiency of a synthesis process is the probability that a nucleotide binds to an existing partial strand at each step of the process. Although the coupling efficiency for each step can be higher than 99%, this small error still results in an exponential decrease of product yield with increasing length and limits the size of oligonucleotides that can be efficiently synthesized at present to about 200 nucleotides. Therefore, the length of the DNA strands put into storage is around 100 to 200 base pairs (bp). This length will increase with advances in oligonucleotide synthesis technology.

The synthetic DNA produced by the oligonucleotide synthesizer 1104 may be transferred to a DNA storage library 1106. There are many possible ways to structure a DNA storage library 1106. In addition to structure on the molecular level by appending identifying sequences to the DNA strands, a DNA storage library 1106 may be structured by physically separating DNA strands into one or more DNA pools 1108. Here the DNA pool 1108 is shown as a flip top tube representing a physical container for multiple DNA strands. DNA strands are generally most accessible for manipulation by bio-technological techniques when the DNA is stored in a liquid solution. Thus, the DNA pool 1108 can be implemented as a chamber filled with liquid, in many implementations water, and thousands, millions, or more individual DNA molecules may be present in a DNA pool 1108.

Besides being in a liquid suspension, the DNA strands in the DNA storage library 1106 may be present in a glassy (or vitreous) state, as a lyophilized product, as part of a salt, adsorbed on the surface of a nanoparticle, or another format. The structure of the DNA pools 108 may be implemented as any type of mechanical, biological, or chemical arrangement that holds a volume of liquid including DNA to a physical location. Storage may also be in a non-liquid form such as a solid bead or by encapsulation. For example, a single flat surface having a droplet present thereon, with the droplet held in part by surface tension of the liquid, even though not fully enclosed within a container, is one implementation of a DNA pool 1108. The DNA pool 1108 may include single-stranded DNA (ssDNA), double-stranded DNA (dsDNA), single-stranded RNA (ssRNA), double-stranded RNA (dsRNA), DNA-RNA hybrid strands, or any combination including use of unnatural bases.

DNA strands removed from the DNA storage library 1106 may be sequenced with a polynucleotide sequencer 1110. In some implementations, DNA strands may be prepared for sequencing by amplification using polymerase chain reaction (PCR) to create a large number of DNA strands that are identical copies of each other. The need for PCR amplification prior to sequencing may depend on the specific sequencing technology used. PCR may itself be a source of error, although at a much lower level than current sequencing technology. At present, PCR techniques typically introduce approximately one error per 10,000 bases. Thus, on average, for every 100 reads of 100 bases there will be one error that is the result of PCR. The errors introduced by PCR are generally distributed randomly so the trace reconstruction system is able to correct some PCR-induced errors.

As mentioned above, the polynucleotide sequencer 1110 reads the order of nucleotide bases in a DNA strand and generates one or more reads from that strand. Polynucleotide sequencers 1110 use a variety of techniques to interpret molecular information and may introduce errors into the data in both systematic and random ways. Errors can usually be categorized as substitution errors, where the real nucleotide is substituted with an incorrect base call (for example A swapping with G), insertions, or deletions, where a random base call is inserted (for example AGT becoming AGCT) or deleted (for example AGTA becoming ATA). Transpositions, which are swapping of longer regions of DNA, are another type of error. Each position in a read is an individual base call determined by the polynucleotide sequencer 1110 based on properties sensed by components of the polynucleotide sequencer 1110. The various properties sensed by the polynucleotide sequencer 1110 vary depending on the specific sequencing technology used. A base call represents a determination of which of the four nucleotide bases—A, G, C, and T (or U)—in a strand of DNA (or RNA) is present at a given position in the strand. Sometimes the base calls are wrong, and this is a source of error introduced by sequencing. Polynucleotide sequencing includes any method or technology that is used to generate base calls from a strand of DNA or RNA.

A sequencing technology that can be used is sequencing-by-synthesis sequencing by Illumina, Inc. of San Diego, Calif. The Sequencing-by-synthesis technology is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double-stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used is Nanopore sequencing. A nanopore is a small hole of the order of 1 nanometer in diameter Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Other sequencing technologies that are currently known include single molecule, real-time (SMRT™) technology from Pacific Biosciences, Helicos True Single Molecule Sequencing (tSMS), SOLiD™ technology available from Applied Biosystems, use of a chemical-sensitive field effect transistor (chemFET) array, and use of an electron microscope to read a sequence of nucleotide bases.

All technologies for sequencing DNA are associated with some level of error and the type and frequency of errors differ by sequencing technology. For example, sequencing-by-synthesis creates an error in about 2% of the base calls and the errors tend to be independently and identically distributed (i.i.d.). A majority of these errors are substitution errors. Nanopore sequencing has a much higher error rate of about 15 to 40% and most of the errors caused by this sequencing technology are deletions. Errors in sequences generated by Nanopore sequencing tend to be present in clusters so if a position has an error it is more likely that adjacent positions will too. Thus, the errors may be thought of as coming in "bursts." The error profile of a specific sequencing technology may describe the overall frequency of errors, distribution characteristics of errors, as well as the relative frequency of various types of errors.

In some implementations, the polynucleotide sequencer 1110 provides quality information that indicates a level of confidence in the accuracy of a given base call. The quality information may indicate that there is a high level or a low level of confidence in a particular base call. For example, the quality information may be represented as a percentage, such as 80% confidence, in the accuracy of a base call. Additionally, quality information may be represented as a level of confidence that each of the four bases is the correct base call for a given position in a DNA strand. For example, quality information may indicate that there is 80% confidence the base call is a T, 18% confidence the base call is an A, 1% confidence the base call is a G, and 1% confidence the base call is a C. Thus, the result of this base call would be T because there is higher confidence in that nucleotide being the correct base call than in any of the other nucleotides. Quality information does not identify the source of an error but merely suggests which base calls are more or less likely to be accurate.

The polynucleotide sequencer 1110 provides output, multiple noisy reads (frequently of multiple DNA strands), in electronic format to the trace reconstruction system 102. The output may include the quality information as metadata for otherwise associated with the reads produced by the polynucleotide sequencer 1110.

The trace reconstruction system 1102 may be implemented as an integral part of the polynucleotide sequencer 1110. The polynucleotide sequencer 1110 may include an onboard computer that implements the trace reconstruction system 1102. Alternatively, the trace reconstruction system 1102 may be implemented as part of a separate computing device 1112 that is directly connected to the polynucleotide sequencer 1110 through a wired or wireless connection which does not cross a network. For example, the computing device 1112 may be a desktop or notebook computer used to receive data from and/or to control the polynucleotide sequencer 1110. A wired connection may include one or more wires or cables physically connecting the computing device 1112 to the polynucleotide sequencer 1110. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. The trace reconstruction system 1102 may also be implemented as part of a cloud-based or network system using one or more servers 1114 that communicate with the polynucleotide sequencer 1110 via a network 1116. The network 1116 may be implemented as any type of communications network such as a local area network, a wide area network, a mesh network, an ad hoc network, a peer-to-peer network, the Internet, a cable network, a telephone network, and the like. Additionally, the trace reconstruction system 1102 may be implemented in part by any combination of the polynucleotide sequencer 1110, the computing device 1112, and the servers 1114.

Figure 12:
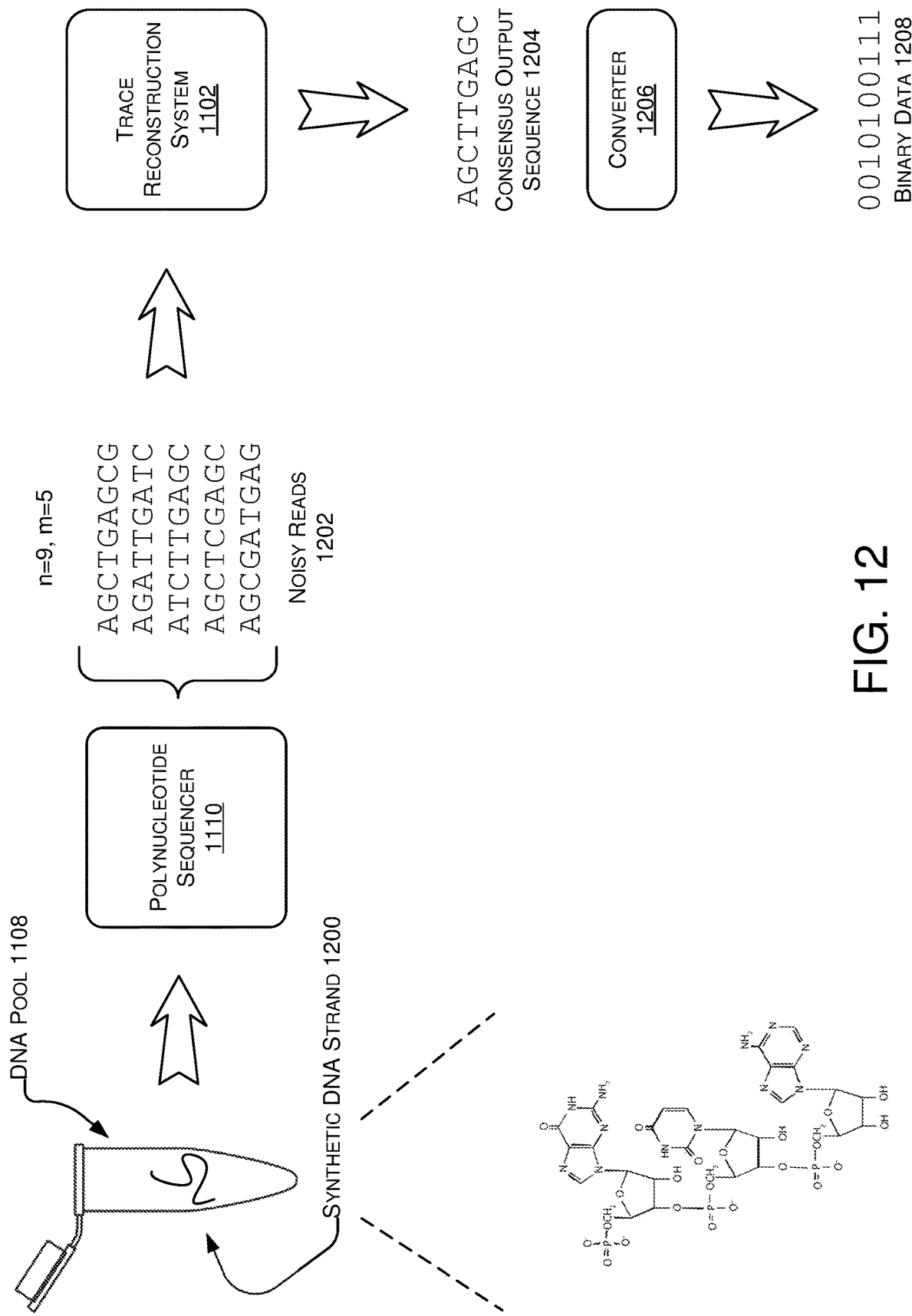
FIG. 12 is an illustrative schematic showing the use of a trace reconstruction system.

FIG. 12 shows the use of the trace reconstruction system 1202 as part of the process of decoding information stored in a synthetic DNA strand 1200. The synthetic DNA strand 1200 is a molecule having a specific sequence of nucleotide bases. The synthetic DNA strand 1200 may be stored in a DNA pool 1108 as shown in FIG. 11. The synthetic DNA strand 1200 may be present in the DNA pool 1108 as a single-stranded molecule or may hybridize to a complementary ssDNA molecule to form dsDNA. The polynucleotide sequencer 1110 produces an output of multiple noisy reads 1202 from the single synthetic DNA strand 1200. The number of reads is related to coverage depth of the sequencing. Greater depth of sequencing leads to on average more sequences generated from the DNA strand. Because of the errors in sequencing, it is likely that many of the multiple reads of the same DNA strand have different sequences. Each of the reads has a length (n) which in this example is nine corresponding to nine bases in the synthetic DNA strand 1200. In actual sequencer data the noisy reads may have arbitrary lengths that are not all equal to each other. Deletions and insertions are one cause of variation in read length. For a given read, that read's length may be denoted as n, but n is not necessarily the same for all reads. In actual implementations, the length of the reads is likely to be between 100 and 200 due to current limitations on the maximum length of DNA strands that can be artificially synthesized. Locations on a read may be referred to as "base positions" such as in this example going from position one to position nine. As used herein, "base" refers to a location of a given monomer in a DNA molecule while "base position" refers to a location along a string of data such as a read. Thus, assuming no errors, the third base in the synthetic DNA strand 200 corresponds to the third base position in a read generated by the polynucleotide sequencer 110.

The number (m) of noisy reads 1202 provided to the trace reconstruction system 102 is five in this example. However, any number may be used. In some implementations, the number of noisy reads 1202 provided to the trace reconstruction system 1102 may be 10, 20, or 100. The number of noisy reads 1202 provided to the trace reconstruction system 1102 may be less than the total number of reads produced by the polynucleotide sequencer 1110. A subset of the total number reads produced by the polynucleotide sequencer 1110 may be selected at random or using heuristics for analysis by the trace reconstruction system 1102. In addition to random selection, other techniques may be used for choosing which subset of reads are passed to the trace reconstruction system 1102. For example, quality information may be used to identify m reads having the highest confidence in the base calls from all of the reads generated by the polynucleotide sequencer 1110. In some implementations, only reads with certain lengths are selected.

The trace reconstruction system 1102 analyzes the noisy reads 1202 according to the techniques of this disclosure and generates a consensus output sequence 1204. The consensus output sequence 1204 represents the sequence of nucleotides in the synthetic DNA strand 1200 with less error than any of the individual noisy reads 1202 and ideally with no error.

A converter 1206 converts the consensus output sequence 1204 into binary data 1208, thereby retrieving the digital information stored in the DNA storage library 1106. The converter 1206 may use additional error correction techniques to correct any errors that may remain in the consensus output sequence 1204. Thus, it is not necessary for the trace reconstruction system 1102 to correct all types of errors because there are other error correction techniques that may be used to recover the binary data 1208.

Although the implementation discussed herein relates to obtaining binary data 1208 from reads of a synthetic DNA strand 1200, the trace reconstruction system 1102 can operate equally well on reads of natural DNA strands. The output from the polynucleotide sequencer 1110 is a plurality of noisy reads 1202 for both synthetic DNA and natural DNA. Thus, the trace reconstruction system 1102 may be used to remove errors from reads generated by the polynucleotide sequencer 1110 in implementations that do not involve the use of synthetic DNA to store binary data 1208.

Figure 13:
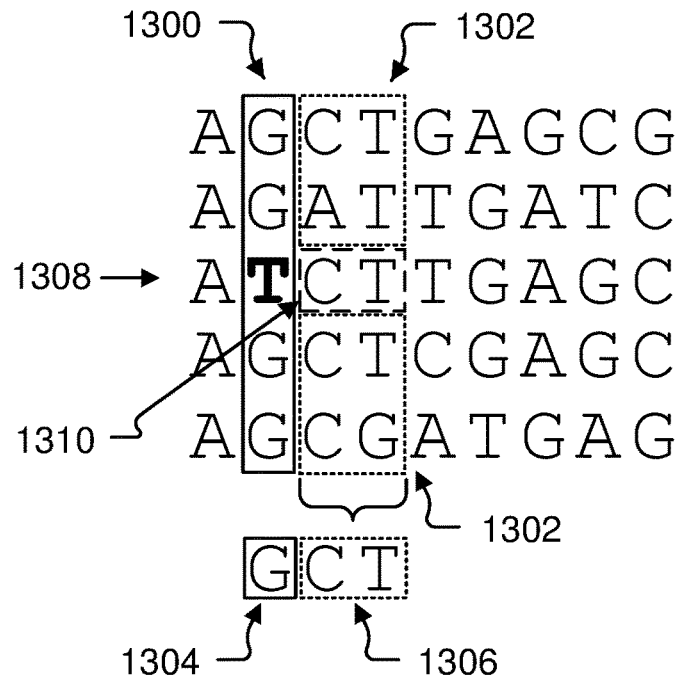
FIG. 13 shows an illustrative representation of an identified substitution error.
Figure 13:
Figure 13:
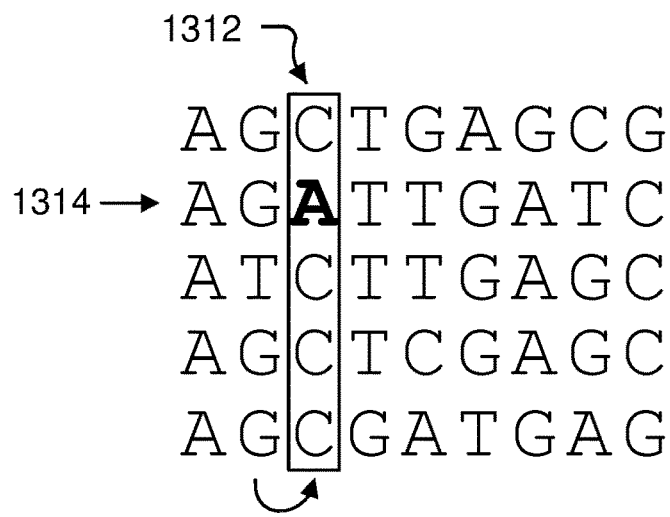

FIG. 13 shows a technique for identifying a substitution error. The reads may be aligned at a starting position or any other position such as an alignment anchor discussed in greater detail below. The starting position may correspond to the 5' end of the DNA strand that generated the read. In the figures of this disclosure the 5' end is oriented to the left. A position of comparison 1300 spanning the reads is represented by the solid rectangular box. The position of comparison 1300 may move along the reads from left to right as each position in the reads is analyzed in turn Immediately following the position of comparison 1300 is a look-ahead window 1302 represented by two dotted rectangular boxes. The look-ahead window 1302 "looks ahead" to the right, or towards the 3' end, of the position of comparison 1300. That is, if the read is represented as $Y_j$ and the position of comparison 1300 is represented as AA, then the look-ahead window 1302 of length w is the substring consisting of $Y_j[p[j]+1], \ldots Y_j[p[j]+w]$. The look-ahead window 1302 may move along the reads as the position of comparison 1300 moves. In this example, the length of the look-ahead window 1302 is two positions, but it may be longer such as three, four, or more.

A plurality consensus base 1304 is the most frequent base call at the position of comparison 1300. Here, four of the five reads have G at this position and one read has T. Because G is the most numerous base call, the plurality consensus base 1304 is G. In some implementations, the plurality consensus base 1304 may be determined by consideration of quality information for the respective base calls at the position of comparison 1300. Each base call in the position of comparison 1300 may be weighted based on associated quality information. For example, if there is 80% confidence that a given base call is a G then that may count as 0.8 G towards a determination of the plurality consensus base 1304 while 30% confidence that a given base call is C will count as 0.3 C towards the determination of the plurality consensus base 1304. Thus, the confidence of individual base calls may be considered in identifying the plurality consensus base 1304 for a given position of comparison 1300. Additionally, or alternatively, all base calls with quality information indicating a confidence in the base call less than a threshold level (e.g., 15%) may be omitted from the determination of the plurality consensus base 1304. If two, or more, different base calls are present with equal frequency, the plurality consensus base 1304 may be randomly selected from among them.

A read that has a base call at the position of comparison 1300 that differs from the plurality consensus base 1304 is referred to as a variant read. Thus, for variant read $Y_k$ the base call $Y_k[p[k]]$ does not agree with the plurality consensus base 1304. A variant read in this example is the third strand 1308. Out of any grouping of reads, when analyzed at a given position of comparison 1300, there may be zero, one, or more than one variant reads.

A look-ahead window consensus 1306 is determined from the look-ahead window 1302 in a similar manner as the plurality consensus base 1304. Determination of the look-ahead window consensus 1306 may also be influenced by quality information. The look-ahead window consensus 1306 may be based on base calls weighted by their respective confidence levels and/or by omitting base calls with confidence levels below a threshold. The look-ahead window consensus 1306 is determined by consideration of reads that are not variant reads for the position of comparison 1300. Thus, the look-ahead window 1302 is shown here as covering the non-variant reads but not covering the variant read 1308. In this example, the most common base call in the first position of the look-ahead window 1302 is C and the most common base call the second position of the look-ahead window 1302 is T. Thus, the look-ahead window consensus 1306 is a two-position string of the base calls: CT.

Next, the base calls in the look-ahead window 1310 of the variant read (CT) are compared to the look-ahead window consensus 1306 (CT). Because they match, the mismatch at the second position in the third read 1308 is classified as a substitution. In mathematical notation, if $Y_k[p[k]+1], \ldots Y_k[p[k]+w]$ agrees with the look-ahead window consensus, then classify the mismatch in $Y_k$ as a substitution. The plurality consensus base 1304 is used as the base call for that position in the consensus output sequence 1204.

After the type of error for the variant read is classified, the position of comparison 1300 is moved to continue analysis of the reads. The position of comparison 1300 is moved one base position to the right for each of the reads that are not variant reads. In this example, these are the first, second, fourth, and fifth reads. For variant reads in which the error type is classified as substitution, here that is the third read 1308, the position of comparison 1300 is also moved one position to the right. Thus, as shown in the lower portion of FIG. 13, the position of comparison 1300 is moved one base position to the right for the reads. The analysis repeats at this new position of comparison 1312 and in this iteration the second read 1314 is identified as a variant read.

Figure 14:
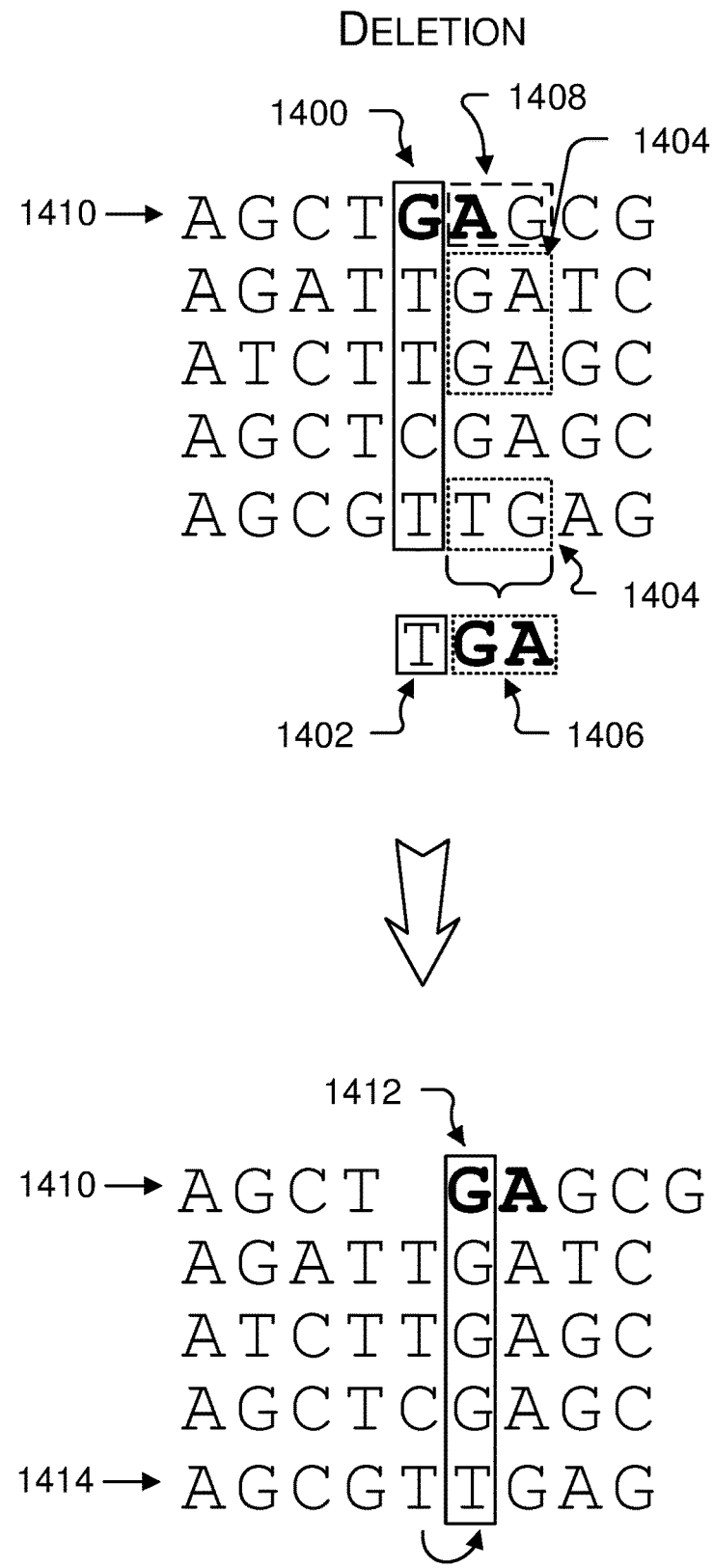
FIG. 14 shows an illustrative representation of an identified deletion error.

FIG. 14 shows a technique for identifying a deletion error. The position of comparison 1400 is again analyzed to determine the most frequent base call at that position. In this example, three of the five strands have the base call T, one strand has the base call G, and one strand has the base call C. Thus, the most common base call is T and the plurality consensus base 1402 for this position in the reads is T. The first strand 1410 and the fourth strand are identified as variant reads.

Base calls in the look-ahead window 1404 for the strands that are not variant reads are compared to determine a look-ahead window consensus 1406. In this example, the value of the two base calls in the look-ahead window 1404 for the three non-variant reads is GA, GA, and TG. The most common series of base calls is thus GA and this becomes the look-ahead window consensus 1406.

The value of the base calls in the look-ahead window 1408 (AG) for the first strand 410 is not the same as the look-ahead window consensus 1406 (GA). The type of error responsible for the mismatch in the first strand 1410 is therefore not classified as a substitution. However, the base calls in the position of comparison 1400 and all but the final position of the look-ahead window 1404 (GA) match the look-ahead window consensus 1406 (GA). Thus, the type of error for this position of the first strand 1410 is classified as a deletion. In this example, the length (w) of the look-ahead window 1404 is two, so all but the final position of the look-ahead window 1404 is w−1 or the first base of the look-ahead window 1404. If the look-ahead window 1404 has length (w) three, then the first two bases (3−1) of the look-ahead window 1404 would be considered when determining if the type of error in the variant read is a deletion. In mathematical notation, if $Y_k[p[k]], \ldots Y_k[p[k]+w-1]$ agrees with the look-ahead window consensus, then classify the mismatch in $Y_k$ as a deletion.

After the type of error for the variant read is classified, the position of comparison 1400 is moved one position to the right for each of the reads that are not variant reads and for each of the reads for which the error is classified as a substitution. For the first strand 1410 in which there is classified as a deletion, the position of comparison 1400 is not moved. It remains at the same G located in the fifth position of the first strand 1410. The deletion becomes evident as shown in the lower portion of FIG. 14 after realignment of the strands following the differential movement to a new position of comparison 1412 for the first strand 1410 (i.e., by zero) and for the other strands (i.e., by one). This realignment due to moving to the new position of comparison 1412 different amounts based on the classification of the error type keeps the strands in phase improving further analysis farther along the strands. After the new position of comparison 1412 is moved (or not depending on the error type) the analysis can repeat, here identifying a mismatch in the fifth strand 1414.

Figure 15:
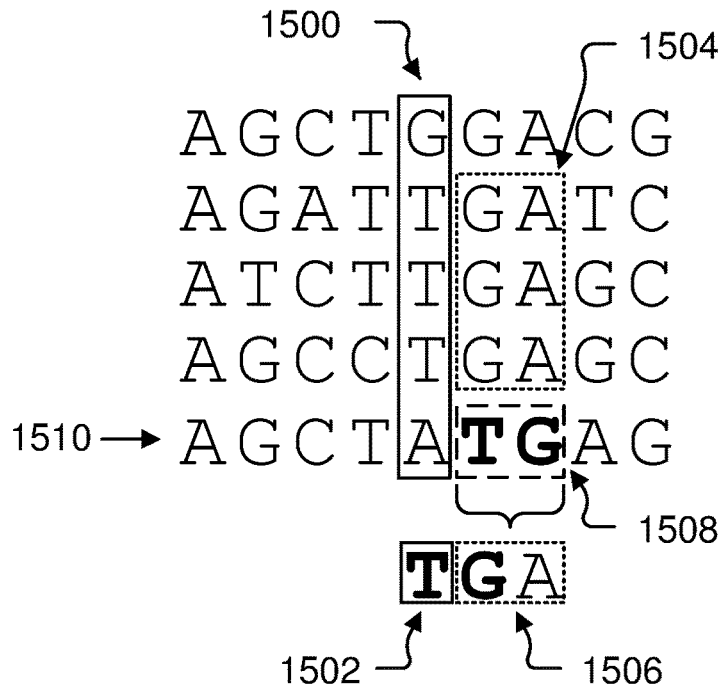
FIG. 15 shows an illustrative representation of an identified insertion error.
Figure 15:
Figure 15:
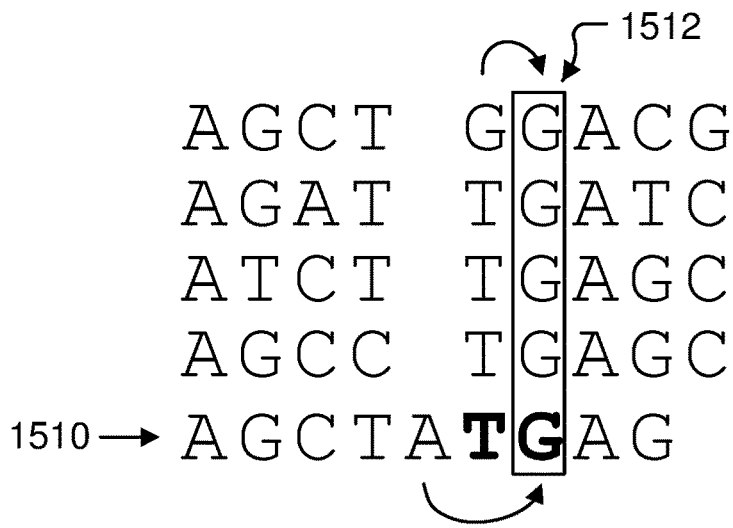

FIG. 15 shows a technique for identifying an insertion error. As discussed above, the three possible error types are substitution, deletion, and insertion. As with identification of substitution and deletion errors, identification of insertion errors begins with analyzing the base calls in a position of comparison 1500 to determine a plurality consensus base 1502 and analyzing base calls in a look-ahead window 1504 to identify a look-ahead window consensus 1506. In this example, the plurality consensus base 1502 is T. The fifth read 1510 is a variant read because it has an A rather than a T at the position of comparison 1500. The base calls for the look-ahead window consensus 1506 is GA. The base calls in the look-ahead window 1508 for the fifth read 1510 do not match the look-ahead window consensus 1506 so the error type is not classified as a substitution. The base call in the position of comparison 1500 and the first base call in the look-ahead window 1508 for the variant read (AT) do not match the look-ahead window consensus 1506 (GA) so the error type is not classified as a deletion.

However, the base calls in the look-ahead window 1508 of the fifth read 1510 match the base calls of the plurality consensus base 1502 and all but the final base call (i.e., w−1 positions) of the look-ahead window consensus 1506 (i.e., both are TG). Thus, the error is classified as insertion of an A at the $5^{th}$ position of the fifth read 1510. In mathematical notation, if $Y_k[p[k]+1]$ agrees with the plurality consensus base 1502, and $Y_k[p[k]+2], \ldots Y_k[p[k]+w]$ agrees with the first w−1 coordinates of the look-ahead window consensus 1506, then the mismatch in $Y_k$ is classified as an insertion. This insertion error becomes evident as shown in the lower portion of FIG. 15 after realignment of the strands following differential movement of the position of comparison 1500 to a new position of comparison 1512. The position of comparison 1500 is advanced two positions for the read that had the insertion, here that is the fifth read 1510. For the other strands, the position of comparison 1500 is advanced one position to the new position of comparison 1512 for reads that are not variant reads, one position for reads that have substitutions, and zero positions for reads that have deletion errors.

The examples shown in FIGS. 13-15 illustrate analysis of only one type of error each. However, the techniques of this disclosure are equally applicable to groups of reads that have multiple errors in one position of comparison. There may also be multiple error types across a single position of comparison, for example, out of a total of 20 reads (m=20) three reads could have substitutions, one read could have a deletion, and one read could have an insertion.

Figure 16:
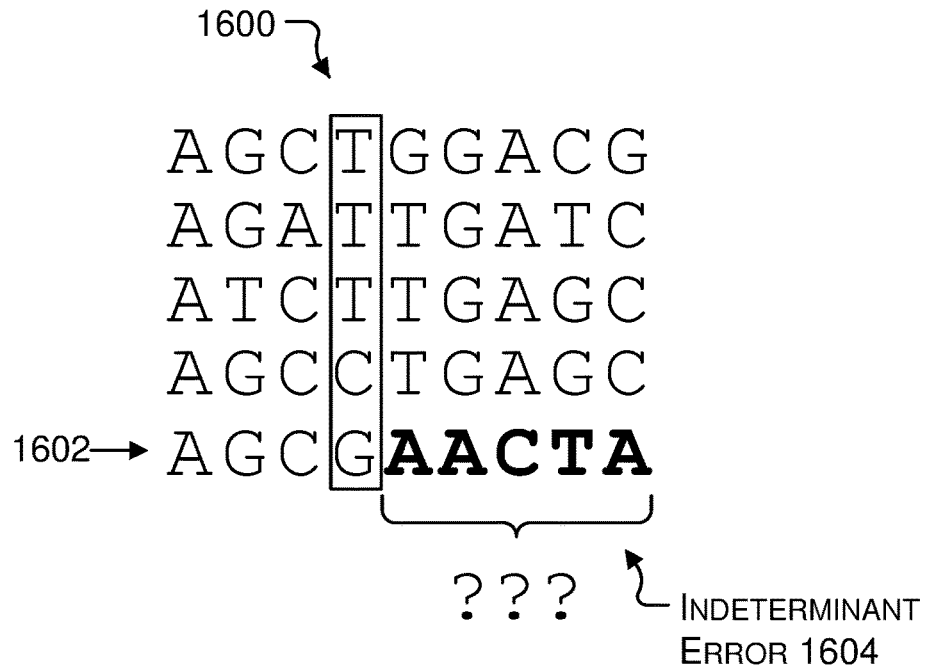
FIG. 16 shows an illustrative representation of an indeterminant error and inactive trace.
Figure 16:
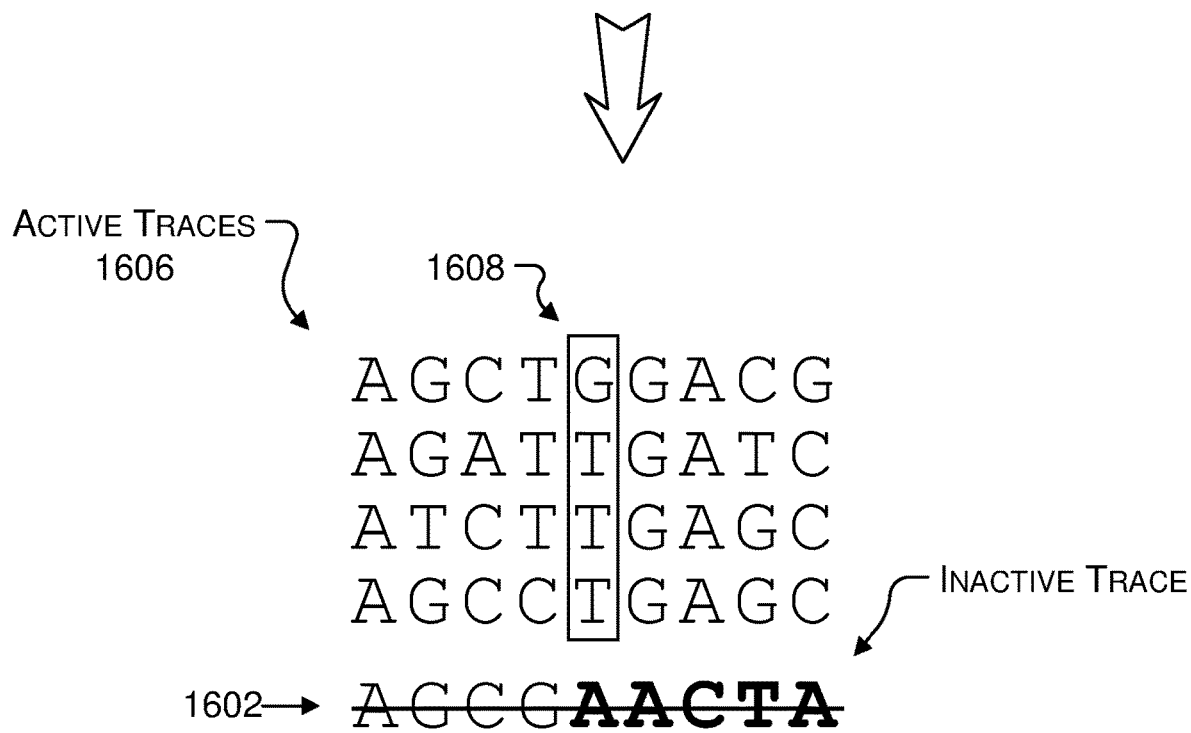

FIG. 16 illustrates a situation in which it is not possible to identify the type of error. A read may have a base call in the position of comparison that does not match the plurality consensus base call, thus it is a variant read, but the base calls in the position of comparison and the look-ahead window may not exhibit any of the relationships classified as substitution, deletion, or insertion. This is an error that cannot be classified according to the techniques described above, and thus, is referred to as an "indeterminant error" 1604. Even if other techniques are used for identifying the type of error besides those described in this disclosure, an error or a failure to match with the plurality consensus base call that cannot be resolved to a specific type of error can be classified as an indeterminate error.

Use of the techniques shown in FIGS. 13-15 cannot classify the base calls at the location of the indeterminant error 1604 in the fifth read 1602 as a substitution, an insertion, or a deletion. The position of comparison 1600 immediately prior to the location of the indeterminant error 1604 is the last position before the indeterminant error 1604.

One way of handling reads that have indeterminant errors is to discard the read from further processing. Thus, if a read has an error and it cannot be resolved to a single error type, that read is omitted from further analysis. If the read 1602 is discarded, it may be indicated as an "inactive trace" because the read 1602 does not contribute any information to trace reconstruction. Once the read 1602 is identified as an inactive trace, the consensus output sequence is generated from the remaining active traces 1606. The active traces 1606 may be all of the other reads from the same cluster or may be fewer than all the other reads if some are discarded for also including indeterminant errors, for low confidence levels, or otherwise.

However, completely discarding a read also discards useful information that may be contained in portions of the read that do not have indeterminant errors. For some sequencing technologies, such as Nanopore sequencing, discarding every read that has an indeterminant error can reduce the number of recovered clusters significantly, because this may even leave so few reads remaining that is not possible to perform trace reconstruction.

Another way of handling ambiguous errors is to use a bias or tiebreaker in order to force a classification. The bias may be based on an error profile of the polynucleotide sequencer used to generate the reads. For example, if the polynucleotide sequencer is known to generate substitution errors much more frequently than either deletion or insertion errors, all ambiguous errors could be classified as substitutions. If an error can be identified as one of two possible error types, the relative frequency of those error types for the polynucleotide sequencer technology may be used to choose between them. For example, if an error has been identified as either a deletion or insertion (but not a substitution) and the polynucleotide sequencer makes 80% substitution errors, 15% deletion errors, and 5% insertion errors, that error may be classified as a deletion error because deletion errors are more likely than insertion errors in this example. However, this may decrease the reliability of the consensus output sequence because base calls that are likely incorrect may be included in the calculation of the consensus base call.

Additionally, or alternatively, the quality information of individual base calls may be used to classify ambiguous errors. In one implementation, when an error is unable to be resolved to a single error type, all base calls in the position of comparison and the look-ahead window with quality information indicating a base call confidence of less than a threshold level may be omitted from the determination of the plurality consensus base and the look-ahead window consensus. Thus, the consensus base calls for the relevant positions are determined on the most reliable base calls from the multiple reads. Ignoring the low-confidence base calls may lead to the techniques described above being able to resolve the error to a single error type. If, however, the confidence level is low for most of the base calls or even if the confidence level is consistent then selecting specific base calls based on confidence levels may not yield accurate results.

Figure 17:
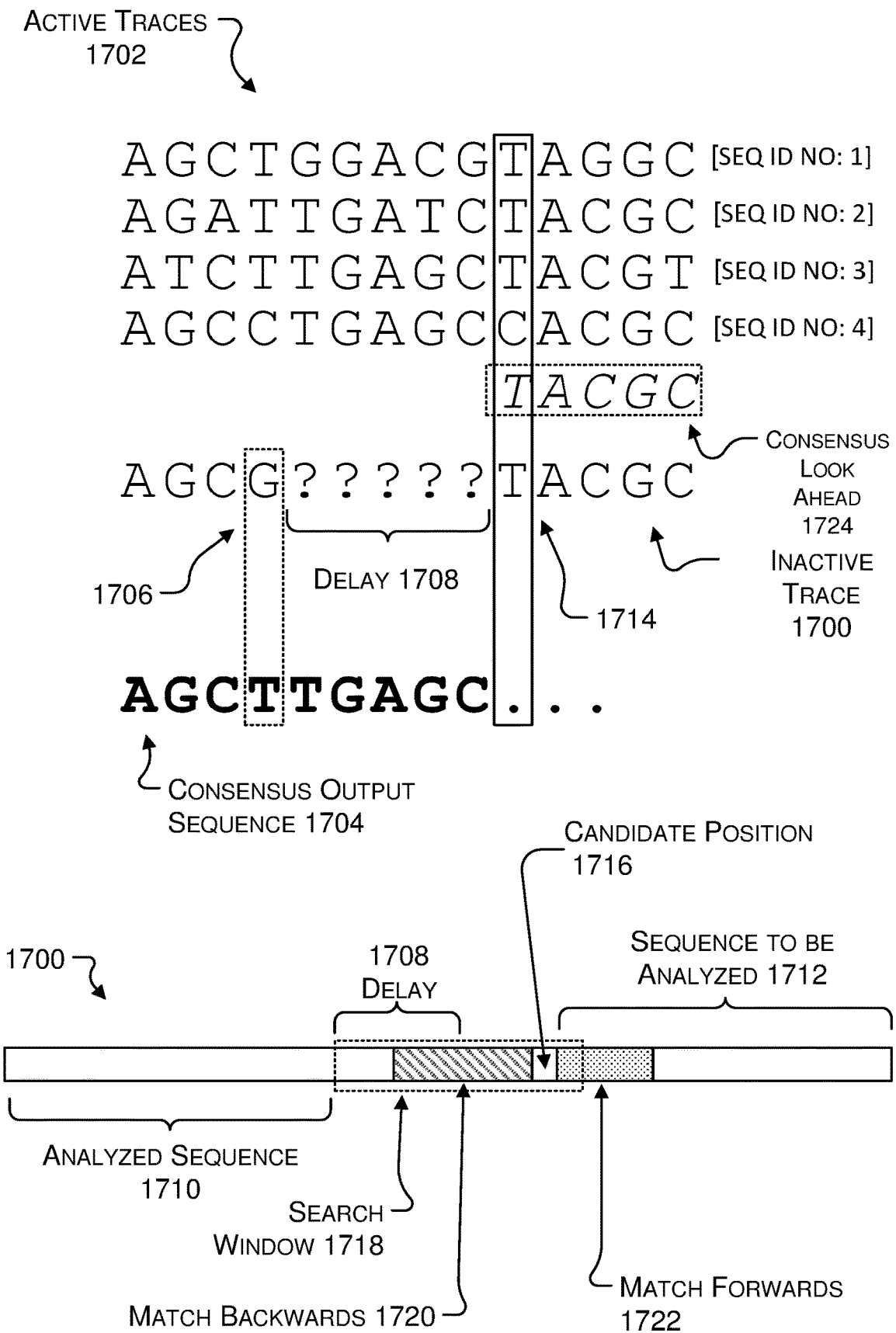
FIG. 17 shows an illustrative representation of introducing a delay into an inactive trace and locating a candidate position within the inactive trace.

FIG. 17 shows a technique for skipping over a portion of an inactive trace 1700 that contains an indeterminant error to search for a match with the active traces 1702 at a later position located further along the inactive trace 1700. The inactive trace 1700 may be labeled as an inactive trace due to identification of an indeterminant error as shown in FIG. 16. The strings of base calls represented by each of the reads in a cluster may be represented as $Y_1, Y_2, \ldots, Y_m$. The value of m can vary based on the sequencing technology and the depth of coverage. For example, with Nanopore sequencing m may be about 10-100. The inactive trace 1700 can be represented as $Y_j$.

A consensus output sequence 1704 can be generated from the active traces 1702 and portions of the inactive trace 1700. The consensus output sequence 1704 may be represented as X which is the best estimate for X the sequence for the polynucleotide provided to the oligonucleotide sequencer. As discussed previously, the consensus output sequence 1704 identifies the plurality consensus base call while accounting for insertions, deletions, and substitutions to maintain alignment of the reads relative to one another.

The position 1706 is the position in the inactive trace 1700 that was estimated when the read last became inactive. This may be the position of comparison 1600 shown in FIG. 16. This position can be represented as i*. Then p*[j] is the position in $Y_1$ that was the position of comparison when the read last became inactive. A delay 1708 of several positions (e.g., 5-10) is introduced in the inactive trace 1700 before resuming evaluation of the base calls in the inactive trace 1700. The delay 1708 is a portion of the inactive trace 1700 that will be maintained as inactive regardless of any potential matches in this area. The last "good" position in the inactive trace 1700 is identified at position 1706, but it is not known how many positions are affected by the indeterminant error. With sequences that include bursty errors such as those from Nanopore sequencing, it is likely that there are several positions adjacent or close to one another that have mismatches which will not be able to be classified as insertions, deletions, or substitutions. Introducing the delay 1708 reduces the likelihood that the inactive trace 1700 will be returned to active status at a position where there is a mismatch.

The schematic representation of the inactive trace 1700 at the bottom of FIG. 17 shows one illustrative arrangement of how the inactive trace 1700 can be evaluated to identify a matching sequence. When an indeterminant error is identified there is likely some portion of the inactive trace 1700 that has already been analyzed excessively and used to develop the consensus output sequence 1704. This section of the inactive trace 1700 is indicated as the analyzed sequence 1710. This is followed by the delay 1708 and then past the delay 1708 is a portion of the inactive trace 1700 that has the sequence which is yet to be analyzed 1712. Once it is identified how far past the delay 1708 the inactive trace 1700 can be reactivated, trace reconstruction may be resumed.

There is a position of comparison 1714 following the delay 1708 that may be represented as i. To determine if this position of comparison 1714 is within the delay 1708 region, i is compared to i*: if i−i*≤delay then the inactive trace 1700 is kept as inactive, but if i−i*>delay then the inactive trace 1700 is evaluated at position i as described below.

For alignments of the reads for which the consensus output sequence 1704 has not yet been calculated, a consensus look ahead sequence 1724 can be created from the active traces 1702. The consensus look ahead sequence 1724 may be created the same way as the look-ahead window described earlier by taking the plurality consensus vote of the active traces 1702 at a position of comparison. This technique simply uses the plurality consensus base call at each position as the base call for the consensus sequence. If there is an equal number of base calls (e.g., 5 T's and 5 C's) then ties are broken arbitrarily. However, unlike the look-head window, the consensus look ahead sequence 1724 is not limited to a window of two or three positions.

Once past the delay 1708 region, a candidate position 1716 is sought. The candidate position 1716 is a single position in the inactive trace 1700 which can be aligned with the active traces 1702 and used for continuing with determination of the consensus output sequence 1704. The candidate position 1716 can be represented as k. The candidate position 1716 may immediately follow the delay 1708 at the position of comparison 1714 or it may be located somewhere farther past the end of the delay 1708.

If insertions and deletions occurred with equal frequency from position 1706 to the candidate position 1716, then the position at which the inactive trace 1700 once again can be aligned with the active traces 1702 would be at or near the position of comparison 1714. This position of comparison 1714 may be represented as $k_0$. It can be calculated by adding the difference i−i* between the candidate position i and the position i* to the position of comparison when the read last became inactive. Thus, $k_0$:=p*[j]+(i−i*). However, there may be an unequal number of insertions and deletions from position 1706 to the candidate position 1716. Accordingly, a search window 1718 is used to evaluate multiple possible locations for a match between a subsequence of the inactive trace 1700 and the active traces 1702 in a region around $k_0$.

The search window 1718 may include a search backwards window (sbw) before $k_0$, a search forwards window (sfw) past $k_0$, as well as $k_0$ itself. Thus, the search window 1718 is a range of possible positions for k in the neighborhood of $k_0$. The multiple possibilities for k may be represented as k∈{$k_0$−sbw, $k_0$−sbw+1, . . . , $k_0$−1, $k_0$, $k_0$+$k_0$+sfw−1, $k_0$+sfw}. Each possibility fork can be evaluated to determine if there is a subsequence of the inactive trace 1700 that matches the active traces 1702. A larger search window 1718 resulting from larger values for sbw and sfw makes it more likely to find a match but also increases the possibility of returning a false positive result. The size for the search window 1718 may be determined experimentally. The total length of the search window 1718 is sbw+sfw+1. Thus, if sbw and sfw are both 5 positions long, then the length of the search window 1718 will be 11 positions. The sbw and sfw may be the same length as each other or different lengths.

Subsequences of the inactive trace 1700 within the search window 1718 are compared a comparison sequence Z to determine if there is a match. The comparison sequence Z includes the base call at position i in $\hat{X}$ and may include one or both of a match-backwards (mb) 1720 region and a match-forwards (mf) 1722 region.

The match-backwards 1720 region is located before position i and aligns with portions of the consensus output sequence 1704. A length of the match-backwards 1720 sequence may be determined experimentally and can range from, for example, 0-10 positions. Thus, the match-backwards 1720 sequence may be omitted. The match-backwards 1720 sequence may also overlap with the delay 1708. At the positions represented by the delay 1708, the consensus output sequence 1704 is determined by the active traces 1702 without using the base calls from the inactive trace 1700 at the location of the delay 1708.

The first mb+1 positions of Z are $\hat{X}[i-mb]$, $\hat{X}[i-mb+1]$, . . . $\hat{X}[i-1]$, $\hat{X}[i]$. Thus, this represents the portion of the comparison sequence Z that is the same as the consensus output sequence 1704 at the positions being evaluated. Even if the length of mb is 0, $\hat{X}[i]$ is included in Z.

The match-forwards 1722 sequence extends past position i and as such there is no consensus output sequence 1704 at corresponding positions. Thus, for the purposes of comparing to the sequence in the inactive trace 1700, the consensus look ahead sequence 1724 sequence from the active traces 1702 is used. The length of the match-forwards 1722 sequence can be, for example, 0-10 positions. Thus, if mf=0 then the match-forwards 1722 sequence is not used. Although the match-backwards 1720 sequence and the match-forwards 1722 sequence are both compared to a consensus sequence generated from the active traces 1702, each is compared to different consensus sequences. The match-backwards 1720 sequence is compared to $\hat{X}$ the consensus output sequence 1704 while the match-forwards 1722 sequence is compared to the consensus look ahead sequence 1724.

The sub-sequence of the inactive trace 1700 that is compared to Z has a length of mb+mf+1 which is the same length as Z. Thus, the matching is performed between two strings of equal length. Recall that the inactive trace 1700 may be represented as $Y_j$ and thus, the sub-sequence of the inactive trace 1700 that is compared to Z can be represented as $Y_j^k$ because its location is based on the location of k. Specifically, $Y_j^k$ can be defined as $Y_j[k-mb]$, $Y_j[k-mb+1]$, . . . , $Y_j[k-1]$, $Y_j[k]$, $Y_j[k+1]$, . . . $Y_j[k+mf-1]$, $Y_j[k+mf]$.

With these definitions of Z and $Y_j^k$ it is possible to make comparisons for each k∈{$k_0$−sbw, $k_0$−sbw+1, . . . , $k_0$−1, $k_0$, $k_0$+1, . . . , $k_0$+sfw−1, $k_0$+sfw} to determine if there is any candidate position 1716 that represents a match. A match may be no more than a distance threshold (dt) in the edit distance between the two strings. If dt=0 then only exact matches will be considered as matching. The number of comparisons may be the same as the length of the search window 1718. Thus, if the search window is 12 positions long, a sliding window of 12 positions is moved along the search window 1718 and compared to the corresponding base call sequences in Z.

If none of the candidate positions 1716 within the search window 1718 are associated with a $Y_j^k$ subsequence that matches the corresponding Z subsequence, then the inactive trace 1700 may be kept as inactive. The entire read may be discarded or only the portion of the read before the indeterminant error (i.e., the analyzed sequence 1710) may be used.

If there a candidate position 1716 within the search window that is associated with a $Y_j^k$ subsequence that matches the corresponding Z subsequence, the position of comparison for trace reconstruction may be set as the position immediately following the candidate position 1716. The location of the position of comparison may be calculated as p[j]:=k+1. The inactive trace 1700 may again be designated as an active trace and trace reconstruction including this read can proceed forward from the position of comparison.

There may be multiple candidate positions 1716, multiple locations fork, at which a match is found. If so, one of the candidate positions 1716 is selected to be used as the location for restarting trace reconstruction. One way is to select the position closest to $k_0$. Alternatively, the position farthest from $k_0$ could be selected or the selection could be random.

A given read may have more than one indeterminant error and the process of identifying the indeterminant error followed by finding a candidate position 1716 to restart trace reconstruction can be repeated multiple times in a single read. Furthermore, a cluster of reads which may include many tens of sequences can have multiple reads that include an indeterminant error. Thus, this technique can be used on more than one, including all, of the reads in a cluster. Because at various positions for i different ones of the multiple reads may be active or inactive, the set of reads that makes up the active traces 1702 can be different at different alignment locations.

Figure 18:
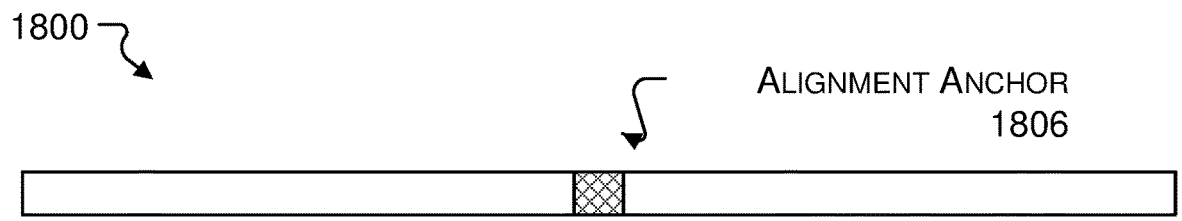
FIG. 18 shows placement positions for alignment anchors within a read.
Figure 18:
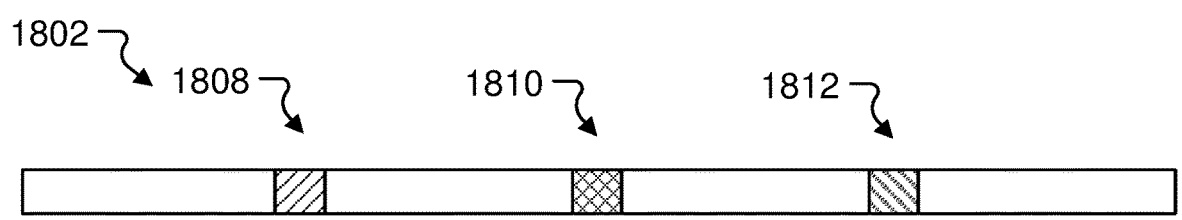
Figure 18:
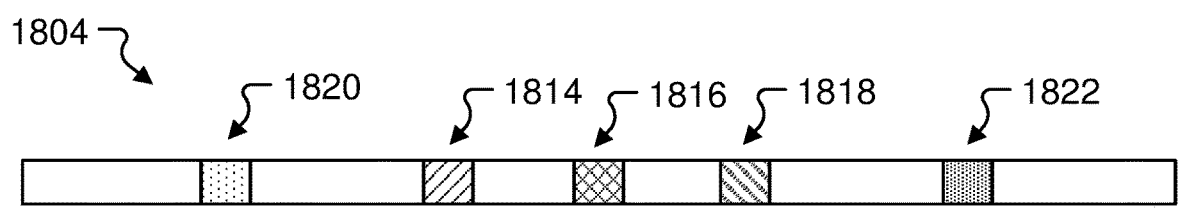

FIG. 18 is a schematic diagram of several DNA strands 1800, 1802, 1804 indicating locations of alignment anchors. Alignment anchors provide reference locations, in addition to the start and the end of the reads, that can align multiple noisy reads, and thus, assist with constructing the consensus output sequence.

Generally, the accuracy of a consensus output sequence is more accurate towards the beginning or end of a read where there is higher confidence in the strands being in correct alignment with each other. Without being bound by theory, it is possible that any errors may accumulate and cause further errors in analysis of subsequent positions along the reads. For example, if a deletion error is incorrectly identified as a substitution error, the remaining base calls in that read may be out of phase and negatively impact the accuracy of subsequent consensus base calls. One way of minimizing this effect is to use the first half of the "forward" analysis and the first half of the "reverse" analysis. Say, for example, that the length of the read to be analyzed is 200 positions. A left-to-right analysis may be performed that provides a consensus output sequence for positions 1-100. A right-to-left analysis may also be performed that provides a consensus output for positions 101-200. Both analyses may be performed in parallel. The resulting consensus output sequence provides a base call for all of positions 1-200 by combining the left-to-right analysis and the right-to-left analysis. This is referred to as a combined consensus output sequence.

Because with combined consensus output sequences are least reliable further from the ends of a read, one arrangement is to add at the alignment anchor 1806 at the center of the DNA strand 1800. This provides a position to realign the reads at the location where the relative alignment to each other is least reliable. The markers provide an "anchor" for the consensus alignment to reset and begin again without the influence of previously accumulated errors.

The alignment anchors function as markers of location and should be recognizable in each read even in the presence of noise and errors created by sequencing. The alignment anchors may be relatively short sequences of, for example, 4-8 positions. Selection of the base sequence in an alignment anchor and the length of the alignment anchor may be arbitrary. Any sequence that is consistent across multiple DNA strands that cluster together can function as an alignment anchor. Because the alignment anchors use some number of bases, this comes at the cost of reducing the number of bases in the DNA strands that are available for storing digital information. However, including alignment anchors in the DNA strands may make it possible for trace reconstruction to generate accurate consensus output sequences with lower levels of coverage thereby reducing the total amount of sequencing needed to recover the information stored in the DNA.

In an implementation, the sequence of the alignment anchors is created to avoid repeating bases and to avoid internal alignments. Because the alignment anchors are used to align multiple reads, reducing the possibility of a misalignment between alignment anchor sequences in two different reads may be beneficial. For example, ACGT is a sequence that does not have any repeating bases and does not have any internal alignments. But ACGACG could form partial alignments with itself if the first ACG in one read aligned with the last ACG in a different read. Misalignments may occur, for example, if there is an error in the base calls for positions within an alignment anchor or the sequence of the read adjacent to an alignment anchor is the same as part of the alignment anchor.

One or more alignment anchors may be included in the polynucleotide sequence of a DNA strand. There are multiple possible arrangements for the alignment anchors within a DNA strand. One arrangement is to place an alignment anchor 1806 centered in the middle of a DNA strand 1800. Placing the alignment anchor 1806 in the center of the DNA strand 1800 will of course lead to the alignment anchor sequence being at or close to the middle of the corresponding read. For example, the alignment anchor 1806 may be located between 40%-60%, 45%-55%, 49%-51%, or 50% of the distance from the beginning of DNA strand 1800 to the end of the DNA strand 1800.

DNA strands 1802 and 1804 show examples of multiple alignment anchors. If multiple alignment anchors are used, they may be arranged in various ways. DNA strand 1802 illustrates an example in which alignment anchors 1808, 1810, and 1812 are equally spaced. Thus, the number of positions between the start of the DNA strand 1802 and alignment anchor 1808, between alignment anchor 1808 and alignment anchor 1810, between alignment anchor 1810 and alignment anchor 1812, and between alignment anchor 1812 and the end of the DNA strand are all substantially the same. The alignment anchors can act as additional "ends" to the DNA strand 1802 for the purpose of aligning multiple reads. Thus, if DNA strand 1802 is 200 bp long, rather than creating one right-to-left consensus output sequence of 100 positions and one left-to-right consensus output sequence of 100 positions, the alignment anchors 1806, 1810, and 1812 divide the DNA strand 1802 into four regions of approximately 50 bp each. Thus, the length of sequencing before an alignment point is reached is shortened from 200 bp to about 50 bp and the opportunity for mistaken base calls to place one of the reads out of phase with the others is also decreased.

In a different arrangement illustrated by DNA strand 1804, the spacing of alignment anchors may be biased towards the center of the DNA strand. Thus, the alignment anchors 1814, 1816, and 1818 near the center of the DNA strand 1804 are located closer together than the alignment anchors 1820 and 1822 which are farther away from the center. Also, alignment anchors 1820 and 1822 may be yet farther away from the respective ends of the DNA strand 1804. Each alignment marker used together should be unique so that it can be differentiated from other markers. Thus, anchors 1814-1822 will each have different sequences. The length of the individual anchors may also be different.

Figure 19:
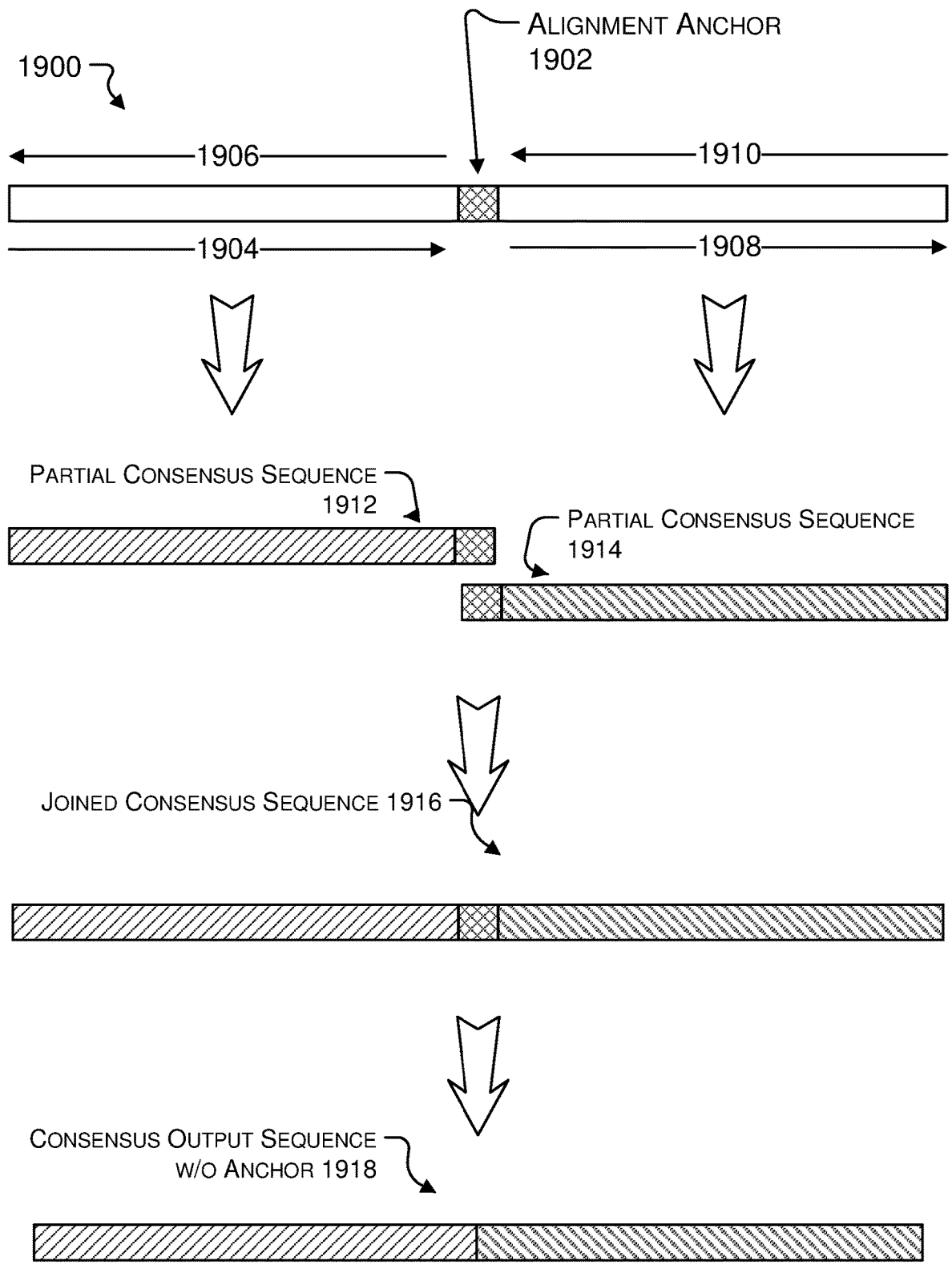
FIG. 19 shows generating partial consensus sequences from segments of a read divided by an alignment anchor.

FIG. 19 uses schematic diagrams of reads to illustrate how partial consensus sequences generated from portions of reads divided by alignment anchors can be joined to create a full consensus output sequence. The read 1900 illustrated in FIG. 19 may, for example, be generated from the DNA strand 1800 shown in FIG. 18. The alignment anchor 1902 may be located in the middle of the read 1900 about 50% of the way between the left end and the right and of the read 1900. Even if the alignment anchor 1902 is located exactly 50% along the length of the DNA strand, insertions and/or deletions introduced during sequencing may shift the position of the alignment anchor 1902 in the read so that it is no longer exactly in the middle. Thus, alignment anchor 1902 divides the read 1900 into two portions of roughly equal length.

Because the sequence of the alignment anchor 1902 is known (assuming no errors in this portion of the read 1900), a search for that known sequence (e.g., AGCT) may identify one or more matches throughout the read 1900. The placement of the alignment anchor 1902 is also known, so any matches that are not within a threshold distance from the middle of the read 1900 may be ignored. Thus, the location of the alignment anchor 1902 can be identified in the read 1900 and in other reads in the same cluster.

If the read 1900 is 180 positions long and the alignment anchor 1902 is four positions long and located exactly in the middle, then the left subsequence of read 1900 located to the left of the alignment anchor 1902 will be 88 positions long and the right subsequence located to the right of the alignment anchor 1902 will also be 88 positions long. The left subsequence may be analyzed by forward and reverse analysis to generate a left-to-right consensus output sequence 1904 and a right-to-left consensus output sequence 1906. Similarly, the right subsequence may be analyzed to generate the consensus output sequences 1908 and 1910.

As discussed above, only the first half of each of these four consensus output sequences 1904-1910 may be used to minimize errors introduced by accumulative phase shifts caused by insertions and deletions resulting from sequencing. In this implementation, only 44 positions would be analyzed before switching to the consensus output sequence running the opposite direction. Alternatively, more than half of each of the respective consensus output sequences may be used so that there is some level of overlap near the middle of the subsequences. In the area of overlap, base calls from both the left-to-right and the right-to-left consensus output sequences may be used to determine the consensus output base call that will be assigned to a position.

Combination of the left-to-right consensus output sequence 1904 and the right-to-left consensus output sequence 1906 may generate a partial consensus sequence 1912 for the left half of the read 1900. Similarly, the consensus output sequences 1908 and 1910 may be combined in any suitable manner to generate the partial consensus sequence 1914 for the right half of the read 1900. The partial consensus sequence 1912 may be aligned with the partial consensus sequence 1914 by reference to the alignment anchor 1902.

Once aligned, the partial consensus sequence 1912 and the partial consensus sequence 1914 may be joined using the alignment anchor 1902 to create a single joined consensus sequence 1916. The joined consensus sequence 1916 represents a consensus output sequence for the read 1900 that was developed from the forward and the reverse consensus output sequences 1904-1910. This contrasts with an implementation that does not use alignment anchors in which the consensus output sequence for the read 1900 would be created from only one forward and one reverse consensus output sequences.

Because the alignment anchor 1902 does not encode digital information like other portions of the read 1900, the base calls corresponding to the alignment anchor 1902 may be removed to create the consensus output sequence without the alignment anchor 1918. The consensus output sequence without the alignment anchor 1918 represents a string of base calls that can be decoded to recover the digital information contained in the read 1900.

Figure 20:
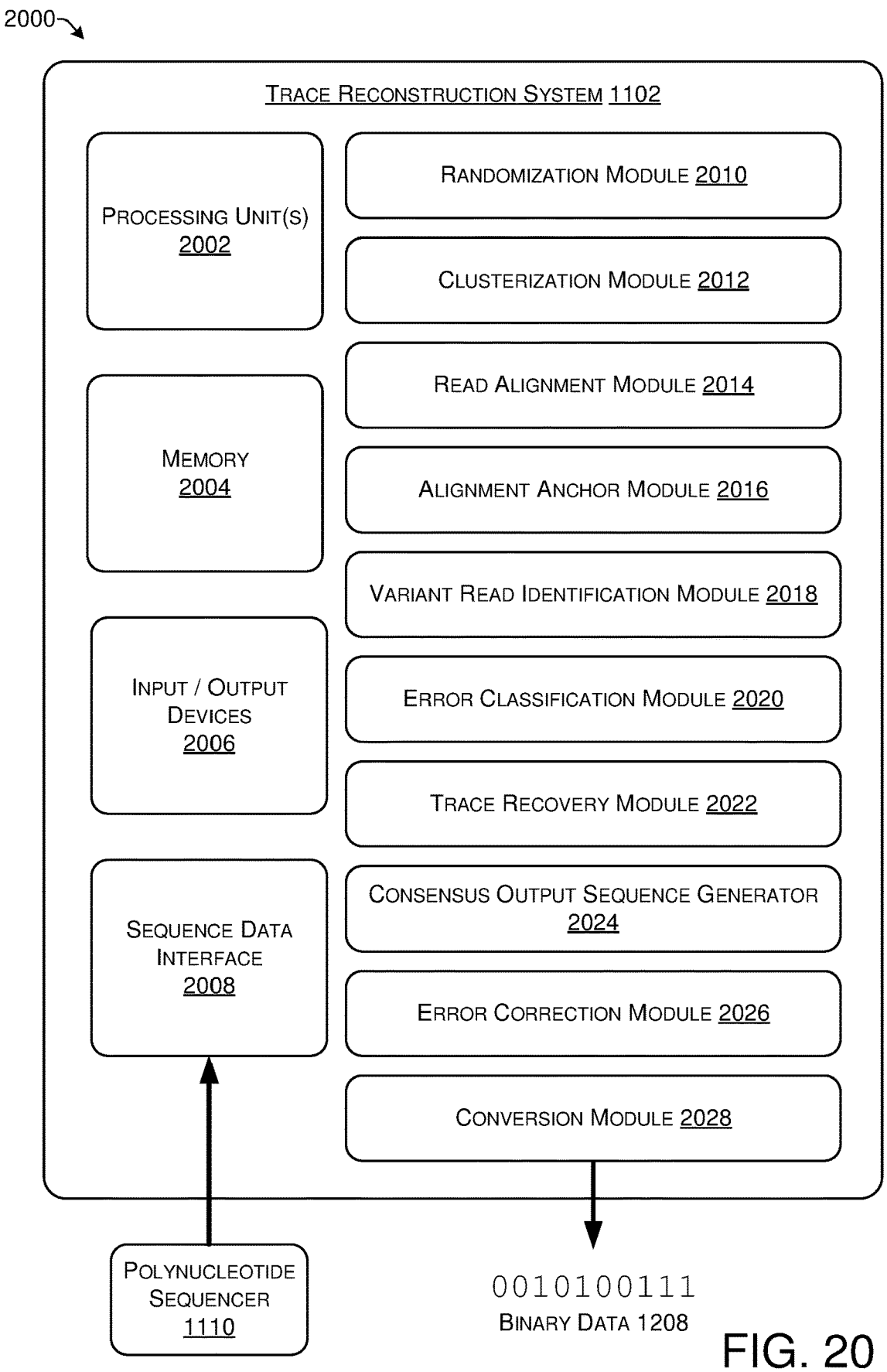
FIG. 20 shows a block diagram of an illustrative trace reconstruction system.

FIG. 20 shows an illustrative block diagram 2000 of the trace reconstruction system 1102 shown in FIG. 11. The trace reconstruction system 1102 may be implemented in whole or in part in any of the computing device 1112, the polynucleotide sequencer 1110, or the servers 1114. Thus, the trace reconstruction system 1102 may be implemented in a system that contains one or more processing unit(s) 2002 and memory 2004, both of which may be distributed across one or more physical or logical locations. The processing unit(s) 2002 may include any combination of central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 2002 may be implemented in software (e.g., ultimately executed on hardware) and/or firmware in addition to hardware implementations. Software or firmware implementations of the processing unit(s) 2002 may include computer- or machine-executable instructions written in any suitable programming language to perform the various functions described. Software implementations of the processing unit(s) 2002 may be stored in whole or part in the memory 2004.

Alternatively, or additionally, the functionality of the trace reconstruction system 1102 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Implementation as hardware logic components may be particularly suited for portions of the trace reconstruction system 1102 that are included as on-board portions of the polynucleotide sequencer 1110.

The trace reconstruction system 1102 may include one or more input/output devices 2006 such as a keyboard, a pointing device, a touchscreen, a microphone, a camera, a display, a speaker, a printer, and the like.

Memory 2004 of the trace reconstruction system 1102 may include removable storage, non-removable storage, local storage, and/or remote storage to provide storage of computer-readable instructions, data structures, program modules, and other data. The memory 2004 may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The trace reconstruction system 1102 may be connected to one or more polynucleotide sequencers 1110 through a direct connection and/or a network connection by a sequence data interface 2008. The direct connection may be implemented as a wired connection, a wireless connection, or both. The network connection may travel across the network 1116. The sequence data interface 2008 receives one or more reads from the polynucleotide sequencer 1110.

The trace reconstruction system 1102 includes multiple modules that may be implemented as instructions stored in the memory 2004 for execution by processing unit(s) 2002 and/or implemented, in whole or in part, by one or more hardware logic components or firmware.

A randomization module 2010 randomizes input digital data before encoding it in DNA with oligonucleotide synthesizer 1104. The randomization module 2010 may create a random, more accurately pseudo-random, string from the input digital data by taking the exclusive-or (XOR) of the input string and a random string. The random string may be generated using a seeded pseudo-random generator based on a function and a seed. Such randomization of the input digital data increases randomness in synthetic DNA strands 1200 which results in the noisy reads 1202 coming from a polynucleotide sequencer 1110 themselves having a pseudo-random sequence of A, G, C, and T. The randomness facilitates decoding (i.e., clustering and trace reconstruction).

A clusterization module 2012 clusters a subset of the plurality of reads based on a likelihood of the subset of the plurality of reads being derived from the same DNA strand. Data received at the sequence data interface 2008 from the polynucleotide sequencer 1110 may contain a set of reads generated from each DNA strand provided to the polynucleotide sequencer 1110. Although there may be errors in many of the reads, the reads from the same DNA strand are generally more similar to each other than they are to reads from a different DNA strand. Further analysis would be hampered if the set of reads to be analyzed includes reads of different DNA strands. Thus, clustering may be performed in order to limit the data for further analysis to a subset of the reads that are believed to represent the same DNA strand. A poorly formed cluster may be "poorly" formed due to over or under inclusion. An overly inclusive, poorly formed cluster is one that groups reads of more than one strand in a single cluster. An underinclusive, poorly formed cluster is one of multiple clusters that should be grouped into a single large cluster but instead are divided into multiple smaller clusters. The clusterization module 2012 can use any suitable clustering technique such as connectivity-based clustering (e.g., hierarchical clustering), centroid-based clustering (e.g., k-means clustering), distribution-based clustering (e.g., Gaussian mixture models), density-based clustering (e.g., density-based spatial clustering of applications with noise (DBSCAN)), etc. The trace reconstruction system 1102 may analyze one or more, including all, of the clusters derived from the data output by the polynucleotide sequencer 1110. As mentioned above, the number of reads in a cluster may depend on the depth of sequencing. With Nanopore sequencing, there may be between about 10 to 100 reads per cluster.

A read alignment module 2014 aligns the plurality of reads at a position of comparison spanning the plurality of reads. Initially, the left ends of the reads (corresponding to the 5' ends of the DNA strands) may be aligned. This first position in the reads may be used as the initial position of comparison. As analysis proceeds, the read alignment module 2014 moves the position of comparison along each read a number of positions based on identified error types.

The read alignment module 2014 advances the position of comparison by one position for reads that have the plurality consensus base call at the position of comparison, by one position for a variant read if the error type is classified as substitution, by zero positions for a variant read if the error type is classified as deletion, or by two positions for a variant read if the error type is classified as insertion.

The read alignment module 2014 may also generate a "reverse" alignment that begins with the reads aligned at the right end (corresponding to the 3' ends of the DNA strands). Analysis then proceeds in an identical manner except that movement to the "right" becomes movement to the left. The consensus output sequence 1204 is potentially different for the same set of reads when analyzed from left to right as compared to right to left.

Generally, the accuracy of a consensus output sequence 1204 is more accurate towards the beginning of the reads where there is higher confidence in the alignment being correct. Without being bound by theory, it is possible that any errors may accumulate and cause further errors in analysis of subsequent positions along the reads. For example, if a deletion error is incorrectly identified as a substitution error, the remaining base calls in that read may be out of phase and negatively impact the accuracy of subsequent error identification. One way of minimizing this effect is to use the first half of the "forward" analysis and the first half of the "reverse" analysis. Say, for example, that the length of the reads to be analyzed is 100 positions. A left-to-right analysis may be performed that provides a consensus output sequence 1204 for the first 50 positions. A right-to-left analysis may be performed that provides a consensus output sequence 204 for the last 50 positions. Both analyses may be performed in parallel. The resulting consensus output sequence 1204 is a combination of the 50 base pairs identified by the left-to-right analysis and the 50 base pairs identified by the right-to-left analysis. This is referred to as a combined consensus output sequence.

An alignment anchor module 2016 functions by identifying locations of alignment at locations other than the ends of the reads when an alignment anchor sequence is present.

When alignment anchors are present, the alignment anchor module 2016 may function together with the read alignment module 2014 to create alignments of segments of reads between one of the ends of a read and an alignment anchor as well as between two alignment anchors if present. The alignment anchor module 2016 can identify an alignment anchor sequence that is present in a read. The alignment anchor sequence is a predetermined sequence such as illustrated in FIGS. 18 and 19. The alignment anchor sequence may be a sequence that is 3-8 bp. In some implementations, alignment anchor sequences may be 4-6 bp long. The alignment anchor sequence may be an arbitrary sequence that is included by design in DNA strands synthesized by the oligonucleotide synthesizer 1104. Thus, a few nucleotide bases in the DNA strands are not used to encode digital information but instead are used to insert a known sequence—the alignment anchor sequence. To reduce the probability of misalignment between two alignment anchor sequences, the sequence used as the alignment anchor sequence may be designed without repeating nucleotides and so that it will not align with itself. For example, the sequence "AGCT" may be a suitable sequence for an alignment anchor whereas the sequences "ACACAC" and "TTGG" would be more likely to misalign.

Once alignment anchors are identified and the reads aligned at the alignment anchors, the alignment anchor module 2016 may also divide the read into multiple sub-reads such as a first sub-read and a second sub-read. If there is only one alignment anchor sequence in the read, then the first sub-read may extend from the beginning of the read (e.g., 5'-end) to the alignment anchor sequence and the second sub-read may extend from the alignment anchor sequence to the end of the read (e.g., the 3'-end). The alignment anchor module 2016 may do this for each of the reads under analysis, creating a third, fourth, etc., sub-reads.

The read alignment module 2014 may then align the sub-reads in a similar manner as it aligns entire reads except that the alignment is not based only on the end of the reads but also on the alignment anchors that divide the reads. Thus, the read alignment module 2014 can align the first sub-sequence from the first half of a first read with a third sub-sequence that is from the first half of a second read. The second half of the first read represented by the second sub-sequence can also be aligned with a fourth sub-sequence that represents the second half of the second read. Thus, instead of aligning the entirety of the first read and the second read, the sub-sequences of the reads are aligned. Of course, in many implementations more than two reads will be aligned.

Because the sub-sequences are shorter than the entire reads the effects of accumulated mistakes in generation of the consensus output sequence are reduced. There is a smaller number of positions over which errors may shift one of the reads out of phase with the other reads. If errors did accumulate or a read was out of phase with the other reads in the same cluster, the alignment would be "reset" at the alignment anchor sequence. The sub-reads may be aligned in both forwards and reverse orientations as described above for entire reads and as shown in FIG. 19. Thus, each alignment of sub-sequences (e.g., the first sub-sequence, second sub-sequence, third sub-sequence, and fourth sub-sequence from the above example) may be analyzed in the same way as alignments of entire sequences.

A variant read identification module 2018 determines a plurality consensus base call at the position of comparison and labels a read that has a different base call at the position of comparison as a variant read. In some implementations, the variant read identification module 2018 may use an error profile associated with the polynucleotide sequencer 1110 as discussed above to determine the plurality consensus base call. The variant read identification module 2018 may flag or otherwise identify every read that is a variant read for a given position of comparison. This flag will then identify that read as one that should be identified for determination of an error type. With each movement of the position of comparison, the identity of which reads are variant reads and which are not variant reads changes.

An error classification module 2020 classifies an error type for variant reads as substitution, deletion, or insertion. If an error cannot be uniquely classified, the error classification module 2020 may indicate that the type of error is indeterminate or that the error type is limited to one of two possibilities. Classification of an error by the error classification module 2020 may be based in part on comparison of a consensus string of base calls in a look-ahead window of a subset of the plurality of reads having the plurality consensus base call at the position of comparison (i.e., the non-variant reads) and base calls in the variant read. Variant reads other than the one being analyzed at a given iteration are not used when determining an error type. If the error classification module 2020 classifies an error in a read as an indeterminant error, the variant read identification module 2018 may label the read as an inactive trace.

As described above in FIG. 13, the error type is classified as a substitution upon the consensus string of base calls in the look-ahead window matching a string of base calls in the variant read following the position of comparison. As described above in FIG. 14, the error type is classified as a deletion upon the look-ahead window consensus matching the base call at the position of comparison in the variant read and one or more following positions.

As described above in FIG. 15, the error type there is classified as an insertion. It is classified as an insertion because (1) a base call in the variant read following the position of comparison (i.e., the first base call in the look-ahead window for the variant read) matches the plurality consensus base call and (2) the consensus string of base calls in the look-ahead window matching a string of base calls in the variant read equal in length to the look-ahead window and starting two positions following the position of comparison. As described above in FIG. 16, the error type is classified as an indeterminant error if it cannot be classified as a substitution, a deletion, or an insertion.

A consensus output sequence generator 2022 determines a consensus output sequence 1204 based at least in part on the plurality consensus bases and the error types identified along the aligned reads. Each position in the consensus output sequence 1204 is the plurality consensus base at that position in view of the adjusted alignment of the reads due to error type classification. An error profile of the polynucleotide sequencer 1110 and/or quality information of the individual base calls may also be used to determine the consensus output sequence 1204 through influencing the identification of plurality consensus bases and error types.

The consensus output sequence generator 2022 may also generate and assemble consensus output sequences for alignments of sub-sequences defined by alignment anchor sequences. Assembling consensus output sequences for two or more sub-sequences of a cluster of reads may include generating both a forward consensus sequence and a reverse consensus sequence for each sub-sequence as shown in FIG. 19. The forward consensus sequence and the reverse consensus output sequences may be combined as described above to create multiple combined consensus sequences for each cluster of reads. The sequence of the alignment anchor(s) is used to append combined consensus sequences together. For example, a first combined consensus sequence representing the first half of a read and a second combined consensus sequence representing a second half of the read may be appended to each other by alignment at the alignment anchor sequence. If multiple alignment anchors are present, multiple combined consensus sequences may be appended in the correct order by alignment at the respective alignment anchor sequences. After appending the two or more combined consensus sequences together, the alignment anchor sequence(s) may be removed to leave a string that is a combined consensus sequence for the reads without the alignment anchor sequences. A combined consensus sequence assembled from multiple sub-sequences may be more accurate than a combined consensus sequence made from the entire length of a read without alignment anchors because the number of positions traversed (and the number of opportunities for reads to become out of phase with each other) by any forward consensus sequence or reverse consensus sequence is fewer. Reducing the amount of accumulated errors may also reduce the coverage or sequencing depth needed to form clusters that can yield accurate consensus sequences.

An error correction module 2026 may apply additional error correction techniques to decode the consensus output sequence 1204. In some implementations, the error correction module 2026 uses a non-binary error-correcting code to decode the consensus output sequence 1204 based on redundant data that is encoded into the strands. One example of this type of error correction is Reed-Solomon error correction. In an example implementation, a Reed-Solomon outer code may be added to the starting binary data and ultimately distributed across many strands of DNA (e.g., 10,000-100,000 strands) when stored. It is possible that the Reed-Solomon error correction may fail to decode the consensus output sequence 1204 if there are more than a threshold number of errors. If this occurs, trace reconstruction may be repeated with a change in one of the parameters. Changing a parameter may result in a different consensus output sequence 1204 that the Reed-Solomon error correction is able to decode. The length of the look-ahead window (w) is one parameter that could be changed. A look-ahead window of length three could be used instead of a look-ahead window of length two (or vice versa). Cut off thresholds for labeling a read as an inactive trace, the length of the delay, accepting a base call based on quality information, and biasing an error type classification for ambiguous errors could all be varied by making them more lenient or stricter. After changing one or more parameters, it can be determined if the consensus output sequence 1204 is different from the previous consensus output sequence 1204, and if it is, Reed-Solomon error correction may be applied to the new consensus output sequence 1204 to see if it is able to decode the sequence.

A conversion module 2028 converts the consensus output sequence into binary data 1208 representing at least a portion of a digital file. The conversion from a series of base calls to a string of binary data 1208 is performed by reversing the operations that were originally used to encode the binary data 1208 as a series of base calls. These operations will be known to the entity that operates the DNA storage library 1106. In some implementations, the converter 1206 introduced in FIG. 12 may include the same functionalities as the conversion module 2028 as well the error correction module 2026, and possibly other modules. The binary data 1208 may be used in the same manner as any other type of binary data. If the various error correction techniques are sufficient, the binary data 1208 will represent a perfect reproduction of the original binary data.

Example 26—Example Trace Reconstruction Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted.

Figure 21:
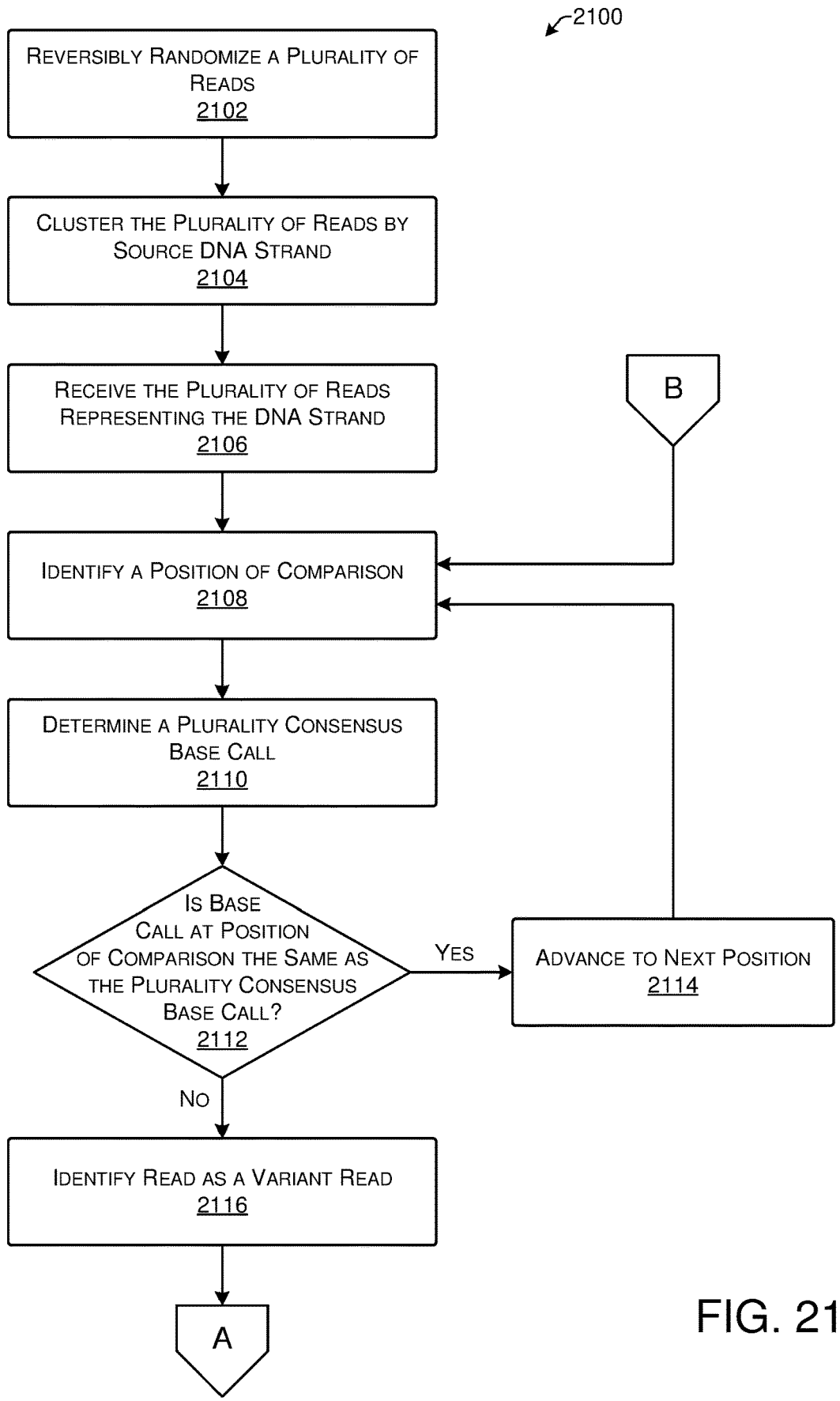
FIGS. 21 and 22 show an illustrative process for determining a consensus output sequence from a plurality of reads.
Figure 22:
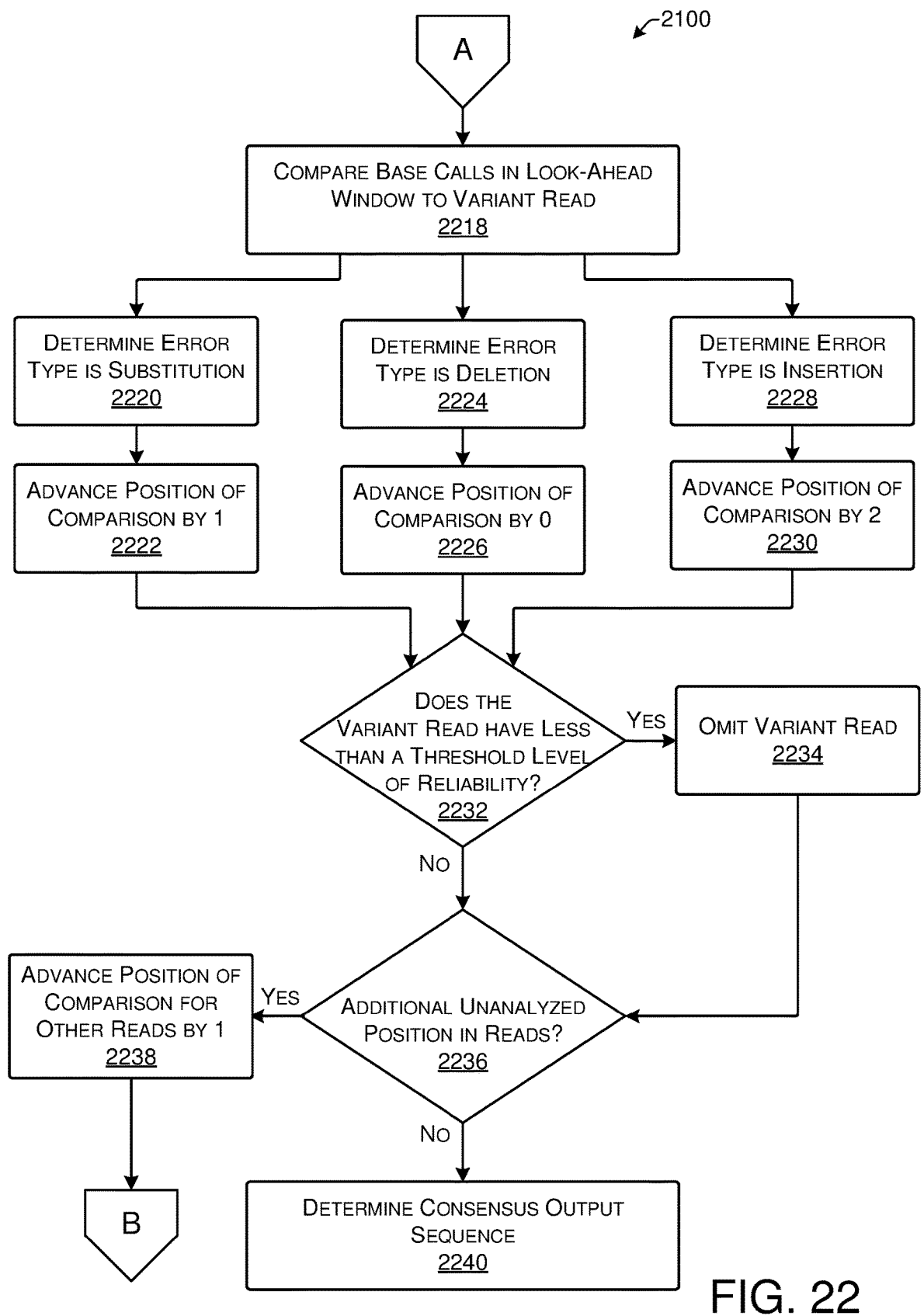

FIGS. 21 and 22 show process 2100 for correcting insertion, deletion, and substitution errors in sequence data generated by a polynucleotide sequencer. The process 2100 may be implemented by the trace reconstruction system 1102 shown in FIGS. 11, 12, and 20.

At 2102, binary data to be encoded as one or more DNA strands is reversibly randomized. This randomization occurs before synthesis of DNA strands and in some implementations is present in all reads. The reads may be received via the sequence data interface 2008 shown in FIG. 20. The reads may be randomized by the randomization module 2010 shown in FIG. 20.

At 2104, the sequence data generated by the polynucleotide sequencer are clustered using a clustering technique. Any suitable clustering technique may be used and one of ordinary skill in the art will be able to identify a suitable clustering technique. Clustering creates groups of reads derived from the same source DNA strand. Clustering may be performed by the clusterization module 2012 shown in FIG. 20. In some implementations, performing the clustering on randomized data improves the ability of the clustering technique to separate accurately the plurality of reads into distinct groups. A poorly formed cluster is one that contains reads derived from different DNA strands. Techniques such as discarding reads that deviate more than a threshold amount from a consensus sequence may prevent poorly formed clusters from impacting the final consensus output sequence. However, discarding an entire read loses any useful information that may be obtained from that read.

At 2106, a plurality of reads classified as representing a DNA strand are received for further analysis. The reads may be classified as representing the same DNA strand based on clustering performed at 2104. The plurality of reads may also be classified as representing the same DNA strand due to use of a sequencing technique in which the input for the polynucleotide sequencer is only a single DNA strand (or essentially identical copies thereof produced by PCR). In some implementations, the plurality of reads may be received via the sequence data interface 2008 shown in FIG. 20. In other implementations, the plurality of reads may be received following clustering performed by the clusterization module 2012.

At 2108, a position of comparison spanning the plurality of reads is identified. The position of comparison may be similar to the position of comparison 1300 shown in FIG. 13, the position of comparison 1400 shown in FIG. 14, the position of comparison 1500 shown in FIG. 15, or the position of comparison 1600 shown in FIG. 16. In an implementation, the position of comparison may be identified by the read alignment module 2014 shown in FIG. 20.

At 2110, a plurality consensus base call at the position of comparison is determined by identifying the most common base call at that position. Ties may be broken arbitrarily. As described above, the most common base call may be identified in part by consideration of quality information for the base calls present at the position of comparison. In an implementation, the plurality consensus base call may be determined by the variant read identification module 2018 shown in FIG. 20.

At 2112, it is determined if the base call at the position of comparison is the same as the plurality consensus base call. If it is the same, then the read being analyzed has the expected base call at this position, is not a variant read with respect to this position, and process 2100 follows "yes" path to 2114.

At 2114, process 2100 advances to the next position along the read. If, however, the base call at the position of comparison does not match the plurality consensus base call, process 2100 follows "no" path from 2112 to 2116.

At 2116, a read from the plurality of reads that has a base call in the position of comparison that differs from the plurality consensus base call is identified as a variant read. In an implementation, this identification may be performed by the variant read identification module 2018 shown in FIG. 20.

Moving to FIG. 22, at 2218, a consensus string of base calls in a look-ahead window adjacent to the position of comparison is compared to base calls in the variant read. The consensus string of base calls in the look-ahead window may be limited to the base calls from the subset of reads that has the plurality consensus base call at the position of comparison. For example, in a set of 10 or 20 reads more than one may be variant reads due to the base call at the position of comparison not matching the plurality consensus base call. When a comparison is made for one of the variant reads, the base calls in the look-ahead window of the other variant reads are not considered. This is because the other variant reads may have deletion or insertion errors that would cause the base calls in the look-ahead window to be out of phase and possibly incorrect. A type of error can be determined for the variant read based at least in part on this comparison. In an implementation, this comparison may be performed by the error classification module 2020 shown in FIG. 20. In one implementation, a length of the look-ahead window may be 2-4 positions.

At 2220, the error type for the variant read is determined to be a substitution based on the consensus string of base calls in the look-ahead window being the same as the string of base calls in a look-ahead window following the position of comparison for the variant read. Thus, the look-ahead window of the variant read matches the look-ahead window of the non-variant reads. This relationship is shown, for example, in FIG. 13.

At 2222, the position of comparison for the variant read is advanced one position.

In the alternative, at 2224, the error type for the variant read is determined to be a deletion based on the consensus string of base calls in the look-ahead window being the same as a string of base calls in the variant read including the base call in the position of comparison and adjacent base calls. The length of this string of base calls in the variant read is equal in length to the length of the look-ahead window. Thus, for example, if the length of the look-ahead window is three positions, the string of base calls in the variant read includes the base call in the position of comparison and the next two base calls. This relationship is shown, for example, in FIG. 14.

At 2226, the position of comparison for the variant read is advanced zero positions. Because there is a deletion, not advancing the position of comparison for the variant read re-aligns the strands so that the strands will be in phase for subsequent analysis.

As a further alternative, at 2228, the error type for the variant read is determined to be an insertion based on base calls matching two specific ways. First, a base call in the variant read following the position of comparison is the same as the plurality consensus base call and, second, the consensus string of base calls in the look-ahead window is the same as a string of base calls in the variant read sequence. The string of base calls in the variant read sequence is equal in length to the look-ahead window and a starting position for this string of base calls is two positions after the position of comparison. This relationship is shown, for example, in FIG. 15.

At 2230, the position of comparison for the variant read is advanced by two positions. The position of comparison is advanced one position to account for the insertion and advanced a second position because the position of comparison is advanced one position for all of the non-variant strands. This maintains alignment between the strands for subsequent analysis.

In each of 2220, 2224, and 2228, the error type for the variant read at the position of interest may be determined based at least in part on an error profile associated with the polynucleotide sequencer. Consideration of the error profile of the polynucleotide sequencer may change either or both of the determination of the plurality consensus base call and the consensus string of base calls in the look-ahead window. In an implementation, consideration of the error profile may be performed by the consensus output sequence generator 2024.

At 2232, it is determined if the variant read has less than a threshold level of reliability. The threshold level may be a number of errors in the variant read; a number of errors in the variant that cannot be uniquely classified; a minimum, median, or mode of the confidence levels for base calls in the variant read; or other factor(s). The threshold number may be a number of positions ranging from one to the total number of positions in the variant read. The threshold number may also be a percentage ranging from 1% to 100%. If the variant read has less than the threshold level of reliability, process 2100 proceeds along the "yes" path to 2234.

At 2234, the variant read is omitted and a single consensus output sequence from the plurality of reads is determined without using the variant read. Following omission of the variant read, process 2100 proceeds to 2236. Alternatively, if the variant read does not have less than the threshold level of reliability (i.e., it is considered reliable) the variant read is used for further analysis and process 2100 proceeds along the "no" path to 2236. If the variant read is classified as such due to the presence of an indeterminate error that cannot be classified as an insertion, deletion, or substitution, instead of discarding the read, it may be analyzed further as shown in FIG. 13 and/or FIG. 14 below.

At 2236, it is determined if there are additional unanalyzed positions in the reads. Thus, it is determined if the "end" of the reads has been reached and a plurality consensus base call has been identified for the positions of the reads. The end of the reads may also be identified by an alignment anchor if used to break the read into multiple smaller segments. If the analysis has not yet reached the end, then process 2100 proceeds along the "yes" path to 2238.

At 2238, the position of the subset of the plurality of reads having the plurality consensus base call at the position of comparison (i.e., the non-variant reads) is advanced by one. The new position of comparison for the variant read is advanced by an amount based on the identified error type at 2222, 2226, or 2230. The new position of comparison may be similar to new positions of comparison 1312, 1412, 1512, and 1608, shown in FIGS. 13-16. Process 2100 then returns to 2208 and analysis continues.

At 2236, if there are no unanalyzed positions in the reads, then process 2100 proceeds along the "no" path to 2240.

At 2240, a single consensus output sequence is determined based in part on the plurality consensus base call and the error type. The single consensus output sequence may be determined by the consensus output sequence generator 2024 shown in FIG. 20.

Figure 23:
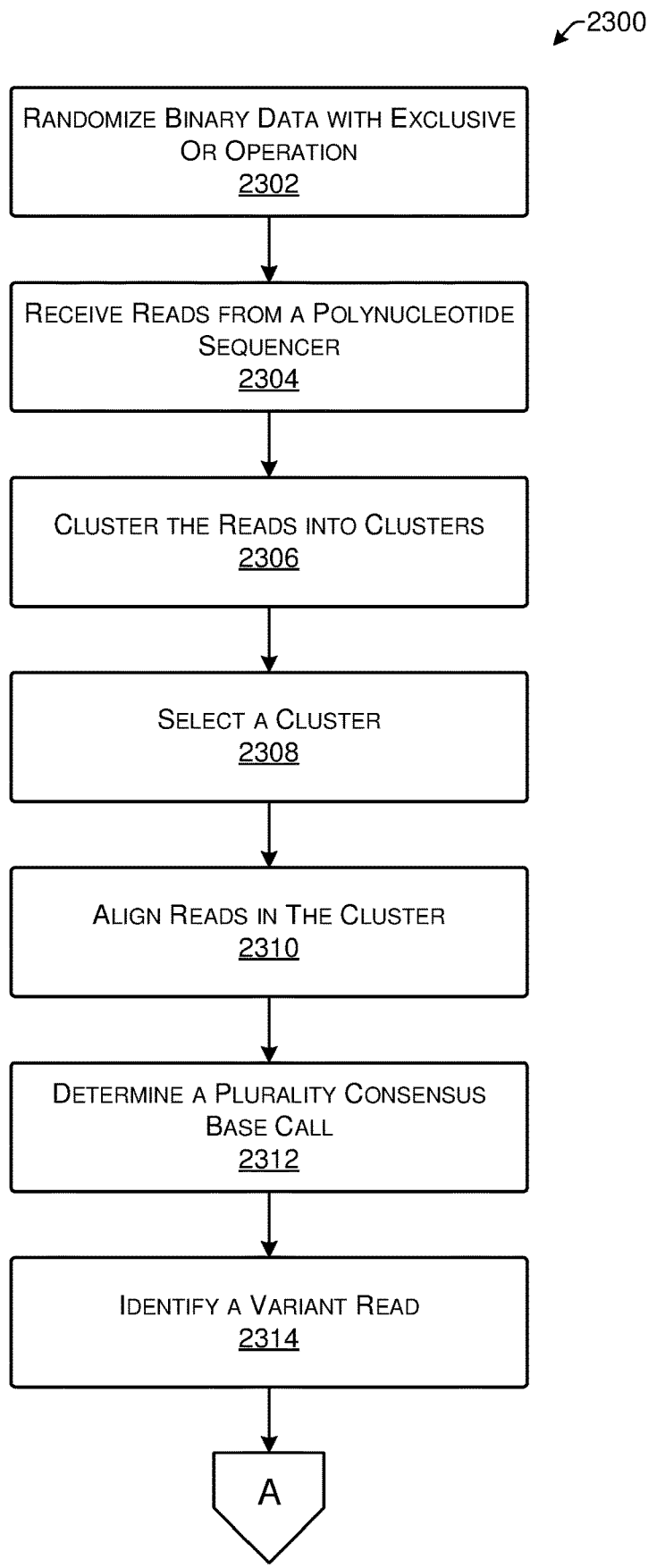
FIGS. 23 and 24 show an illustrative process for generating binary data from reads received from a polynucleotide sequencer.
Figure 24:
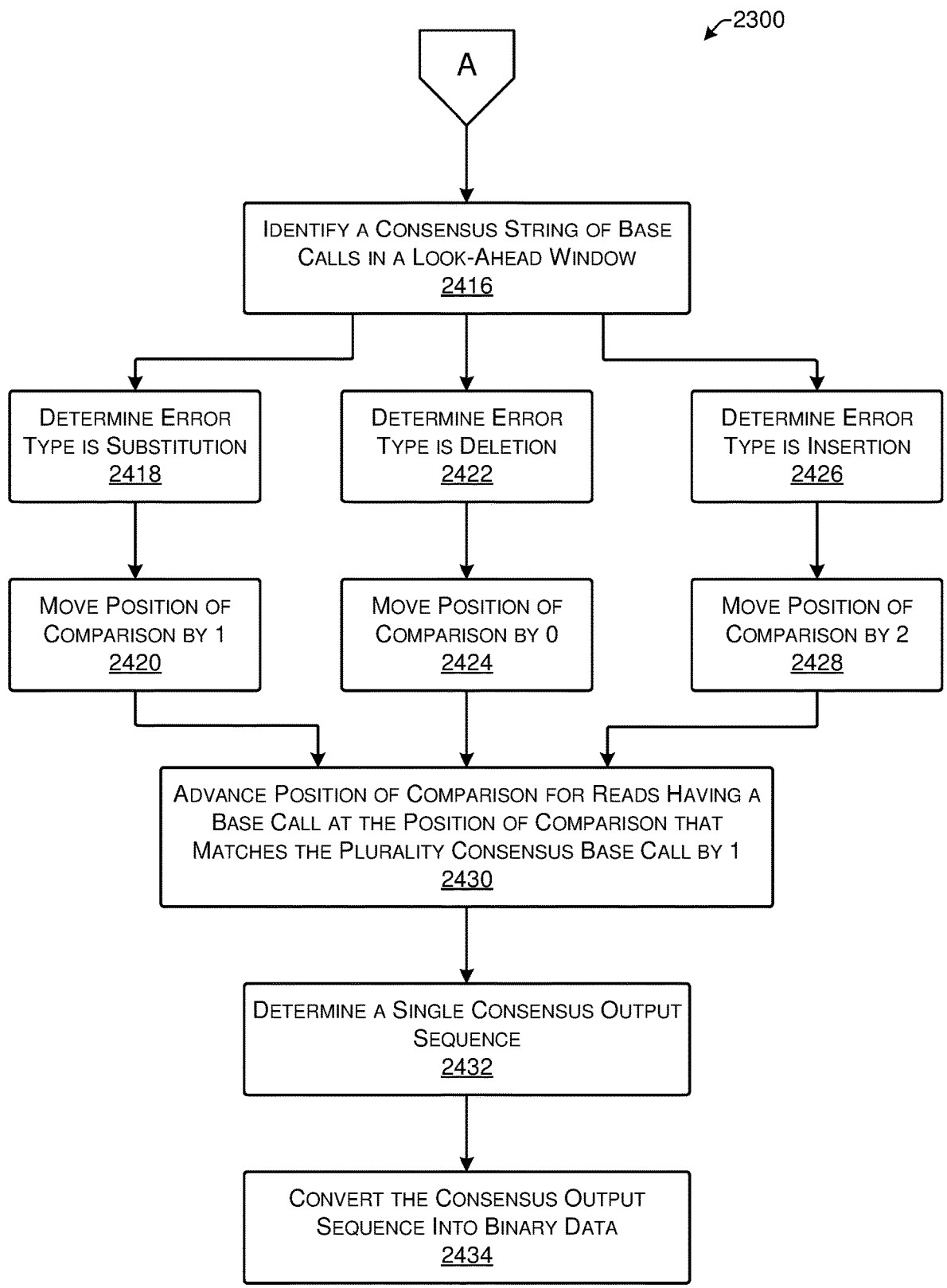

FIGS. 23 and 24 show process 2300 for recovering binary data encoded in a synthetic DNA strand by accounting for insertion, deletion, and/or substitution errors. The process 2300 may be implemented by the trace reconstruction system 102 shown in FIGS. 1, 2, and 10.

At 2302, binary data to be encoded as DNA is reversibly randomized by taking the exclusive or (XOR) of the binary data and a random sequence generated by a seed and a function. This operation affects the DNA strands that, when read, produce reads that also have characteristics of being randomized. In an implementation, the randomization may be performed by the randomization module 2010 shown in FIG. 20.

At 2304, a plurality of reads are received from a polynucleotide sequencer. In an implementation, the plurality of reads may be received by the sequence data interface 2008 shown in FIG. 20.

At 2306, the plurality of reads is clustered into a plurality of clusters by sequence similarity. Similar sequences are likely to have originated from sequencing of the same DNA strand (the sequences are not identical due to errors introduced by the polynucleotide sequencer). Thus, one cluster should represent all the reads that came from the same DNA strand. Recall that the polynucleotide sequencer may sequence multiple different DNA strands simultaneously so the raw output of sequence data from the polynucleotide sequencer could include reads that correspond to the multiple different DNA strands. In an implementation, clustering may be performed by the clusterization module 2012 shown in FIG. 20.

At 2308, a cluster is selected from the plurality of clusters. The cluster contains a clustered set of reads. If the clustering was accurate, all the reads in the clustered set of reads come from sequencing of the same DNA strand. At this point, prior to additional analysis, the cluster is identified only by its characteristic of having reads that cluster together. So, in some implementations, each cluster is analyzed in turn and the order of selecting individual clusters may be arbitrary. Multiple ones of the clusters may also be analyzed in parallel. In an implementation, selection of a cluster may be performed by the clusterization module 2012 shown in FIG. 20. Analysis may continue until trace reconstruction is performed on all clusters from the plurality of clusters.

At 2310, the clustered set of reads are aligned at a position of comparison spanning the clustered set of reads. In an implementation, the position of comparison may be the first position shared across the clustered set of reads. Thus, this original alignment may define a first position of comparison. The first position may be the left-most position (corresponding to the 5' end) or alternatively the right-most position (corresponding to the 3' end). In an implementation, alignment may be performed by the read alignment module 2014 shown in FIG. 20.

At 2312, a plurality consensus base call at the first position of comparison is determined. The plurality consensus base call is based at least in part on a most common base call across the clustered set of reads. The plurality consensus base call may be based in further part on an error profile associated with the polynucleotide sequencer. That is to say, base calls may be weighted based on the associated error profile (e.g., more certain base calls count for more and less certain base calls have less influence on the determination of the plurality consensus base call).

At 2314, a variant read from the clustered set of reads is identified. The variant read has a base call at the position of comparison that is different from the plurality consensus base call. In an implementation, the variant read may be identified by the variant read identification module 2018 shown in FIG. 20.

Moving now to FIG. 24, at 2416, a consensus string of base calls in a look-ahead window is identified. The consensus string is based on base calls for a subset of the clustered set of reads having the plurality consensus base call at the position of comparison (i.e., not variant reads). The look-ahead window is adjacent to the position of comparison. In some implementations, the look-ahead window may be two or three positions long.

At 2418, it is determined that an error type for the variant read at the position of comparison is a substitution based at least in part on base calls in a look-ahead window of the variant read matching the consensus string of base calls. An example of this relationship is shown in FIG. 13. In an implementation, the error type may be determined by the error classification module 2020.

At 2420, the position of comparison for the variant strand is moved ahead by one position.

At 2422, it is determined that an error type for the variant read at the position of comparison is a deletion based at least in part on a series of base calls in the variant read including the base call at the position of comparison and one or more base calls following the position of comparison matching the consensus string of base calls. An example of this relationship is shown in FIG. 14. In an implementation, the error type may be determined by the error classification module 2020.

At 2424, the position of comparison for the variant strand is moved ahead by zero positions.

At 2426, it is determined that an error type for the variant read at the position of comparison is an insertion. An insertion error is identified based at least in part on a base call in the variant read following the position of comparison matching the plurality consensus base call and a series of base calls in the variant read starting two positions following the position of comparison matching the consensus string of base calls. An example of this relationship is shown in FIG. 15. In an implementation, the error type may be determined by the error classification module 2020.

At 2428, the position of comparison for the variant strand is moved ahead by two positions.

At 2430, the position of comparison for reads in the subset of the clustered set of reads (i.e., the non-variant reads) is advanced ahead one position.

At 2432, a single consensus output sequence is determined from the clustered set of reads. In an implementation, the single consensus output sequence generated by the consensus output sequence generator 2024 shown in FIG. 20.

At 2434, the single consensus output sequence in converted into binary data. This may be the final manipulation of the information derived from the DNA strand before it is again used as a digital computer file. In an implementation, the change from sequence data to binary data may be performed by the conversion module 2028 shown in FIG. 20.

Figure 25:
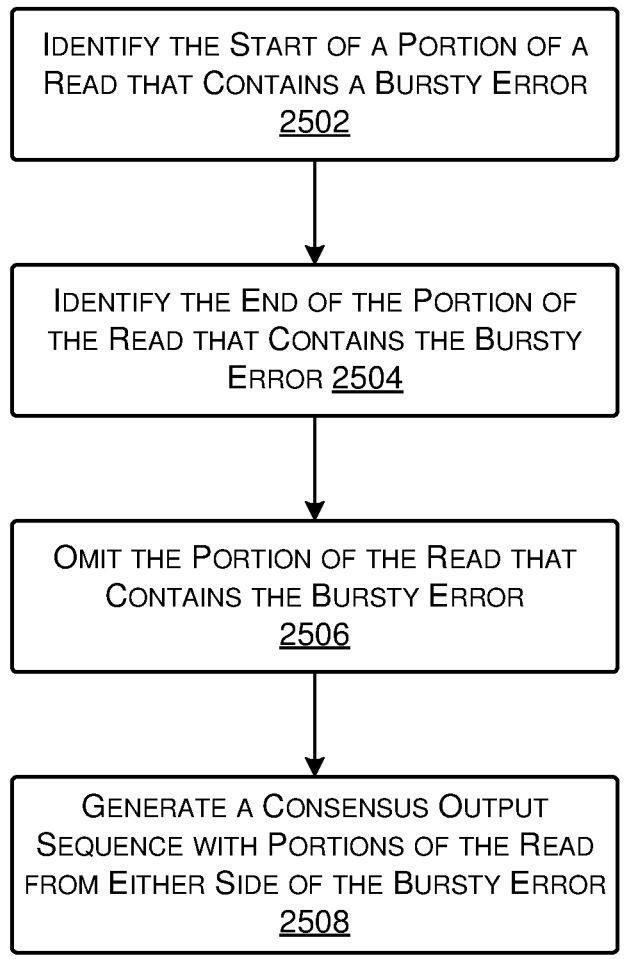
FIG. 25 shows an illustrative process for generating a consensus output sequence by omitting a portion of a read that contains a bursty error.

FIG. 25 shows process 2500 for identifying a portion of a read that contains a bursty error and generating a consensus output sequence with parts of that read other than the portion that contains the bursty error. Process 2500 may be performed together with either processes 2100 or 2300 as an alternative to discarding the entire read. As described above, the read may be generated from a DNA strand that stores digital data.

At 2502, the start of a portion of the read that contains the bursty error is identified. The start of the portion of the read that contains the bursty error may be identified by detection of the error itself. For example, in a read that does not match the consensus output sequence (a variant read) a position that is not classified as an insertion, deletion, or a substitution may be interpreted as the start of the portion of the read that contains the bursty error. An example of identifying an indeterminate error is shown in FIG. 16.

At 2504, an end of the location that contains the bursty error is identified. Identifying the end of the location that contains the bursty error finds a position in the read that is past the location of the bursty error so that further analysis farther down the read will find a sequence that can align with other reads in the cluster. The end of the bursty error is identified by a candidate position in the read. The candidate position is flanked by one or both of a match-backwards region (mb) or a match forward region (mf). As described above, the match-backwards region matches a consensus sequence generated from other ones of the plurality of reads in the same cluster and the match forward sequence matches a sequence generated by plurality voting from the sequences of other reads in the cluster.

At 2506, the portion of the read that contains the bursty error is omitted from generation of the consensus output sequence. Thus, the corresponding positions of the read between the position that is identified as the start of the bursty error and that position is identified as the end of the bursty error do not contribute to determining the consensus output sequence. For these positions in the consensus output sequence the base calls are determined based on some or all of the other reads in the cluster using techniques such as those illustrated in FIG. 21 and FIG. 24.

At 2508, the consensus output sequence is generated with portions of the read on either side of the portion that contains the bursty error. Thus, even though part of the read is not used to generate the consensus output sequence, other portions of the read are used. The portions of the read on either side of the portion with the bursty error are used to generate the consensus output sequence with the techniques described above by comparing values with the plurality of reads at a position of comparison while aligning the plurality of reads with respect to each other based on insertions, deletions, and substitutions. The consensus output sequence may be generated by the consensus output sequence generator 1024.

Figure 26:
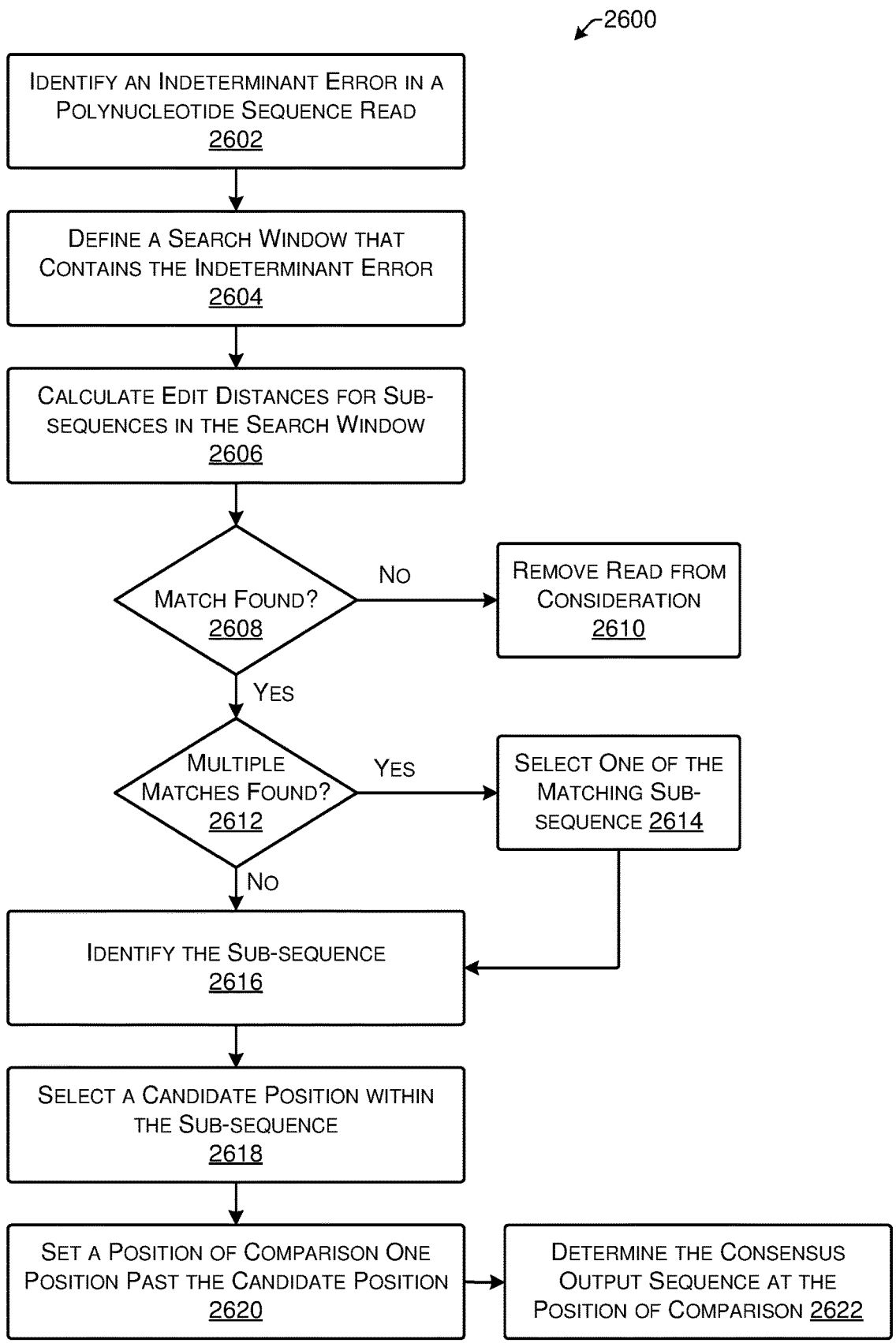
FIG. 26 shows an illustrative process for analyzing a read containing an indeterminant error in determining if there is a subsequence past the location of the indeterminant error that matches with other reads.

FIG. 26 shows process 2600 for determining if a read with an indeterminate error can be "brought back" by finding a matching sequence further down the read. Process 2600 may be performed together with either processes 1100 or 2300 as an alternative to discarding the entire read if the read includes an indeterminate error. The indeterminate error may be a bursty error that is not classified as any of an insertion, a deletion, or a substitution.

At 2602, an indeterminate error is identified in a read which is one of a plurality of reads of polynucleotide sequencer. The plurality of reads may be a group of reads in the same cluster as formed by, for example, the clusterization module 1012. The indeterminate error is an error relative to a consensus output sequence of the plurality of reads. The consensus output sequence may be generated by the consensus output sequence generator 1024.

The indeterminate error may be identified as shown in FIG. 6. Additionally, identification of the error as an indeterminate error may be performed by the error classification module 2020. The indeterminate error is located at a first position in the read. For example, the indeterminate error may be located at position 100 in a read with a total length of 200 base pairs. Thus, the consensus output sequence may be identified for positions 1-99 prior to determining that there is an indeterminate error at position 100.

At 2604, a search window is defined that includes a second position in the read located at a distance at least delay past the first position. In an implementation, the second position is the position represented by $k_0$. In an implementation, a length of the delay may be between 4 and 10 positions. For example, if the delay distance is 8 positions then the search window is a window that includes position 108 in this example read. The search window possibly contains some positions that have base calls which are not in error.

Limiting the search to a search window rather than the entire remainder of that read focuses the search for a matching sequence to an area near where a matching sequence, if it exists, should be found. A shorter search window makes it less likely that a matching sequence will be identified, but a longer search window increases the probability of a false positive match. In an implementation, a length of the search window may be between 9 and 20 positions. As described above, the search window may include two portions: a backward search window (bsw) for positions before $k_0$ and a forward search window (fsw) for positions after $k_0$. The bsw and fsw may be the same length as each other. For example, both the bsw and the fsw may be about 5-8 positions long. Thus, the search window includes the bsw, $k_0$, and the fsw.

At 2606, edit distances are calculated for sub-sequences in the search window as determined from a comparison sequence. The comparison sequence may include a match-backward sequence (mb) that is that consensus output sequence of corresponding positions in some or all of the other reads in the plurality of sequence reads. The length of the match-backwards sequence may be about 1-11 positions.

The consensus output sequence of the plurality of sequence reads may be determined by identifying a plurality vote for the position of consideration while accounting for insertion errors, deletion errors, and substitution errors, and proceeds sequentially from a base call position currently under consideration to an adjacent base call position. Thus, all of the other reads from the same cluster (or all of the other reads that do not also have indeterminate errors at this position) may be used to generate a consensus output sequence as described above.

The comparison sequence may also include a match-forward sequence (mf). As described above, the match-forward sequence is adjacent to the match-backward sequence and positioned past the location of the match-backward sequence (i.e., further away from the location of the indeterminate error). The match-forward sequence corresponds to a portion of the aligned reads for which the consensus output sequence has not yet been determined. Because the consensus output sequence has not been determined for the positions included in the match-forward sequence, a plurality consensus vote from the base calls of the other reads in the cluster is used to determine if there is a match. The plurality consensus vote simply identifies the most frequent base call at each position without attempting to account for errors such as insertions, deletions, and substitutions. If the match-forward sequence is included, a length of the match forward sequence is 1-10 positions.

In an implementation, a sliding window may be moved across the search window and the sequence within the sliding window may be used as the sub-sequence which is compared to the consensus output sequence. Edit distance can be calculated for each of the positions of the sliding window. Depending on its position, the sliding window may include relatively more or relatively less of the match-backward sequence and the match-forward sequence.

At 2608, it is determined if a match is found between any of the sub-sequences and the consensus output sequence at the corresponding positions. A match is identified by the edit distance being less than a threshold value. For example, if the threshold value is 0, then only exact matches are treated as matching. If the threshold value for the edit distance is 1, then two sequences that have a single base call difference can be classified as matches.

If no match is found, then process 2600 proceeds along "no" path to 2610 and the read is removed from consideration. The lack of a match indicates that there is no subsequence within the search window that matches with the consensus output sequence/plurality consensus vote. Thus, the read may have extensive errors and the most accurate consensus output sequence may be obtained by ignoring this read.

If, however, a match is found, then process 2600 proceeds along the "yes" path to 2612. At 2612, it is determined if multiple matches are found. Within the search window there may be more than one subsequence that matches the corresponding base calls of the consensus output sequence. If this is the case, then process 2600 proceeds along "yes" path to 2614.

At 2614, one of the matching subsequences is selected. Out of two or more matching subsequences, one may be selected by any of a number of techniques such as random selection, selecting the one of the subsequences that is closest to the beginning of the read (e.g., 5'-end), selecting the one of the subsequences that is farthest from the making of the read, or by another criteria.

At 2616, a single sub-sequence in the search window with an edit distance less than a threshold value is identified. This is a matching subsequence indicating that following the location of the indeterminate error, there is a portion of the read that once again can be aligned with the other reads in the cluster.

At 2618, a candidate position within the matching subsequence is selected. The matching sub-sequence may have a length of about 5-15 positions and one of those positions is selected for use as the candidate position. The candidate position may be the same as the candidate position (k) shown in FIG. 7. In an implementation, the candidate position may be the position in the match-backward sequence that is farthest from the position where the indeterminate error begins. Thus, if there is no match-forward sequence, then the candidate position may be the position within the matching subsequence at the end of the matching subsequence. If there is a match-forward sequence, then the candidate position may be the position in the match-backward sequence directly adjacent to the match-forward sequence.

At 2620, a position of comparison is set one position past the candidate position. The position of comparison may be the same as the position of comparison 600 shown in FIG. 6. Thus, the location of the matching sub-sequence and the candidate position are used to determine how to realign this read with the other reads following the indeterminate error. The position of comparison is located at a third position in the read which, using the notation introduced above, may be indicated as being located at k+1.

At 2622, the consensus output sequence from the plurality reads is determined at the third position. This position of comparison is used to compare the read as well as other reads in the cluster to determine a consensus output sequence as described above. Analysis of the read may continue until the end of the read is reached and any variations in the read from the output sequence may be handled as described earlier in this disclosure.

Many of the parameters used to identify a matching sub-sequence and ultimately determine the position of comparison such as the delay, bsw, fsw, mb, and mf have lengths that can vary. The lengths used to analyze a given set of sequence data may be determined experimentally by testing different values for the length of each of the delay, search window, mb, and mf. Each may be varied within a range of values and different combinations may be tested.

For each combination of lengths, a number of clusters that can be generated from the reads produced by the polynucleotide sequencer is determined. Generating a larger number of clusters indicates that more of the reads are able to be used even with indeterminate errors and that more of the data output by the polynucleotide sequencer is contributing to generation of consensus output sequences. Thus, the combination of values that results in formation of a largest number of clusters of reads from the plurality of sequence reads may be used as the lengths for the parameters.

Example 27—Example Synthesis

Digital information that is intended for storage as DNA molecules can be converted into information representing a string of nucleotides (e.g., a nucleotide symbol string). The information representing the string of nucleotides (i.e., a string of letters representing an order of nucleotide bases) is used for DNA-synthesis templates that instruct an oligonucleotide synthesizer to chemically synthesize a DNA molecule, nucleotide by nucleotide. Artificial synthesis of DNA allows for creation of synthetic DNA molecules with arbitrary series of the bases in which individual monomers of the bases are assembled together into a polymer of nucleotides. The oligonucleotide synthesizer may be any oligonucleotide synthesizer using any recognized technique for DNA synthesis. The term "oligonucleotide" as used herein is defined as a molecule including two or more nucleotides.

The coupling efficiency of a synthesis process is the probability that a nucleotide binds to an existing partial strand at each step of the process. Although the coupling efficiency for each step can be higher than 99%, this small error still results in an exponential decrease of product yield with increasing length and limits the size of oligonucleotides that can be efficiently synthesized at present to about 200 nucleotides. Therefore, the length of the DNA strands put into storage is around 100 to 200 base pairs (bp). This length will increase with advances in oligonucleotide synthesis technology.

The synthetic DNA produced by the oligonucleotide synthesizer may be transferred to a DNA storage library. There are many possible ways to structure a DNA storage library. In addition to structure on the molecular level by appending identifying sequences to the DNA strands, a DNA storage library may be structured by physically separating DNA strands into one or more DNA pools. For illustration, a DNA pool is sometimes shown as a flip top tube representing a physical container for multiple DNA strands. DNA strands are generally most accessible for manipulation by bio-technological techniques when the DNA is stored in a liquid solution. Thus, the DNA pool can be implemented as a chamber filled with liquid, in many implementations water, and thousands, millions, or more individual DNA molecules may be present in a DNA pool.

Besides being in a liquid suspension, the DNA strands in the DNA storage library may be present in a glassy (or vitreous) state, as a lyophilized product, as part of a salt, adsorbed on the surface of a nanoparticle, or another format. The structure of the DNA pools may be implemented as any type of mechanical, biological, or chemical arrangement that holds a volume of liquid including DNA to a physical location. Storage may also be in a non-liquid form such as a solid bead or by encapsulation. For example, a single flat surface having a droplet present thereon, with the droplet held in part by surface tension of the liquid, even though not fully enclosed within a container, is one implementation of a DNA pool. The DNA pool may include single-stranded DNA (ssDNA), double-stranded DNA (dsDNA), single-stranded RNA (ssRNA), double-stranded RNA (dsRNA), DNA-RNA hybrid strands, or any combination, including use of unnatural bases.

Example 28—Example Sequencing

Stored nucleotide strands can be sequenced with a polynucleotide sequencer. In some implementations, DNA strands may be prepared for sequencing by amplification using polymerize chain reaction (PCR) to create a large number of DNA strands that are identical copies of each other. The need for PCR amplification prior to sequencing may depend on the specific sequencing technology used. PCR may itself be a source of error, although at a much lower level than current sequencing technology. At present, PCR techniques typically introduce one error per 10,000 bases. Thus, on average, for every 100 reads of 100 bases there will be one error that is the result of PCR. The errors introduced by PCR are generally distributed randomly so the trace reconstruction system will be able to correct some PCR-induced errors.

The polynucleotide sequencer reads the order of nucleotide bases in a DNA strand and generates one or more reads from that strand. Polynucleotide sequencers use a variety of techniques to interpret molecular information and may introduce errors into the data in both systematic and random ways. Errors can usually be categorized as substitution errors, where the real code is substituted with an incorrect code (for example A swapping with G), insertions, or deletions, where a random unit is inserted (for example AGT becoming AGCT) or deleted (for example AGTA becoming ATA). Each position in a read is an individual base call determined by the polynucleotide sequencer based on properties sensed by components of the polynucleotide sequencer. The various properties sensed by the polynucleotide sequencer vary depending on the specific sequencing technology used. A base call represents a determination of which of the four nucleotide bases—A, G, C, and T (or U)—in a strand of DNA (or RNA) is present at a given position in the strand. Sometimes the base calls are wrong, and this is a source of error introduced by sequencing. Polynucleotide sequencing includes any method or technology that is used to generate base calls from a strand of DNA or RNA.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used is nanopore sequencing. A nanopore is a small hole of the order of 1 nanometer in diameter Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technology that can be used includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure that enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into an instrument, e.g., a HeliScope™ sequencer, and a laser illuminates the surface of the flow cell, revealing the position of each template. A CCD camera can map the position of the templates on the flow cell surface. The template fluorescent-label is then cleaved and washed away. The sequencing reaction begins by introducing a DNA polymerase and a fluorescently-labeled nucleotide. The oligo-T nucleic acid serves as a primer. The polymerase incorporates the labeled nucleotides to the primer in a template-directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently-labeled nucleotides until the desired read length is achieved. Sequence information is collected with each nucleotide addition step.

Another example of a DNA sequencing technique that can be used is SOLiD™ technology (Applied Biosystems). In SOLiD™ sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, templates, and PCR components. Following PCR, the templates are denatured and beads are enriched to separate the beads with extended templates. Templates on the selected beads are subjected to a 3' modification that permits bonding to a glass slide.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

Technologies for sequencing DNA are associated with some level of error and the type and frequency of errors differs by sequencing technology. For example, sequencing-by-synthesis creates an error in about 2% of the base calls. A majority of these errors are substitution errors. Nanopore sequencing has a much higher error rate of about 15 to 40% and most of the errors caused by this sequencing technology are deletions. The error profile of a specific sequencing technology may describe the overall frequency of errors as well as the relative frequency of various types of errors.

In some implementations, the polynucleotide sequencer provides quality information that indicates a level of confidence in the accuracy of a given base call. The quality information may indicate that there is a high level or a low level of confidence in a particular base call. For example, the quality information may be represented as a percentage, such as 80% confidence, in the accuracy of a base call. Additionally, quality information may be represented as a level of confidence that each of the four bases is the correct base call for a given position in a DNA strand. For example, quality information may indicate that there is 80% confidence the base call is a T, 18% confidence the base call is an A, 1% confidence the base call is a G, and 1% confidence the base call is a C. Thus, the result of this base call would be T because there is higher confidence in that nucleotide being the correct base call than in any of the other nucleotides. Quality information does not identify the source of an error, but merely suggests which base calls are more or less likely to be accurate.

The polynucleotide sequencer provides output, multiple noisy reads (possibly of multiple DNA strands), in electronic format to a trace reconstruction system. The output may include the quality information as metadata for otherwise associated with the reads produced by the polynucleotide sequencer.

The trace reconstruction system can be implemented as an integral part of the polynucleotide sequencer. The polynucleotide sequencer can include an onboard computer that implements the trace reconstruction system. Alternatively, the trace reconstruction system may be implemented as part of a separate computing device that is connected to the polynucleotide sequencer through a wired or wireless connection. For example, the computing device may be a desktop or notebook computer used to receive data from and/or to control the polynucleotide sequencer. A wired connection may include one or more wires or cables physically connecting the computing device to the polynucleotide sequencer. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. The trace reconstruction system may also be implemented as part of a cloud-based or network system using one or more servers that communicate with the polynucleotide sequencer via a network. The network may be implemented as any type of communications network such as a local area network, a wide area network, a mesh network, an ad hoc network, a peer-to-peer network, the Internet, a cable network, a telephone network, and the like. Additionally, the trace reconstruction system may be implemented in part by any combination of the polynucleotide sequencer, the computing device, and the servers.

The trace reconstruction system outputs a digital representation of the result strands for further processing as described herein. In practice, the results of integrity checking can be incorporated into the trace reconstruction process if desired.

Example 29—Example Computing Systems

Figure 27:
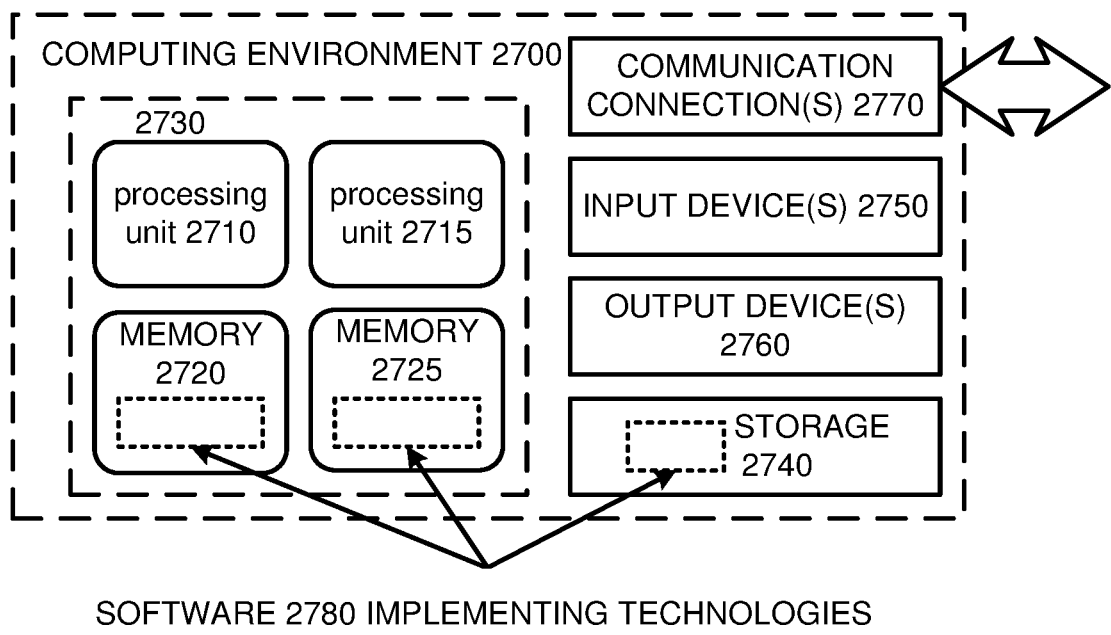
FIG. 27 is a block diagram of an example computing system in which described embodiments can be implemented.

FIG. 27 depicts an example of a suitable computing system 2700 in which digital aspects of the described innovations can be implemented. The computing system 2700 is not intended to suggest any limitation as to scope of use or functionality of the present disclosure, as the innovations can be implemented in diverse computing systems.

With reference to FIG. 27, the computing system 2700 includes one or more processing units 2710, 2715 and memory 2720, 2725. In FIG. 27, this basic configuration 2730 is included within a dashed line. The one or more processing units execute computer-executable instructions, such as for implementing the features described in the examples herein. The one or more processing units 2710, 2715 can be any combination or central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 2710, 2715 may be implemented in software (e.g., ultimately executed on hardware) and/or firmware in addition to hardware implementations.

In a multi-processing system, multiple processing units execute computer-executable instructions to increase processing power. The tangible memory 2720, 2725 can be volatile memory (e.g., registers, cache, RAM), non-volatile memory (e.g., ROM, EEPROM, flash memory, etc.), or some combination of the two, accessible by the processing unit(s) 2710, 2715. The memory 2720, 2725 stores software 2780 implementing one or more innovations described herein, in the form of computer-executable instructions suitable for execution by the processing unit(s) 2710, 2715.

Functionality can also be performed, at least in part, by one or more hardware logic components. For example, Field-programmable Gate Arrays (FPGAs), Application-specific Standard Products (ASSPs), System-on-a chip systems (SOCs), Complex Programmable Logic Devices (CPLDs), and the like can be used.

A computing system 2700 can have additional features. For example, the computing system 2700 includes storage 2740, one or more input devices 2750, one or more output devices 2760, and one or more communication connections 2770, including input devices, output devices, and communication connections for interacting with a user. An interconnection mechanism (not shown) such as a bus, controller, or network interconnects the components of the computing system 2700. Typically, operating system software (not shown) provides an operating environment for other software executing in the computing system 2700, and coordinates activities of the components of the computing system 2700.

The tangible storage 2740 can be removable or non-removable, and includes magnetic disks, magnetic tapes or cassettes, CD-ROMs, DVDs, or any other medium which can be used to store information in a non-transitory way and which can be accessed within the computing system 2700. The storage 2740 stores instructions for the software 2780 implementing one or more innovations described herein.

The input device(s) 2750 can be an input device such as a keyboard, mouse, pen, or trackball, a voice input device, a scanning device, touch device (e.g., touchpad, display, or the like) or another device that provides input to the computing system 2700. The output device(s) 2760 can be a display, printer, speaker, CD-writer, or another device that provides output from the computing system 2700.

The communication connection(s) 2770 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Example 30—Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example 31—Example Cloud Computing Environment

Figure 28:
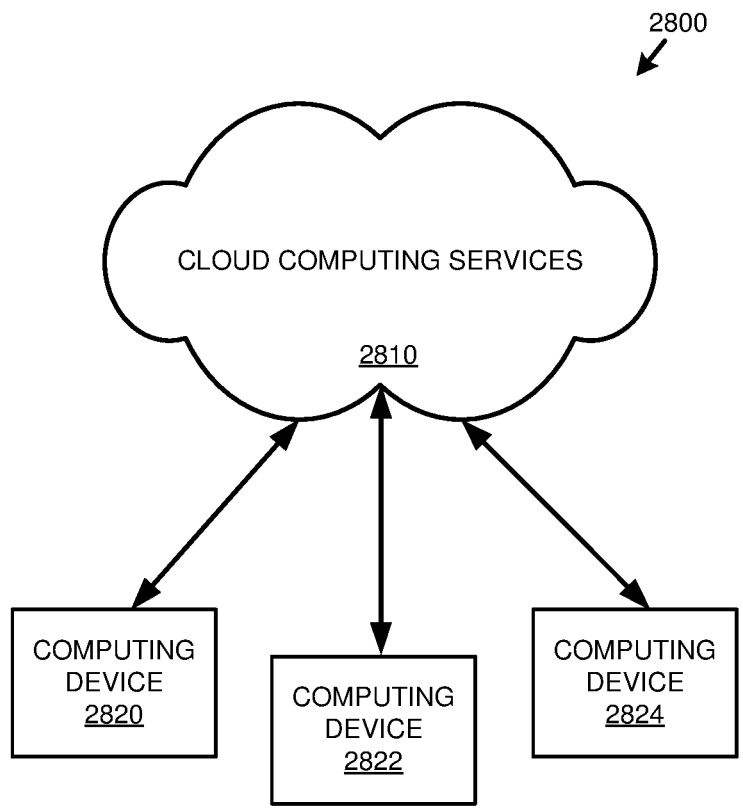
FIG. 28 is a block diagram of an example cloud computing environment that can be used in conjunction with the technologies described herein.

FIG. 28 depicts an example cloud computing environment 2800 in which the described technologies can be implemented, including, e.g., the system 100 of FIG. 1 and other systems herein. The cloud computing environment 2800 comprises cloud computing services 2810. The cloud computing services 2810 can comprise various types of cloud computing resources, such as computer servers, data storage repositories, networking resources, etc. The cloud computing services 2810 can be centrally located (e.g., provided by a data center of a business or organization) or distributed (e.g., provided by various computing resources located at different locations, such as different data centers and/or located in different cities or countries).

The cloud computing services 2810 are utilized by various types of computing devices (e.g., client computing devices), such as computing devices 2820, 2822, and 2824.

For example, the computing devices (e.g., 2820, 2822, and 2824) can be computers (e.g., desktop or laptop computers), mobile devices (e.g., tablet computers or smart phones), or other types of computing devices. For example, the computing devices (e.g., 2820, 2822, and 2824) can utilize the cloud computing services 2810 to perform computing operations (e.g., data processing, data storage, and the like).

In practice, cloud-based, on-premises-based, or hybrid scenarios can be supported.

Example 32—Example Implementations

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Example 33—Example Embodiments

Any of the following embodiments can be implemented.

Clause 1. A method comprising:

in a first pass through a plurality of nucleotide symbol strings representing nucleotide strand sequence reads from a polynucleotide sequencer, wherein the nucleotide strand sequence reads represent logically ordered nucleotide symbol strings comprising encoded data with redundancy information, placing a nucleotide symbol string representing a solitary nucleotide strand sequence read in a first order position of an ordered map; and in a second pass through the nucleotide symbol strings representing nucleotide strand sequence reads from the polynucleotide sequencer, performing cluster-based trace reconstruction, wherein the cluster-based trace reconstruction generates a reconstructed nucleotide symbol string and places the reconstructed nucleotide symbol string in a second order position of the ordered map.

Clause 2. The method of Clause 1 wherein:

the first pass comprises performing integrity verification on the nucleotide symbol string; and placing in the first order position is performed responsive to determining that the nucleotide symbol string passes integrity verification.

Clause 3. The method of Clause 2 wherein:

the integrity verification of the nucleotide symbol string comprises performing integrity verification with redundancy nucleotide symbols originating from the solitary nucleotide strand sequence read.

Clause 4. The method of any of Clauses 2-3 wherein the method further comprises:

during the first pass, before integrity verification, performing error correction on the nucleotide symbol string with redundancy nucleotide symbols originating from the solitary nucleotide strand sequence read.

Clause 5. The method of any of Clauses 2-4 wherein:

redundancy nucleotide symbols in the solitary nucleotide strand sequence read are partitioned into a first part and second part; and the first pass comprises implementing error correction for the solitary nucleotide strand sequence read with the first part and implementing integrity verification for the solitary nucleotide strand sequence read with the second part.

Clause 6. The method of Clause 5 wherein:

the error correction corrects a substitution error.

Clause 7. The method of any of Clauses 5-6 wherein:

the error correction corrects an insertion or deletion error.

Clause 8. The method of any of Clauses 1-7 further comprising:

forming a cluster of a subset of the nucleotide symbol strings;

wherein the cluster-based trace reconstruction generates the reconstructed nucleotide symbol string based on the cluster.

Clause 9. The method of any of Clauses 1-8 further comprising:

responsive to determining, during the first pass, that a plurality of different, conflicting nucleotide symbol strings appear to be mapped to a single position, postponing processing for the conflicting nucleotide symbol strings until the second pass.

Clause 10. The method of any of Clauses 1-9 further comprising:

outputting an ordered list of nucleotide symbol strings representing the encoded data;

wherein the ordered list comprises the nucleotide symbol string representing a solitary nucleotide strand sequence read based on the nucleotide strand sequence read in the first order position; and wherein the ordered list comprises the reconstructed nucleotide symbol string in the second order position.

Clause 11. The method of any of Clauses 1-10 wherein:

the second pass incorporates the solitary nucleotide strand sequence read in the cluster-based trace reconstruction.

Clause 12. The method of any of Clauses 1-11 further comprising:

removing a cluster in which the solitary nucleotide strand sequence read appears from the cluster-based trace reconstruction.

Clause 13. A system comprising:

one or more processors;

memory coupled to the one or more processors;

a string position map storing a mapping between addresses and nucleotide symbol strings;

wherein the memory comprises computer-executable instructions causing the one or more processors to perform operations comprising:

during processing of a nucleotide symbol string representing a solitary strand read by a sequencer, responsive to determining that the nucleotide symbol string passes integrity verification, placing the nucleotide symbol string into the string position map; and during processing of a cluster of nucleotide symbol strings representing a plurality of strands read by the sequencer, reconstructing a reconstructed nucleotide symbol string based on the cluster and placing the reconstructed nucleotide symbol string into the string position map.

Clause 14. The system of Clause 13 wherein:

the nucleotide symbol string and solitary strand and the plurality of strands read by the sequencer represent logically ordered nucleotide symbol strings comprising encoded data with redundancy information that represents an original data file.

Clause 15. The system of any of Clauses 13-14 wherein:

the nucleotide symbol string representing the solitary strand read by the sequencer comprises redundancy information configured to correct one or more substitution errors; and the operations further comprise:

correcting the nucleotide symbol string before placing it into the string position map.

Clause 16. The system of any of Clauses 13-15 wherein:

the nucleotide symbol string representing the solitary strand read by the sequencer comprises redundancy information configured to correct one or more insertion or deletion errors; and the operations further comprise:

correcting the nucleotide symbol string before placing it into the string position map.

Clause 17. The system of any of Clauses 13-16 wherein:

the nucleotide symbol string representing the solitary strand read by the sequencer comprises inner redundancy information partitioned into two portions, wherein one portion is configured to correct one or more substitution errors and another portion is configured to correct one or more insertion or deletion errors; and the operations further comprise:

correcting the nucleotide symbol string with one of the portions before placing it into the string position map; and verifying integrity of the nucleotide symbol string with another of the portions before placing it into the string position map.

Clause 18. The system of any of Clauses 13-17 wherein the operations further comprise:

removing a cluster in which the nucleotide symbol string representing the solitary strand appears from consideration during cluster-based trace reconstruction.

Clause 19. The system of any of Clauses 13-18 wherein the operations further comprise:

incorporating the nucleotide symbol string representing the solitary strand in a cluster formation process during cluster-based trace reconstruction.

Clause 20. One or more computer-readable media comprising:

computer-executable instructions capable of causing a computing system to place, in a first order position of an ordered map, a nucleotide symbol string representing a solitary nucleotide strand sequence read, wherein the nucleotide symbol string is one out of a plurality of nucleotide symbol strings representing respective nucleotide strand sequence reads from a polynucleotide sequencer, wherein the nucleotide strand sequence reads represent logically ordered comprising encoded data with redundancy information, and wherein the nucleotide symbol string is placed in the first order position of the ordered map responsive to determining that it passes integrity verification; and computer-executable instructions capable of causing the computing system to perform cluster-based trace reconstruction on the plurality of nucleotide symbol strings, wherein the cluster-based trace reconstruction generates a reconstructed nucleotide symbol string out of a cluster of the plurality of nucleotide symbol strings and places the reconstructed nucleotide symbol string in a second order position of the ordered map.

Clause 21. One or more computer-readable media comprising computer-executable instructions that when executed by a computing system perform the method of any of Clauses 1-12.

Example 34—Example Alternatives

The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the following claims.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~1 kb), which was created on Oct. 1, 2019 which is incorporated by reference herein.

What is claimed is:

1. A method comprising:

in a first pass through a plurality of nucleotide symbol strings representing nucleotide strand sequence reads from a polynucleotide sequencer, wherein the nucleotide strand sequence reads represent logically ordered nucleotide symbol strings comprising encoded data with redundancy information, placing a nucleotide symbol string representing a solitary nucleotide strand sequence read in a first order position of an ordered map; and in a second pass through the nucleotide symbol strings representing nucleotide strand sequence reads from the polynucleotide sequencer, performing cluster-based trace reconstruction, wherein the cluster-based trace reconstruction generates a reconstructed nucleotide symbol string and places the reconstructed nucleotide symbol string in a second order position of the ordered map;

wherein the ordered map maps nucleotide symbol strings to positions in an overall ordering of data to be decoded.

2. The method of claim 1 wherein:

the first pass comprises performing integrity verification on the nucleotide symbol string representing the solitary nucleotide strand sequence read; and placing in the first order position is performed responsive to determining that the nucleotide symbol string representing the solitary nucleotide strand sequence read passes integrity verification.

3. The method of claim 2 wherein:

the integrity verification of the nucleotide symbol string comprises performing integrity verification with redundancy nucleotide symbols originating from the solitary nucleotide strand sequence read.

4. The method of claim 2 wherein the method further comprises:

during the first pass, before integrity verification, performing error correction on the nucleotide symbol string with redundancy nucleotide symbols originating from the solitary nucleotide strand sequence read.

5. The method of claim 2 wherein:

redundancy nucleotide symbols in the solitary nucleotide strand sequence read are partitioned into a first part and second part; and the first pass comprises implementing error correction for the solitary nucleotide strand sequence read with the first part and implementing integrity verification for the solitary nucleotide strand sequence read with the second part.

6. The method of claim 5 wherein:

the error correction corrects a substitution error.

7. The method of claim 5 wherein:

the error correction corrects an insertion or deletion error.

8. The method of claim 1 further comprising:

forming a cluster of a subset of the nucleotide symbol strings;

wherein the cluster-based trace reconstruction generates the reconstructed nucleotide symbol string based on the cluster.

9. The method of claim 1 further comprising:

responsive to determining, during the first pass, that a plurality of different, conflicting nucleotide symbol strings appear to be mapped to a single position, postponing processing for the conflicting nucleotide symbol strings until the second pass.

10. The method of claim 1 further comprising:

outputting an ordered list of nucleotide symbol strings representing the encoded data;

wherein the ordered list comprises the nucleotide symbol string representing a solitary nucleotide strand sequence read based on the nucleotide strand sequence read in the first order position; and wherein the ordered list comprises the reconstructed nucleotide symbol string in the second order position.

11. The method of claim 1 wherein:

the second pass incorporates the solitary nucleotide strand sequence read in the cluster-based trace reconstruction.

12. The method of claim 1 further comprising:

removing a cluster in which the solitary nucleotide strand sequence read appears from the cluster-based trace reconstruction.

13. A system comprising:
one or more processors;
memory coupled to the one or more processors;
a string position map storing a mapping between addresses and nucleotide symbol strings;
wherein the memory comprises computer-executable instructions causing the one or more processors to perform operations comprising:
during processing of a nucleotide symbol string representing a solitary strand read by a sequencer, responsive to determining that the nucleotide symbol string representing the solitary strand read by the sequencer passes integrity verification, placing the nucleotide symbol string into the string position map; and
during processing of a cluster of nucleotide symbol strings representing a plurality of strands read by the sequencer, reconstructing a reconstructed nucleotide symbol string based on the cluster and placing the reconstructed nucleotide symbol string into the string position map.

14. The system of claim 13 wherein:
the solitary strand and the plurality of strands read by the sequencer represent logically ordered nucleotide symbol strings comprising encoded data with redundancy information that represents an original data file.

15. The system of claim 13 wherein:
the nucleotide symbol string representing the solitary strand read by the sequencer comprises redundancy information configured to correct one or more substitution errors; and
the operations further comprise:
correcting the nucleotide symbol string before placing it into the string position map.

16. The system of claim 13 wherein:
the nucleotide symbol string representing the solitary strand read by the sequencer comprises redundancy information configured to correct one or more insertion or deletion errors; and
the operations further comprise:
correcting the nucleotide symbol string before placing it into the string position map.

17. The system of claim 13 wherein:
the nucleotide symbol string representing the solitary strand read by the sequencer comprises inner redundancy information partitioned into two portions, wherein one portion is configured to correct one or more substitution errors and another portion is configured to correct one or more insertion or deletion errors; and
the operations further comprise:
correcting the nucleotide symbol string with one of the portions before placing it into the string position map; and
verifying integrity of the nucleotide symbol string with another of the portions before placing it into the string position map.

18. The system of claim 13 wherein the operations further comprise:
removing a cluster in which the nucleotide symbol string representing the solitary strand appears from consideration during cluster-based trace reconstruction.

19. The system of claim 13 wherein the operations further comprise:
incorporating the nucleotide symbol string representing the solitary strand in a cluster formation process during cluster-based trace reconstruction.

20. One or more computer-readable media not consisting of a signal comprising:
computer-executable instructions capable of causing a computing system to place, in a first order position of an ordered map, a nucleotide symbol string representing a solitary nucleotide strand sequence read, wherein the nucleotide symbol string is one out of a plurality of nucleotide symbol strings representing respective nucleotide strand sequence reads from a polynucleotide sequencer, wherein the nucleotide strand sequence reads represent logically ordered comprising encoded data with redundancy information, and wherein the nucleotide symbol string is placed in the first order position of the ordered map responsive to determining that the nucleotide symbol string representing the solitary nucleotide strand sequence read passes integrity verification; and
computer-executable instructions capable of causing the computing system to perform cluster-based trace reconstruction on the plurality of nucleotide symbol strings, wherein the cluster-based trace reconstruction generates a reconstructed nucleotide symbol string out of a cluster of the plurality of nucleotide symbol strings and places the reconstructed nucleotide symbol string in a second order position of the ordered map.

* * * * *